US010568952B2

(12) United States Patent
Dorsey et al.

(10) Patent No.: US 10,568,952 B2
(45) Date of Patent: Feb. 25, 2020

(54) METHODS AND COMPOSITIONS FOR GROWTH, STORAGE, AND USE OF BACTERIAL PREPARATIONS FOR WOUND AND SURFACE TREATMENTS

(71) Applicant: Atterx Biotherapeutics, Inc., Madison, WI (US)

(72) Inventors: Caleb William Dorsey, Verona, WI (US); Joshua Aaron Smith, New Glarus, WI (US); Steven Robert Watt, Windsor, WI (US)

(73) Assignee: Atterx Biotherapeutics, Inc., Madison, WI (US)

(*) Notice: Subject to any disclaimer, the term of this patent is extended or adjusted under 35 U.S.C. 154(b) by 170 days.

(21) Appl. No.: 15/539,774

(22) PCT Filed: Dec. 23, 2015

(86) PCT No.: PCT/US2015/000246
§ 371 (c)(1),
(2) Date: Jun. 26, 2017

(87) PCT Pub. No.: WO2016/105510
PCT Pub. Date: Jun. 30, 2016

(65) Prior Publication Data
US 2018/0333475 A1    Nov. 22, 2018

Related U.S. Application Data

(60) Provisional application No. 62/096,980, filed on Dec. 26, 2014.

(51) Int. Cl.
*C12N 15/00* (2006.01)
*A61K 39/02* (2006.01)
*C12N 1/20* (2006.01)

(52) U.S. Cl.
CPC ............... *A61K 39/02* (2013.01); *C12N 1/20* (2013.01); *C12N 15/00* (2013.01)

(58) Field of Classification Search
CPC ...................................................... A61K 39/02
See application file for complete search history.

(56) References Cited

U.S. PATENT DOCUMENTS

2006/0003454 A1* 1/2006 Suzuki .................. C12N 1/04
435/471

* cited by examiner

*Primary Examiner* — Albert M Navarro
(74) *Attorney, Agent, or Firm* — Casimir Jones, S.C.; Mary Ann D. Brow

(57) ABSTRACT

The present invention relates to the field of bacteriology. In particular, the invention relates to methods and compositions for treatment and prevention of infection in wounds, and methods for producing and storing bacterial donor organisms for conjugation-based antibacterial agents. The present invention relates to the field of bacteriology and pharmacology. In particular, the invention relates to novel compositions (e.g., antimicrobial agents) and methods of using the same for treating tissue (e.g., lesions of the skin and other soft tissues) comprising the killing or altering (e.g., inhibiting) growth and virulence of populations of microorganisms.

50 Claims, 35 Drawing Sheets

Specification includes a Sequence Listing.

FIG.1
GENERATION OF BACKBONE VECTOR WITH NO KILLING MECHANISMS pGEM5Zf
↓ Annealed adapter oligos to generate a different multiple cloning site, cloned into AatII and NsiI sites in pGem5Zf.

pCON1-41
↓ Annealed adapter oligos to generate a different larger multiple cloning site, cloned into NheI and ApaI sites in pCON1-41.

pCON4-91
↓ Annealed adapter oligos with internal PstI and NotI sites were digested with XbaI and NsiI and cloned into cognate sites in pCON4-91 to facilitate the cloning of RSF1010 into this vector.

pCON17-11
↓ RSF1010 was digested with PstI and NotI and cloned into cognate sites in pCON17-11 (RSF1010 repABC, mobABC, oriT and oriV) are in the new construct.

pCON17-12
↓ tetA (tetracycline resistance cassette) was cloned into ApaI and NotI sites of pCON17-12. This was introduced as a convenient selection tool at this point.

pCON17-19
↓ Annealed adapter oligos to generate an additional multiple cloning site (just 5' to tetA), cloned into XbaI and ApaI sites in pCON17-19.

pCON19-22

FIG.1 (cont'd)

pCON19-22

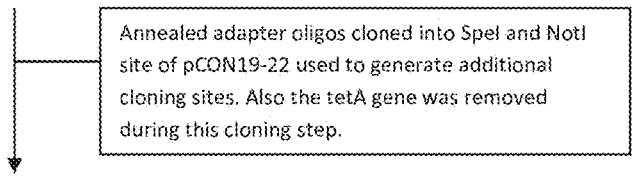

Annealed adapter oligos cloned into SpeI and NotI site of pCON19-22 used to generate additional cloning sites. Also the tetA gene was removed during this cloning step.

pCON42-28

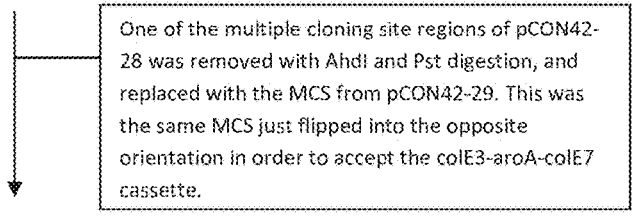

One of the multiple cloning site regions of pCON42-28 was removed with AhdI and Pst digestion, and replaced with the MCS from pCON42-29. This was the same MCS just flipped into the opposite orientation in order to accept the colE3-aroA-colE7 cassette.

pCON42-31- This is the donor backbone vector capable of being transferred via conjugation into different gram negative bacteria. This vector does not have the killing components at this point. The colE3-aroA-colE7 cassette gets added to pCON42-31 at the SacI and PstI sites, thereby eliminating the AmpR and f1 origin in the final pCON44-74.

FIG.2
GENERATION OF BACTERIOCIDAL KILLING CASSETTE pCON32-43 + pCON32-42 + pCON32-40

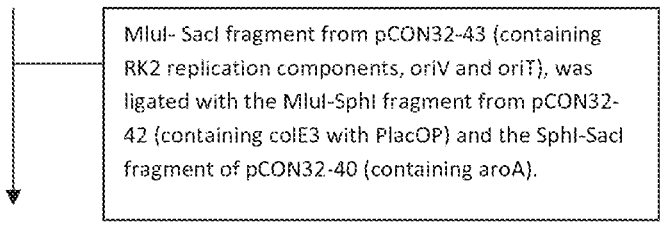

MluI-SacI fragment from pCON32-43 (containing RK2 replication components, oriV and oriT), was ligated with the MluI-SphI fragment from pCON32-42 (containing colE3 with PlacOP) and the SphI-SacI fragment of pCON32-40 (containing aroA).

pCON32-53

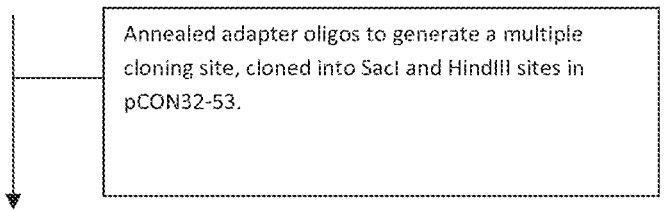

Annealed adapter oligos to generate a multiple cloning site, cloned into SacI and HindIII sites in pCON32-53.

pCON32-62

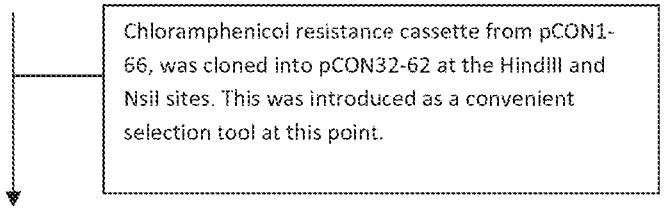

Chloramphenicol resistance cassette from pCON1-66, was cloned into pCON32-62 at the HindIII and NsiI sites. This was introduced as a convenient selection tool at this point.

pCON32-65

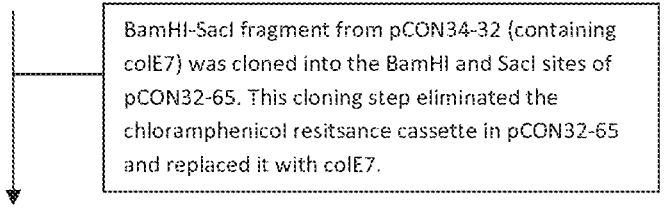

BamHI-SacI fragment from pCON34-32 (containing colE7) was cloned into the BamHI and SacI sites of pCON32-65. This cloning step eliminated the chloramphenicol resitsance cassette in pCON32-65 and replaced it with colE7.

pCON37-9

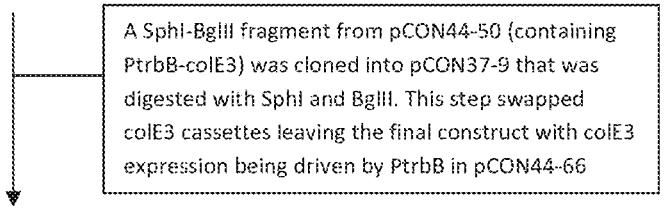

A SphI-BglII fragment from pCON44-50 (containing PtrbB-colE3) was cloned into pCON37-9 that was digested with SphI and BglII. This step swapped colE3 cassettes leaving the final construct with colE3 expression being driven by PtrbB in pCON44-66 pCON44-66 pCON44-66- This is the vector that contains the colE3-aroA-colE7 "killing cassette". The colE3-aroA-colE7 cassette gets added to pCON42-31 at the SacI and PstI sites thereby eliminating the AmpR and f1 origin in the final pCON44-74 plasmid.

GENERATION OF DONOR KILLER VECTOR pCON42-31 (backbone vector) + colE3-aroA-colE7 "killing cassette" from pCON44-66

The SacI-PstI fragment from pCON44-66 (containing the colE3-aroA-colE7 killing cassette) was cloned into pCON42-31 that was digested with SacI and PstI. This step replaced the ampR and f1 origin in pCON42-31 with the colE3-aroA-colE7 killing cassette from pCON44-66.

pCON44-74

A.

Recovered pathogen (*P. aeruginosa* MAKI) from muscle punches after treatments

B.

Recovered pathogen (*P. aeruginosa* MAKI) from spleen tissue after treatments

A.

Recovered pathogen (*P. aeruginosa* MAKI) from muscle punches after treatments

B.

Recovered pathogen (*P. aeruginosa* MAKI) from spleen tissue after treatments

A.

Recovered pathogen (*P. aeruginosa* MAKI) from muscle punches after treatments

B.

Recovered pathogen (*P. aeruginosa* MAKI) from spleen tissue after treatments

A.

Recovered pathogen (*P. aeruginosa* MAKI) from muscle punches after treatments

B.

Recovered pathogen (*P. aeruginosa* MAKI) from spleen tissue after treatments

Recovered pathogen (*P. aeruginosa* MAKI) from surgically removed eschars or muscle punches after different treatments in the experimental treatment model.

Recovered pathogen (*P. aeruginosa* MAKI) from muscle punches after different treatments

A.

B.

C.

D.

E.

A.

B.

A.

B.

A.

B.

A.

B.

C.

A.

B.

A.

B.

C.

METHODS AND COMPOSITIONS FOR GROWTH, STORAGE, AND USE OF BACTERIAL PREPARATIONS FOR WOUND AND SURFACE TREATMENTS

The present application claims priority to U.S. Provisional Application Ser. No. 62/096,980, filed Dec. 26, 2014, which is incorporated herein by reference.

FIELD OF THE INVENTION

The present invention relates to the field of bacteriology. In particular, the invention relates to novel compositions (e.g., antimicrobial agents) and methods of using the same for treating tissue (e.g., lesions of the skin and other soft-tissues). In some embodiments, the present invention comprises the killing or altering (e.g., inhibiting) growth and virulence of populations of microorganisms.

BACKGROUND OF THE INVENTION

The spread of antibiotic resistance in pathogens such as the "ESKAPE" pathogens, (*Enterococcus faecium, Staphylococcus aureus, Klebsiella pneumoniae, Acinetobacter baumanii, Pseudomonas aeruginosa*, and *Enterobacter* species) has made the treatment of infections, especially skin and soft-tissue infections, increasingly difficult (H. Boucher, et al., Clin Infect Dis. (2009) 48 (1): 1-12.).

For example, one of the persistent problems of burn wound care is the development of microbial infections. Humans live not in a sterile environment but in a symbiotic relationship with bacteria and other microbes. The intact skin and mucosal surface act to maintain a delicate balance between our tissues and the bacterial populations. Any breach in the skin or mucosal barriers alters this balance and thus has the potential to initiate infections by allowing bacteria to gain access to the underlying tissues and achieve critical numbers. One of the major treatment goals of a burn surgeon is to prevent infections and, if contamination occurs, the goal is to reduce the microbial contamination below the critical numbers required to initiate and spread infections. With the discovery of antibiotics, burn wound infections appeared to be under control. However, it has been discovered that bacteria are able to, and indeed have, overcome the antibiotics through development of resistance. Emergence of resistant strains of bacteria has become the major source of many hospital-based infections and has posed a major clinical dilemma to burn surgeons.

The problem of antibiotic resistance affects all kinds of bacterial infections, including but not limited to infections of the skin and soft-tissues. There are many examples of the rampant rise in antibiotic resistance in pathogenic organisms. In one hospital in Corpus Christi, Tex., community-acquired methicillin-resistant *Staphylococcus aureus* (MRSA), most often seen in skin and soft-tissue infections, slowly increased from 3% in 1990 to 10% in 1999 and then rapidly increased over a 4-year period to 62% in 2003 (Goodman, J Clin Invest 114, 1181 (2004)). In a Miami hospital, *P. aeruginosa* resistance to quinolones in leg ulcers increased from 19% in 1992 to 56% in 2001 (Valencia et al., J Am Acad Dermatol 50, 845-9 (2004)). There is no debate in the field; new treatments are needed to control these infections.

Prophylactic use of antibacterial agents such as silver nitrate, silver sulfadiazine (Silverdene, Thermazine, Flamazine) and mafenide acetate (Sulfamylon) has become the standard of care to reduce bacterial colonization in wounds such as burn wounds. However, these agents have limitations. For example, Silverdene has been shown to retard wound healing and cannot be used in patients who are allergic to sulfa drugs. The metabolic products of Sulfamylon are potent inhibitors of carbonic anhydrase and therefore can cause metabolic acidosis. Use of this compound is particularly contraindicated in patients who have suffered inhalation injury and those who developed sepsis.

Other antimicrobial agents that are used to prevent or reduce bacterial colonization are Gentamicin sulfate, Bacitracin, and Nitrofurantoin. Unfortunately constant use of these antimicrobial agents results in the emergence of resistant strains of the offending bacteria.

Despite the acceptance of these antimicrobial strategies as standard of care in the treatment of burn patients, development of drug resistant bacterial infections continues to pose significant clinical problems in patients (e.g., critically injured burn patients or diabetic patients with chronic ulcers) during prolonged hospitalization.

Thus, a great need exists to develop alternative strategies of antimicrobial treatment. In particular, treatments are needed that can address and effectively kill or attenuate drug-resistant microorganisms.

SUMMARY OF THE INVENTION

The present invention relates to the field of bacteriology and pharmacology. In particular, the invention relates to novel compositions (e.g., antimicrobial agents) and methods of using the same for treating tissue (e.g., lesions of the skin and other soft tissues) comprising the killing or altering (e.g., inhibiting) growth and virulence of populations of microorganisms. In particular, the technology provides compositions for applying an effective dose of non-dividing bacterial cells that prevent and/or treat infection by conjugative transmission of a plasmid that is toxic to recipient pathogen cells.

Conjugation for transferring genetic material from a donor cell into a target recipient cell for a variety of purposes has been described. See, e.g., PCT Publication WO 02/18605, U.S. Patent Application Ser. No. 20040137002, and U.S. patent application Ser. No. 10/884,257, each incorporated herein by reference in its entirety for all purposes. The present invention makes use of conjugative transfer to alter the cellular functions of a recipient cell, e.g., to kill or impair the target cell.

The technology relates to compositions and methods for culturing the donor bacteria in a manner that stably maintains the transmissible plasmid, and for storing the donor bacteria in a manner that maintains both the viability and the killing ability of the donor bacteria. The technology further relates to methods for using the donor bacteria in treatments under conditions in which the bacteria cannot further propagate (i.e., cannot divide), but in which the killing activity is maintained.

In some embodiments, the technology provides a recombinant plasmid that is not self-transmissible, and that can be stability maintained in donor bacterial cell preparations. In certain embodiments, the plasmid is pCON44-74, which is described in detail hereinbelow.

In some embodiments, the technology provides a donor bacterial cell, e.g., a live bacterium, or a minicell, a maxicell, or a non-dividing cell. In some preferred embodiments, the donor cell comprises one or more transfer genes conferring upon it the ability to conjugatively transfer the transmissible plasmid to a recipient cell, and further comprises a mutation in a gene that renders the donor bacterial cell auxotrophic for a compound, e.g., a nutrient, an amino acid, etc., such that a growth medium must be supplemented with the missing compound for the bacterial cells to replicate. In certain preferred embodiments, the donor bacterial cell is auxotrophic for one or more aromatic amino acids, 2,6-diaminopimelic acid, and/or lysine.

The donor bacterial cells are not limited to one particular genus. In some embodiments, the donor bacterial cell is selected from the group consisting of *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira,* and *Chlamydiae.* In preferred embodiments the donor bacterial cell is *E. coli,* and in particularly preferred embodiments, the donor bacterial cell is *E. coli* CON31-85A. In some embodiments, the donor bacterial cell is a minicell, a maxicell, or a non-dividing cell.

The technology comprises compositions comprising a donor bacterial cell as described above. In some embodiments, the composition comprises a growth medium devoid of aromatic amino acids, while in other embodiments, the composition comprises a growth medium supplemented with a compound. In some embodiments, the composition comprises a growth medium lacking one or more of tyrosine, tryptophan and phenylalanine, p-aminobenzoate and p-hydroxybenzoate. In some preferred embodiments, the growth medium is a minimal medium supplemented with 2,6-diaminopimelic acid and lysine.

In some embodiments, compositions of the invention comprise donor bacterial cells grown under controlled conditions for optimal growth. For example, in some embodiments, cells are grown in conditions in which the pH is controlled. In preferred embodiments, the pH of the composition is pH 7. In some embodiments, the amount of dissolved oxygen in the composition is controlled. For example, in some embodiments, the composition is maintained under conditions that maintain dissolved oxygen at about 50%.

In some embodiments, a composition comprising a donor bacterial cell comprises or consists of a buffer. In preferred embodiments, the buffer comprises a phosphate buffer, and in particularly preferred embodiments, the phosphate buffer comprises sodium phosphate and/or potassium phosphate. In some embodiments, the composition comprises an excipient mixture, e.g., for storing or freezing the cells, and comprising a protective agent and a buffer, and optionally also comprising a gelling agent. The composition may comprise one or several protective agents, with exemplary protective agents including, e.g., non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride. In certain preferred embodiments, the protective agent comprises one or more of trehalose, sucrose, and/or glucose.

A number of different gelling agents are known. For example, in some embodiments the composition comprises one or more gelling agents selected from the group consisting of hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer.

In certain preferred embodiments, the composition comprising a donor bacterial cell of the invention is in a composition of 10% (w:v) trehalose and 2.0% (w:v) glycerol in 50 mM potassium phosphate buffer. In some embodiments, this composition further comprises 0.5% (w:v) hydroxyethylcellulose.

It is contemplated that compositions of the donor bacterial cells as described above may be in any form that maintains viability, including, e.g., liquid, gel, frozen, or freeze-dried forms. For example, in some embodiments, the composition is formed by addition of water or a buffer to a freeze dried preparation, which may contain the donor bacterial cells and one or more of buffer components, protective agents, and/or gelling agents. In certain preferred embodiments, a composition is a fluid or gel containing between about $5\times10^8$ to $5\times10^{10}$ donor bacterial cells (cfu) per ml, preferably $1\times10^9$ to $1\times10^{10}$ cfu per ml, e.g., configured for therapeutic use, while in other embodiments, the composition comprises a fluid or gel containing less than about $1\times10^9$ cfu/ml, e.g., configured for short term storage.

The technology provides methods for using the compositions of the technology, e.g., donor bacterial cells comprising a transmissible bacteriocidal plasmid such as pCON44-74, for example, the composition GN-4474. In some embodiments the technology provides methods of treating a tissue surface comprising applying the composition to a surface on said tissue, and ins some embodiments, covering the tissue surface after the applying the composition, e.g., with a bandage, gauze, fabric, compress, etc.

The compositions and methods find use in the treatment of tissue having a lesion. Lesions include, e.g., burns, cuts, abrasions, abscesses, carbuncles, ulcers, furuncles, blisters, etc. The technology finds particular use in application to tissue comprising epithelial tissue.

The technology is not limited to particular manners of application. For example, in some embodiments, applying a composition of the invention to a tissue comprises soaking, washing, or rinsing a tissue in the composition. In some embodiments, the composition is applied by a process comprising applying the composition to a medical device; and contacting said medical device to the tissue to be treated.

Treatments are not limited to any particular protocol or schedule for application. For example, in some embodiments, treating comprises applying the composition to a tissue a single time, while in some embodiments, the application comprises applying the composition to a tissue a plurality of times, e.g., at regularly scheduled intervals. Intervals of time between applications are not limited to particular lengths. For example, in some embodiments, the intervals are between 1 hour and 24 hours in length, while in some embodiments, the intervals are 4 hours in length. The time intervals in a schedule of treatment may be the same length or different lengths. In certain preferred embodiments, a plurality of applications comprises at least three applications.

The technology provides methods of treating established bacterial infections, e.g., on a tissue, and of treating a tissue to prevent infection. In some embodiments, a method of treating a bacterial infection of a tissue lesion, comprises applying a composition comprising a donor bacterial cell comprising, e.g., pCON44-74, to an infected lesion in an amount of at least 5×10$^9$ cfu per 20 mm$^2$ of tissue area. In preferred embodiments, the treatment is repeated at least once, preferably twice, more preferably three times at regular intervals, e.g., intervals between about 1 hour and 24 hours in length. In certain preferred embodiments, treatments are applied at 4-hour intervals.

The technology provides methods for preparing and storing bacterial donor cells of the technology. In some embodiments, the method is directed to preparations configured for short term storage, e.g., at 4° C., the method comprising:
 a) providing a bacterial donor cell, said bacterial donor cell comprising:
  i) a recombinant transmissible plasmid comprising:
   1) a gene encoding at least one bactericidal protein operably linked to a promoter such that said plasmid is configured to express said gene encoding a bactericidal protein in a recipient cell;
   2) a selectable marker;
  ii) a gene encoding at least one immunity protein operably linked to a promoter such that said at least one immunity protein is expressed in said bacterial donor cell, wherein said at least one immunity protein inhibits said at least one bactericidal protein;
  iii) a mutation in a gene that renders the donor bacterial cell auxotrophic for a compound;
  iv) one or more transfer genes conferring on said donor bacterial cell the ability to conjugatively transfer said recombinant transmissible plasmid to a recipient cell,
 b) preparing a culture from the donor bacterial cell in a growth medium supplemented with the compound under conditions that select for said selectable marker;
 c) separating donor bacterial cells from the growth medium to produce collected donor bacterial cells;
 d) resuspending the collected donor bacterial cells at a concentration of less than 1×10$^9$ cfu per ml in a storage medium, wherein said storage medium is selected from the group consisting of: a solution comprising trehalose and/or sucrose; a solution comprising a phosphate buffer selected from sodium phosphate or potassium phosphate; and supplemented or unsupplemented M9 medium;
 the method further comprising:
 e) storing the collected donor bacterial cells in said storage medium under refrigeration, preferably at about 4° C., for up to 14 days.

In certain preferred embodiments, the storage medium further comprises glycerol, and n particularly preferred embodiments, storage medium comprises 50 mM KPO$_4$ buffer, 10% (w:v) trehalose and 2% (w:v) glycerol. In some embodiments, the storage medium further comprises 0.5% hydroxyethyl cellulose.

In some embodiments, recombinant transmissible plasmid is pCON44-74 and/or the bacterial donor cell is an *E. coli* cell. In certain preferred embodiments, the *E. coli* cell is *E. coli* CON31-85A and the growth medium is supplemented with 2,6-diaminopimelic acid and lysine.

In some embodiments, the technology provides a method of preparing a frozen composition of bacterial donor cells for therapeutic use without further culturing, comprising:
 a) providing a bacterial donor cell, said bacterial donor cell comprising:
  i) a recombinant transmissible plasmid comprising:
   1) a gene encoding at least one bactericidal protein operably linked to a promoter such that said plasmid is configured to express said gene encoding a bactericidal protein in a recipient cell;
   2) a selectable marker;
  ii) a gene encoding at least one immunity protein operably linked to a promoter such that said at least one immunity protein is expressed in said bacterial donor cell, wherein said at least one immunity protein inhibits said at least one bactericidal protein;
  iii) a mutation in a gene that renders the donor bacterial cell auxotrophic for a compound;
 b) preparing a culture from the donor bacterial cell in a growth medium supplemented with said compound under conditions that select for the selectable marker;
 c) separating the donor bacterial cells from said culture medium to produce collected donor bacterial cells; and
 d) resuspending the collected donor bacterial cells at a concentration of at least 1×10$^{10}$ cfu per ml in an excipient medium, wherein said excipient medium comprises trehalose and/or sucrose and glycerol; and
 e) snap-freezing the collected donor bacterial cells in the storage medium.

Preferably, snap freezing is conducted at a temperature of less than 45° C., preferably less than −50° C., −60° C., −70° C. or −80° C.

In certain preferred embodiments, the excipient medium comprises between about 1% and 2% (w:v) glycerol, and in particularly preferred embodiments, the excipient medium comprises 50 mM KPO$_4$ buffer, pH 7, 10% (w:v) trehalose and 2% (w:v) glycerol. In some embodiments, the excipient medium further comprises a gelling agent, e.g., about 0.5% (w:v) hydroxyethyl cellulose.

DESCRIPTION OF THE DRAWINGS

FIGS. 25A and 25 B show the effects of short term storage on viability and conjugation efficiency of GN-4474. FIG. 25 A shows the viability of GN-4474 following storage in spent M9 culture medium, in the WAVE reactor bag, at 4° C. from 0 to 80 hours. FIG. 25 B shows the effect of storage for 24 h or 72 h (mM9 culture medium, in the WAVE bag, at 4° C.), on in vitro killing efficiency.

FIG. 26A shows the viability of GN-4474 following storage in excipient buffer at 4° C. Bacteria were concentrated and resuspended in excipient buffer to various concentrations as described in the Example 7. FIG. 26B shows in vitro killing efficiency of the same GN-4474 samples.

FIGS. 27A and 27 B show the effects of different storage media for 4° C. storage on viability and conjugation efficiency of GN-4474. Bacteria were left in the Cultibag or transferred to sterile conical tubes, pelleted, and resuspended in either spent medium or in lyophilization excipient buffer without the HEC gelling agent prior to storage at 4° C. At various time points, bacteria were removed from each storage condition, diluted, and plated onto LB+Dap plates to quantify viable bacteria (FIG. 27A). FIG. 27B shows the trends for conjugation-based killing efficiency of GN-4474 stored in various media at 4° C.

FIG. 28A shows viability expressed as CFUs/ml of "controlled frozen" samples of GN-4474 in excipient buffer after storage at −20° C. over time. FIG. 28B shows killing efficiency expressed as average CFUs/ml of PA14 recovered after treatment with positive control, negative control or "controlled frozen" samples of GN-4474, and FIG. 28C shows killing efficiency expressed as PA14 percent survival after treatment with positive control, negative control or "controlled frozen" samples of GN-4474.

FIG. 29A shows viability expressed as CFUs/ml GN-4474. FIG. 29B shows killing efficiency expressed as average CFUs/ml of PA14 recovered after treatment with positive control, negative control or "snap frozen" samples of GN-4474, FIG. 30A shows viability expressed as CFUs/ml GN-4474. FIG. 30B shows killing efficiency expressed as average CFUs/ml of PA14 recovered after treatment with positive control, negative control or "snap frozen" samples of GN-4474, and FIG. 30C shows killing efficiency expressed as PA14 percent survival after treatment with positive control, negative control or "snap frozen" samples of GN-4474.

DEFINITIONS

Figure 1:
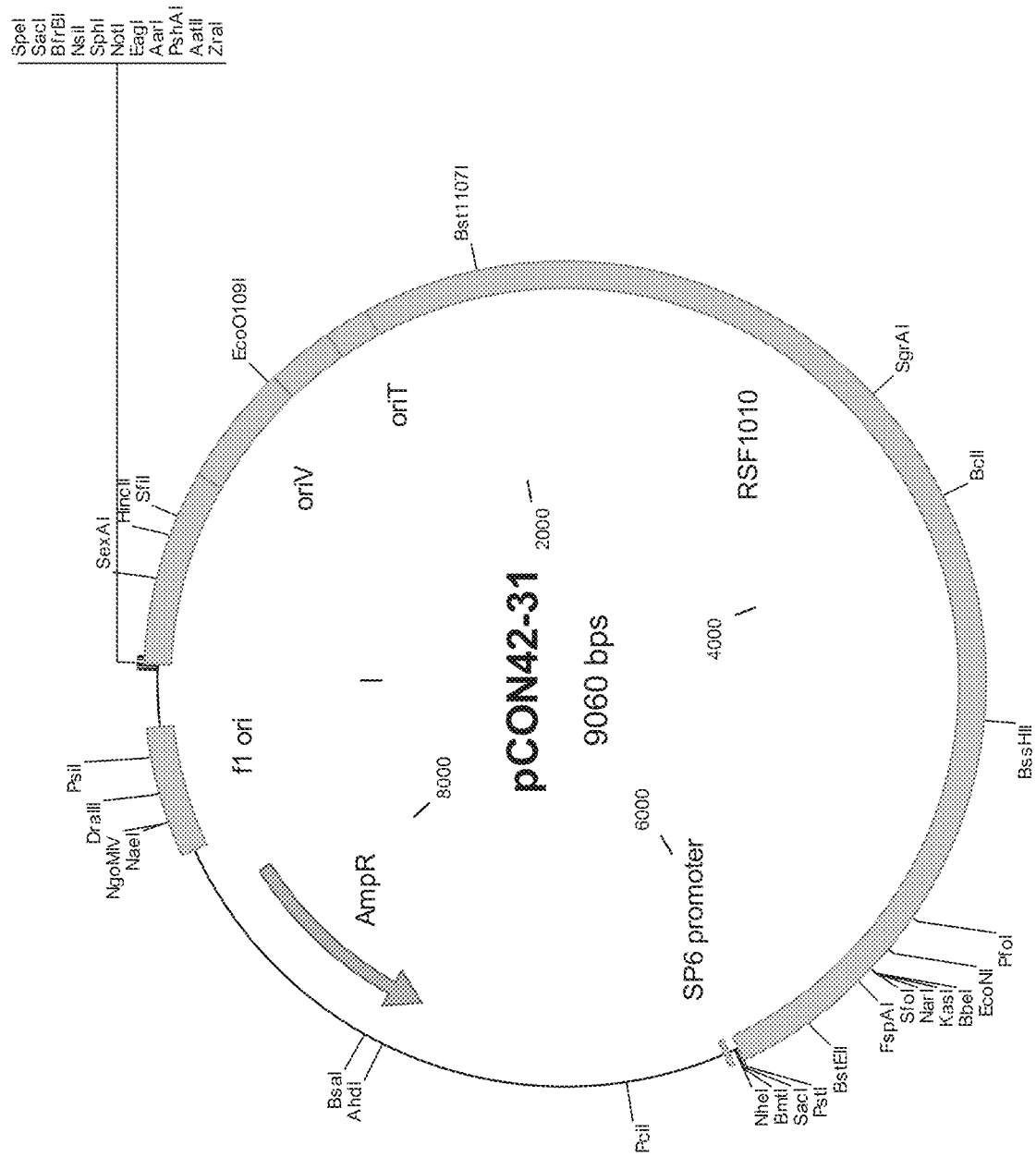
FIG. 1 is a flow diagram describing the generation of an exemplary backbone vector, and provides a plasmid map of backbone vector pCON42-31.

To facilitate an understanding of the present invention, a number of terms and phrases are defined below:

As used herein, the term "subject" refers to individuals (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of donor cell, and optionally one or more other agents) for a condition characterized by the presence of pathogenic bacteria, or in anticipation of possible exposure to pathogenic bacteria.

The term "diagnosed," as used herein, refers to the recognition of a disease (e.g., caused by the presence of pathogenic bacteria) by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "conjugation" refers to the process of DNA transfer from one cell to another. Conjugation is mediated by complex cellular machinery, and essential protein components are often encoded as a series of genes in a plasmid (e.g., the tra genes for plasmid RK2). Some of these gene products are assembled to facilitate a direct cell-cell interaction (e.g., mating pair formation), and some of them serve to transfer DNA and associated protein molecules, and to replicate the DNA molecule (e.g., DNA transfer/replication). oriT is a DNA sequence from which the transfer of a DNA molecule initiates in the process of conjugation. Conjugative transfer is a phenomenon that occurs across bacterial species and a broad host range of conjugative transfer systems that can be utilized in both Gram-positive and Gram-negative genera are known.

All well-characterized bacterial conjugative systems are grouped together into the type IV secretion system (TIVSS). The proteins required for conjugal transfer fall into three groups. Mobilization proteins (Mob and nickase, which, when in complex with a DNA molecule, are frequently referred to as the "relaxosome") bind specifically to their cognate oriTs and produce a nick in the DNA from which the conjugal transfer begins. Transfer proteins (Tra) form a multi-protein complex called the mating pair formation apparatus (Mpf) that, among other transport-related activities, is needed for formation of pili, and for their extrusion to the cell surface. Tra proteins need not be encoded on the same plasmid as the oriT on which they act. They can facilitate the transfer of plasmids that contain unrelated oriTs, provided those plasmids also contain the cognate relaxosomes.

Once plasmid DNA is prepared for transfer, it is transported through the donor's cytoplasmic membrane and into the recipient. While not limiting the technology to any particular mechanism of action it is generally believed that DNA crosses the donor membrane with the aid of a coupling protein, so-called because it couples plasmid DNA processing to a TIVSS. Free-living (planktonic), as well as surface-bound Gram-negative bacteria are capable of transferring plasmids and one of the few diversifying elements in conjugation systems is the type of pili produced and used to facilitate conjugation. Some pili are thick and flexible while others are long and rigid. Pili have the remarkable ability to retract, allowing them to promote intimate associations of cell surfaces over extended areas, which stabilize mating pairs against shearing forces.

Some well-studied Gram-positive conjugation systems employ a different strategy to bring plasmid donors into contact with potential recipients. Rather than using pili, small molecules called pheromones are known (e.g. pCF10) to facilitate cell-to-cell contact. These pheromones are typically peptides of seven or eight amino acids and are secreted in miniscule amounts, with as little as 1 to 10 molecules per donor needed to initiate the mating process. A given pheromone specifically activates the conjugative transfer system of a particular plasmid type. When a plasmid is acquired, secretion of the related pheromone is prevented, while unrelated pheromones continue to be produced to 'seduce' other potential donor cells. The capacity of several plasmids to produce a surface-exposed aggregation protein (in vitro and in vivo) in response to pheromones expressed during conjugation has been well established and, in the case of *Enterococcus faecalis*, functionally connected to the pathology of the plasmid-bearing organism.

In some plasmids, transfer functions are naturally up-regulated. Remarkably, those de-repressed plasmid systems are able to sustain conjugative DNA transfer with close to 100% efficiency (e.g., Gram-negative F and Gram-positive pCF10 plasmids). Conjugation typically occurs within aggregates of multiple donor and recipient cells; in some cases twenty and in other cases thousands of aggregated and conjugating cells were observed. While Gram-positive and Gram-negative bacteria use different methods in nature to prepare for conjugation, the conjugation that occurs is the same for all types of bacteria. Thus, the conjugative transfer of a bactericidal killer plasmid as a mechanism for killing bacteria can be used with all conjugating bacteria.

Conjugation also takes place from bacterial cells to higher and lower eukaryote cells (Waters, Nat Genet. 29:375-376 (2001); Nishikawa et al., Jpn J Genet. 65:323-334 (1990)). Trans-kingdom conjugation, such as from bacteria into mammalian and yeast cells, is well known. See, e.g., Bates et al., J Bacteriol 180, 6538-6543 (1998); Waters, Nat Genet 29, 375-376 (December, 2001).

As used herein, the terms "conjugation donor" and "donor cell" are used interchangeably to refer to a cell, e.g., a bacterial cell, carrying a plasmid, wherein said plasmid can be transferred to another cell through conjugation. Examples of donor cells include, but are not limited to E. coli strains that contain a self-transmissible plasmid or a non-self-transmissible plasmid. A cell receiving a plasmid or other cellular material from a donor cell via conjugative transfer is referred to as a "recipient cell". As used herein, the term "transmissible plasmid" refers to a plasmid that can be transferred from a donor cell to a recipient cell via conjugation.

As used herein, the term "self-transmissible plasmid" refers to a plasmid encoding all the genes needed to mediate conjugation. A recipient of a self-transmissible plasmid becomes a proficient donor to further transfer the self-transmissible plasmid to another recipient cell.

As used herein, the term "non-self-transmissible plasmid" or "mobilizable plasmid" refers to a plasmid lacking some of the genes needed to mediate conjugation. A cell carrying a non-self-transmissible plasmid does not transfer DNA through conjugation unless the missing gene(s) are supplied in trans within the same cell. Therefore, a recipient cell that lacks the missing gene(s), does not become a proficient conjugation donor when it receives the non-self-transmissible plasmid.

As used herein, the term "origin of transfer" or "oriT" refers to the cis-acting site required for DNA transfer, and integration of an oriT sequence into a non-transmissible plasmid converts it into a mobilizable plasmid (Lanka and Wilkins, Annu Rev Biochem, 64:141-169 (1995)).

In some embodiments, a donor cell is a bacterial cell (e.g., a Gram-positive or Gram-negative bacterium). Examples of donor cells include, but are not limited to, bacterial cells of a genus of bacteria, selected from the group comprising Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pedicoccus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira, and Chlamydiae.

In some embodiments, a donor cell is a non-viable cell, including but not limited to a bacterial minicell, a maxicell, or a non-dividing cell.

As used herein, the term "maxicell" refers to the cells that have been treated to maximize chromosomal degradation, e.g., by UV irradiation and extended incubation. Maxicells contain mostly plasmid DNA, and synthesis of proteins within maxicells occurs essentially exclusively from the plasmid DNA in the cells.

As used herein, the term "non-dividing cell" or "ND cell" refers to cells that are treated in a manner selected to preferentially damage the chromosomal DNA of the cell (e.g., by UV or other irradiation), wherein said cells are further treated, e.g., by rapid chilling after DNA damaging treatment, to minimize chromosomal degradation. "ND cells" can also be obtained in a process such as temporal expression of bactericidal protein (e.g., ColE3) within a donor bacterium. Thus, in some embodiments, induction of proteins (e.g., ColE3) destroys the protein synthesis in the cell, leading to cell death while leaving the conjugation apparatus and chromosomal DNA synthesized prior to ColE3 synthesis intact. ND cells contain both chromosomal and plasmid DNA but the function of the cell is sufficiently altered, e.g., by UV irradiation, that said ND cells have little or no capability to divide.

The terms "target cells," "targets," "recipient cells," and "recipients" are used interchangeably herein. In preferred embodiments, the target cells for the compositions and methods of the present invention include, but are not limited to, microorganisms such as pathogenic organisms (e.g., pathogenic bacteria) that can receive material from a donor cell via conjugative transfer. Pathogenic bacteria include, but are not limited to, Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pedicoccus, Bacillus, Corynebacterium, Arcanobacterium, Actinomyces, Rhodococcus, Listeria, Erysipelothrix, Gardnerella, Neisseria, Campylobacter, Arcobacter, Wolinella Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Acidaminococcus, Megasphaera, Veilonella, Norcardia, Actinomadura, Norcardiopsis,

*Streptomyces, Micropolysporas, Thermoactinomycetes, Mycobacterium, Treponema, Borrelia, Leptospira,* and *Chlamydiae*. In some embodiments, target cells are continuously cultured cells. In some embodiments, target cells are uncultured cells existing in their natural environment (e.g., at the site of a wound or infection) or obtained from patient tissues (e.g., via a biopsy). In preferred embodiment, target cells exhibit pathological growth or proliferation.

As used herein, the term "virulence" refers to the degree of pathogenicity of a microorganism, e.g., as indicated by the severity of the disease produced or its ability to invade the tissues of a subject. It is generally measured experimentally by the median lethal dose ($LD_{50}$) or median infective dose ($ID_{50}$). The term may also be used to refer to the competence of any infectious agent to produce pathologic effects.

The term "killer gene" refers to a gene that, upon expression in a susceptible cell, produces a product that kills the cell.

The term "killer plasmid" refers to plasmid comprising and configured to express one or more killer genes.

As used herein, the terms "attenuate" and "attenuation" as used herein in reference to a feature e.g., of a recipient or target cell, refers to a reducing or weakening of that feature, or a reducing of the effect(s) of that feature. For example, when used in reference to a pathogen or the pathogenicity of a target cell, attenuation generally refers to a reduction in the virulence of the pathogen. Attenuation of a pathogen is not limited to any particular mechanism of reduced virulence. In some embodiments, reduced virulence maybe achieved, e.g., by disruption of a secretory pathway. In other embodiments, reduced virulence may be achieved by altering cellular metabolism to increase reactivity to or susceptibility to a drug, e.g., a drug that attenuates virulence of the pathogen, or that kills the pathogen. In some embodiments, attenuation refers to a feature, e.g., virulence of a population of cells. For example, in some embodiments of the present invention, a population of pathogen cells is treated, e.g., by the methods and compositions of the invention, such that the population of cells is decreased in virulence. See, for example, co-pending application Ser. No. 11/137,948, filed May 26, 2005, and PCT Application PCT/US2006/020582, each of which is incorporated herein by reference in its entirety for all purposes.

As used herein, the term "effective amount" refers to the amount of a composition (e.g., donor cells) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a physiological system (e.g., a subject or in vivo, in vitro, or ex vivo cells, tissues, and organs). Exemplary routes of administration to the human body can be through the eyes (ophthalmic), mouth (oral), skin (e.g., topical, subcutaneous, transdermal), nose (nasal), lungs (inhalant), oral mucosa (buccal), ear, by injection (e.g., intravenously, subcutaneously, intratumorally, intraperitoneally, etc.), by introduction into the intestinal tract (e.g., rectally), by introduction into the bladder, topically to the surface of the skin or mucous membranes and the like.

As used herein, the term "tissue" as used in reference to a locus of administration, refers to any epithelial tissue or layer of an epithelial tissue. For example, a skin tissue comprises the epidermis, dermis, hypodermus, and/or any portion of skin exposed, e.g., by a wound.

As used herein, the term "skin wound" and "skin lesion" are used interchangeably, and include any breach or damage to skin or to a sublayer of skin. A skin wound may include, for example, one or more of burns, cuts, abrasions, abscesses, carbuncles, ulcers, furuncles, blisters, and the like. Burns are not limited to thermal burns, by also include, e.g., chemical burns, radiation burns, etc. An abscess is a collection of pus and debris that has built up within the body. Abscesses are usually caused by bacterial infection, and can develop anywhere in the body. Abscesses in skin and soft tissue are particularly common, and have in fact become more common in recent years; standard treatment for these types of abscesses is to cut the abscess open and drain the fluids. Antibiotics are often prescribed to further limit the infection. Carbuncles and furuncles are types of abscesses that often involve infected hair follicles, with carbuncles being larger of the two. Furuncles are sometimes referred to as boils. Ulcers are defined as sores on the skin or mucous membranes that are accompanied by disintegration of tissue; ulcers can result in complete loss of the epidermis and often portions of the dermis and subcutaneous fat as well leaving these areas susceptible to bacterial infection. Decubitus ulcers (bedsores) and diabetic foot ulcers are two examples of serious ulcers that can lead to gangrene and amputation of an entire area or limb. Impetigo is a contagious skin infection caused by bacteria, most common in infants and children, that produces blisters or sores on the face, neck, hands, and diaper area; impetigo is classified as either non-bullous (crusted) and bullous (large blisters). Impetigo can be treated with topical antibiotics if the affected area is small, or oral antibiotics if the affected area is larger or if the bacteria is resistant.

As used herein, the term "treating a surface" refers to the act of exposing a surface to one or more compositions of the present invention. Methods of treating a surface include, but are not limited to, spraying, misting, submerging, and coating or covering (i.e. a bandage or gauze that was pretreated or saturated with product). As surface may be, for example, a tissue surface or the surface of a device.

As used herein, the term "bandage" as used in reference to a dressing, e.g., for covering a wound or treated area, is used broadly to refer to all medical-type dressings commonly used for wound coverage, e.g., gauze strips, gauze pads, fabrics, adhesive bandages, foam pads, hydrofibers, hydrogels, tape, etc.

As used herein, the term "co-administration" refers to the administration of at least two agent(s) (e.g., two separate donor bacteria, each comprising a different plasmid) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell (prokaryotic or eukaryotic), or a tissue as compared to the same cell or tissue prior to the administration of the toxicant.

As used herein, the term "pharmaceutical composition" refers to the combination of an active agent (e.g., donor bacteria cells) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities, e.g., the bladder, colon, intestine, esophagus, etc.,).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, dis-intrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

As used herein, the term "therapeutic agent," refers to compositions that decrease the infectivity, morbidity, or onset of mortality in a subject contacted by a pathogenic microorganism or that prevent infectivity, morbidity, or onset of mortality in a host contacted by a pathogenic microorganism. As used herein, therapeutic agents encompass agents used prophylactically, e.g., in the absence of a pathogen, in view of possible future exposure to a pathogen. Such agents may additionally comprise pharmaceutically acceptable compounds (e.g., adjuvants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.) in a host. "Pathogens" include, but are not limited to, viruses, bacteria, archaea, fungi, protozoans, *mycoplasma*, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram stain, causing the stained cells to generally appear dark blue to purple under the microscope. "Gram-negative bacteria" do not retain the primary dye used in the Gram stain, but are stained by the counterstain. Thus, Gram-negative bacteria generally appear red.

As used herein, the term "microorganism" refers to any species or type of microorganism, including but not limited to, bacteria, archaea, fungi, protozoans, *mycoplasma*, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes; etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methyl inosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA or RNA) sequence that comprises coding sequences necessary for the production of a polypeptide, precursor, or RNA (e.g., rRNA, tRNA). A polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences, or 5' flanking sequences. Sequences located 3' or downstream of the coding region and present on the mRNA are referred to as 3' non-translated sequences or 3' flanking sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into pre-mRNA; introns may contain regulatory elements such as enhancers. Introns are generally removed or "spliced out" from the primary (pre-mRNA) transcript; introns therefore are generally absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "wild-type" refers to a gene or gene product in the form that would be isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The sequence of nucleotides in the DNA thus encodes for the sequence of amino acids in the corresponding polypeptide.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript.

Alternatively, the coding region utilized in the expression vectors of the present invention may contain endogenous enhancers/promoters, splice junctions, intervening sequences, polyadenylation signals, etc. or a combination of both endogenous and exogenous control elements.

The term "homology" refers to a degree of similarity between molecules such as nucleic acid molecules. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any nucleic acid that can hybridize to either or both strands of the double-stranded nucleic acid sequence under conditions of low stringency as described above. When used in reference to a single-stranded nucleic acid sequence, the term "substantially homologous" refers to any nucleic acid that can hybridize (i.e., it is the complement of) to the complement of the single-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample. In yet another example, nucleic acids in a sample are purified by removing or reducing one or more components from a sample. Components to be reduced or removed in purification comprise other nucleic acids, damaged nucleic acids, proteins, salts, etc.

"Amino acid sequence" and terms such as "polypeptide" or "protein" are not meant to limit the amino acid sequence to the complete, native amino acid sequence associated with the recited protein molecule.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), bacterial cultures (using liquid or solid media, e.g.,) and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "transdominant negative mutant gene" refers to a gene encoding a protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

As used herein, the term "kit" refers to any delivery system for delivering materials. In the context of reaction materials such as donor cells, such delivery systems include systems that allow for the storage, transport, or delivery of reaction reagents (e.g., cells, buffers, selection reagents, etc., in the appropriate containers) and/or supporting materials (e.g., media, written instructions for performing using the materials, etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain cells for a particular use, while a second container contains selective media. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction materials needed for a particular use in a single container (e.g., in a single box housing each of the desired components). The term "kit" includes both fragmented and combined kits.

As used herein, the term "cellular metabolic function" refers to any or all processes conducted by a cell (e.g., enzymatic or chemical processes associated with cell function), other than genomic replication.

DETAILED DESCRIPTION OF THE INVENTION

The present technology is directed to bacterial donor cells usable for conjugative delivery of toxins to pathogens. The technology finds particular application in the treatment of tissue lesions, e.g., skin wounds such as burns for the prevention and treatment of infection and for the prevention of sepsis associated with infection.

Growth and storage of donor cells poses certain challenges when the cells are to be used for therapeutic purposes. For example, compositions of the present technology are configured so that during use, e.g., on a tissue wound, the probiotic organism cannot grow and it must be administered in an effective dosage that does not require further growth of the bacterial donor cells at the treatment site. As discussed herein below, concentrations of donor bacterial cells used in certain preferred embodiments, reported in cfu/ml, are typically greater than $1 \times 10^9$ cfu/ml. However, during development of the technology it was observed that overgrowth of the donor bacteria to stationary phase, or refrigeration of the donor bacteria at concentrations at or above the therapeutic range reduced the conjugation competence of the cells.

Although the disclosure herein refers to certain illustrated embodiments, it is to be understood that these embodiments are presented by way of example and not by way of limitation.

Provided herein are methods for growth and storage of donor bacterial cells in a manner that preserves viability and conjugative killing ability, while achieving preparations having donor bacteria in suitable therapeutic concentrations for direct use without further growth. Also provided are particular transmissible plasmids and donor bacteria providing stable compositions for therapeutic use, and dosing regimens for treatment or prevention of infection by a variety of bacterial pathogens.

Many types of patients being treated for lesions, e.g., skin lesions, require prolonged hospitalization, multiple surgeries, medical interventions and blood transfusions (e.g., burn victims or diabetic patients with chronic ulcers). Several studies indicate a causal relationship between the severity of trauma and surgery and the predisposition of these patients to develop sepsis (see, e.g., Angele and Faist, Crit Care 6, 298 (2002); Roumen et al., Ann Surg 218, 769 (1993)).

Unresolved sepsis leads to multi-organ failure and ultimately death. Organ failure is the leading cause of death in trauma and surgical patients. Excessive inflammatory response and depression of cell-mediated immunity predisposes these patients to infectious complications (see, e.g., Angele and Faist, Crit Care 6, 298 (2002); Faist, Curr Top Microbiol Immunol 216, 259 (1996); and Schinkel et al., J Trauma 44, 743 (1998)).

In recent years, the emergence of several multi-antibiotic-resistant bacterial strains has made the treatment of nosocomial infections in critically injured patients exceedingly difficult. The spread of antibiotic resistance in pathogens such as the "ESKAPE" pathogens, (*Enterococcus faecium, Staphylococcus aureus, Klebsiella pneumoniae, Acinetobacter baumanii, Pseudomonas aeruginosa*, and *Enterobacter* species) has made the treatment of infections, especially skin and soft-tissue infections, increasingly difficult (H. Boucher, et al., Clin Infect Dis. (2009) 48 (1): 1-12.)

Thus, in some embodiments, the present technology provides a therapeutic treatment comprising donor bacterial cells (e.g., pathogenic or non-pathogenic bacteria, non-dividing cells) comprising one or more plasmids (e.g., self-transmissible or non-self-transmissible plasmids), wherein the plasmid may be transferred (e.g., through conjugation) from the donor cell to a target/recipient cell (e.g., a pathogenic microorganism), resulting in the plasmid expressing its genetic material in the target.

In some embodiments, the technology provides a stable preparation of a bacterial cell and a transmissible killer plasmid for use, e.g., in topical treatment of skin wounds and burn infections. In particular, the technology provides a donor cell that comprises a transmissible killing plasmid termed "pCON44-74," or a variant thereof, that retains the functions required for use in the methods and applications described herein below, and depicted schematically in FIG. 3. While the use of pCON44-74 plasmid is not limited to use in a particular strain of donor cell, in embodiments discussed herein below, pCON44-74 is used with an *E. coli* donor cell. As used herein, the term "GN-4474" refers to the bacterial strain *E. coli* CON31-85A containing the pCON44-74 plasmid. Aspects of the technology are directed to methods of growing and storing GN-4474, and to formulations and treatment protocols for using GN-4474 in the prevention and treatment of infection.

Methods of storing bacterial cells by freezing, with or without lyophilization, are known but are commonly done with an expectation that reconstituted cells will be further cultured. The loss of a major portion of viable cells is tolerable when the cells will be further cultured for use. An aspect of the present technology is formulations for storage and administration that do not require further growth of the bacteria for effective use.

A. Elements of Conjugation-Based Killing Preparations

1. Transmissible Plasmids

The RK2 conjugation system possesses a set of genes that once expressed are very proficient in transferring plasmid DNA from Gram-negative bacterial hosts (e.g., *E. coli*). Thus, the functional RK2 conjugation machinery can mobilize plasmid DNA from a large number of Gram-negative bacterial hosts. It has been shown that, as long as proper vegetative replication origins are introduced, a plasmid can be mobilized from these donors (*E. coli* and other Gram-negative donors) to other Gram-negative target strains, and even Gram-positive target strains (see, e.g., Giebelhaus et al., J Bacteriol 178, 6378-6381 (1996)), generating exconjugants. Conjugation systems of the present invention are not limited to RK2, since the majority of conjugative plasmids share strong similarities, and any other system could serve as a delivery system.

a) Killer Genes

While an understanding of the mechanism is not necessary to practice the present invention and while the present invention is not limited to any particular mechanism of action, it is contemplated that, in some embodiments, donor cells comprise a transmissible plasmid that is conjugatively transferred into a target, wherein one or more products encoded by the plasmid are expressed (e.g., to make mRNA or protein) resulting in the killing of the target cells or the inhibiting of their growth. In some embodiments, the donor cells further comprise a helper plasmid. In some embodiments, the transmissible plasmid is a self-transmissible plasmid.

In some embodiments, donor cells comprise a transmissible plasmid comprising nucleic acid that encodes one or more polyamino acids (e.g., polypeptides or proteins) that are bactericidal. In preferred embodiments, donor cells further comprise nucleic acid that encodes a polyamino acid capable of neutralizing the bactericidal properties of the polyamino acid of the non-self-transmissible plasmid within the donor cells (e.g., an immunity protein; see, e.g., Examples 2 and 4). In preferred embodiments, the gene encoding the neutralizing polyamino acid is on a chromosome of the donor cell, while in other embodiments, it is on a helper plasmid. In some embodiments, the polyamino acid capable of neutralizing the bactericidal polyamino acid is under control of a constitutive promoter. In some embodiments, the polyamino acid capable of neutralizing the bactericidal polyamino acid is under control of an inducible promoter. While an understanding of the mechanism is not necessary to practice the present invention and while the present invention is not limited to any particular mechanism of action, it is contemplated that, in some embodiments, the polyamino acid capable of neutralizing bactericidal polyamino acid and the bactericidal polyamino acid form a non-toxic complex within the donor bacteria.

In some embodiments, the bactericidal polyamino acid is encoded by the colE3 gene. The present invention is not limited by the type of bactericidal gene used. Indeed a variety of bactericidal genes are contemplated including, but not limited to, colA, colB, colD, colIa, colIb, colK, colN, colE1, colE2, colE4, colE5, colE6, colE7, colE8, colE19 and a gene encoding lysozyme, lysostaphin, streptolysin, or listeriolysin O, etc. In some embodiments, the self-transmissible or non-self-transmissible plasmid comprises a promoter (e.g., the lac promoter/operator) that drives expression each of the bactericidal polyamino acid(s). In some embodiments in which a plasmid contains more than one bacteriocidal protein genes the promoters are all configured to express the toxins in the same target cell, while in other embodiments, a transmissible plasmid will be configured to express a first bacteriocidal protein if transferred to a first type of recipient cell, and to express a second bacteriocidal protein if transferred to a second type of recipient cell.

Bactericidal proteins such as colicins are not lethal only to bacteria. Although colicins are termed "bactericidal" proteins, the colicin proteins are enzymes that are universally toxic to cells, such as DNase and RNase (Bowman et al (1971) PNAS 68:964-968; Tomita et al (2000) PNAS 97:8278-8283; Schaller and Nomura (1976) PNAS 73:3989-3993).

In nature, the delivery of a bactericidal protein, such as a colicin, is typically controlled by recognition of a toxin-antidote complex on the surface of the target cell. The colicin is secreted to extracellular space by a colicin-producing bacterium as a toxin-antidote complex, and the toxin-antidote complex binds only to target cells that carry a specific surface molecule. Only the toxin molecule is imported into the target cell, killing the cell. In nature, killing by bactericidal proteins such as colicins is restricted to target cells that carry the correct surface molecule. The technology provided herein bypasses this restrictive surface-recognition step by using conjugation to deliver a DNA molecule encoding the toxin directly into the target cell, and does not require recognition of a specific surface molecule on the target cell. Thus, bactericidal toxins may be used in targeting non-bacterial cells, e.g., eukaryotic cells, using conjugative transfer.

In some embodiments, a helper plasmid encodes a repressor protein (e.g., lacI) capable of inhibiting expression of the bactericidal gene. In other embodiments a repressor protein is encoded on the chromosome of the donor strain. In some embodiments, the repressor protein is under control of a constitutive promoter. In some embodiments, the repressor protein is under control of an inducible promoter.

b) Vectors

In some embodiments, the present invention makes use of plasmids configured for the expression of extremely toxic proteins. In preferred embodiments, the vectors of the present invention comprise rrnBT1T2 transcription terminators upstream of a strong bacterial promoter. The present invention is not limited to the use of the rrnBT1T2 transcription terminators. Other known transcription terminators may be utilized.

In some embodiments, the lactose promoter and operator are utilized. In some embodiments, the LacI$^Q$ repressor protein is included on the plasmid. In other embodiments, it is provided on a separate vector, F' element, or chromosome. The present invention in not limited to the use of lactose promoter and operator. Other suitable promoters may be utilized, including, but not limited to, tetracycline, PBAD, T7, and T5 promoters.

Figure 12:
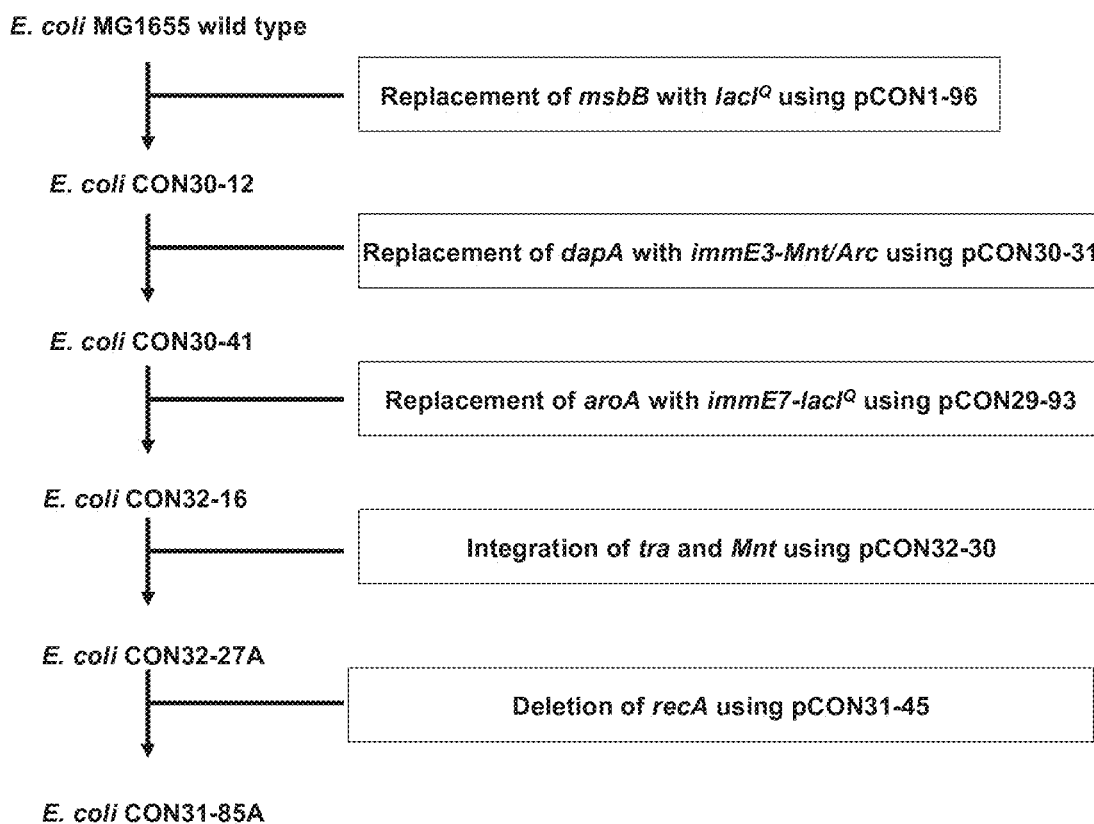
FIG. 12 shows a schematic representation for the construction of *E. coli* CON31-85A including intermediate strains and plasmids used to generate the different strains having particular genetic alterations.

In some embodiments, the present invention provides vectors comprising a hybrid promoter/operator system. One hybrid promoter/operator utilizes the Arc and Mnt repressor proteins from *Salmonella* bacteriophage P22 as basic scaffolds (see, e.g., WO 2005/072092, which is incorporated herein by reference). The Arc and Mnt repressor proteins are small transcriptional regulatory proteins with structural similarity. Both Arc and Mnt proteins contain two functional domains—a dimeric N-terminal domain that binds operator DNA and a C-terminal coiled-coil domain that mediates protein tetramerization, which is essential for function (Knight and Sauer. Proc. Natl. Acad. Sci. USA 86:797-801 {1989}) (shown in FIG. 12). Tetramerization of Arc and Mnt provide cooperative interactions that increase both the binding affinity and specificity for the operator sites (Berggrun and Sauer. Proc. Natl. Acad. Sci. USA. 98:2301-2305 {2001}). Even with this structural similarity, Arc and Mnt recognize almost completely different operator sequences with only 6 of 21 base pairs in common (Vershon et al. J Mol. Biol. 195:323-31 {1987}; Vershon et al. J. Mol. Biol. 195:311-322 {1987}).

For the promoter/repressor system used in the present technology, co-expression of two repressor proteins, the wildtype Mnt repressor and a mutant Mnt-Arc protein are utilized. The mutant Mnt-Arc proteins contain the wildtype C-terminal dimerization domain from Mnt; however, six residues within the N-terminal DNA binding domain have been replaced with the corresponding 9 residues from the Arc repressor (Knight and Sauer. Proc. Natl. Sci. USA 86:797-801 {1989}). A Mnt-Arc homodimer retains wild-type tetramerization ability, but now recognizes the Arc operator sequence (02) instead of the Mnt operator (01). The novel repressor heterotetramer of the present invention consists of one wildtype Mnt homodimer and one hybrid Mnt-Arc homodimer.

Acquisition of the Mnt and/or Arc repressors by pathogenic bacteria does not readily confer resistance to expression of toxic genes because of the following reasons: (1) The wild-type Mnt tetramer will not recognize the hybrid operator sequence. (2) The wild-type Arc tetramer will not recognize the hybrid operator sequence. (3) A Mnt-Arc protein formed by homologous recombination between acquired Arc and Mnt proteins will eliminate the wildtype copy, which is still required for repression. In addition, bacteriophage P22 is restricted to *Salmonella* species, and the chance of *E. coli* and other pathogens being exposed to the genes from this phage is less likely. The hybrid promoter/repressor system of the present invention is thus ideal for regulating the expression of genes and RNA in any bacterial species.

In additional preferred embodiments, the vectors may comprise a low copy number origin of replication (e.g., low copy modified pSC101 or RK2. Other exemplary origins of replication include, but are not limited to, wildtype pSC101, p15a, pACYC.

Plasmids finding use with the technology may also comprise a multiple cloning site for insertion of nucleic acid encoding genes of interest and a selectable marker (e.g., an antibiotic resistance gene such as kanamycin, ampicillin, tetracycline, etc.), and/or protein purification tags (e.g., His-tag, GST-tag, intein tag).

As described above, in a preferred embodiment, the donor cells of the present invention comprise an immunity protein that inhibits or neutralizes the bactericidal protein expressed by the transmissible plasmid. Numerous pairs of bactericidal proteins and corresponding immunity proteins are known in the art. In the present invention, the bactericidal proteins listed above are inhibited by the corresponding colicin A, colicin B, colicin D, colicin Ia, colicin Ib, colicin K, colicin N, colicin E1, colicin E2, colicin E3, colicin E4, colicin E5, colicin E6, colicin E7, colicin E8, and colicin E9 immunity proteins, respectively. Still other combinations of bactericidal proteins (e.g., bacteriocins) and neutralizing immunity proteins are known in the art (see, e.g., exemplary tables of bacteriocin immunity proteins on the World Wide Web site us.expasy.org/cgi-bin/get-entries?KW=Bacteriocin %20immunity, the ExPASy (Expert Protein Analysis System) proteomics server of the Swiss Institute of Bioinformatics (SIB)). In some embodiments the gene encoding an immunity protein is under control of a promoter, wherein said promoter is constitutively active, while in other embodiments, the gene encoding an immunity protein is under control of a promoter that is inducible.

A variety of self-transmissible and non-self-transmissible plasmids are contemplated in the present, invention. It is contemplated that the compositions comprising plasmids of the present invention find use in research and therapeutic applications.

2. Donor Cells a) Donor Bacteria

It is contemplated that any type of bacteria (e.g., Gram-positive and Gram-negative bacteria) can be used as donor cells in the present invention (see, e.g., Example 1). A number of approaches may be taken to prevent spread (e.g., growth) of donor bacteria. In addition to using non-dividing cells as donors (see, e.g., U.S. patent application Ser. No. 10/884,257, filed Jul. 2, 2004, herein incorporated by reference in its entirety for all purposes), several other approaches include, but are not limited to, using donors with temperature-sensitive mutations (e.g., aminoacyl-tRNA synthetase and RNase P mutations), auxotrophic mutants (e.g., dapA and aroA), serine mutations, and/or other mutations or deficiencies in amino acid synthesis. These examples are not meant to limit the scope of the invention. Those skilled in the art will immediately appreciate that there are alternative approaches that may be used to attenuate donor bacteria. These mutations have been analyzed and are known well in the art, and introduction of these mutations into a newly obtained bacterial donor is well within the capabilities of one of skill in the art.

In some embodiments, donor bacterial cells of the present invention comprise temperature sensitive mutation(s). A temperature-sensitive mutant grows abnormally within a certain range of temperature compared to its isogenic wild-type bacteria. In the mutant, a mutation in the RNA or protein causes effects, e.g., changes in conformation, that are sensitive to temperature such that mutants can be grown in a lab at their permissive temperature; however, they have severe growth defects at non-permissive (e.g., higher) temperatures (e.g., at body temperature).

Examples of these mutations include aminoacyl-tRNA synthetases (see, e.g., Sakamoto et al., J Bacteriol 186, 5899-5905 (2004); Martin et al., J Bacteriol 179, 3691-3696 (1997)), and RNase P (Li, Rna 9, 518-532 (2003); Li and Altman, Proc Natl Acad Sci USA 100, 13213-13218 (2003)). An aminoacyl-tRNA synthetase catalyzes the esterification of a specific amino acid to the 3'-terminal adenosine of the corresponding tRNA, and RNase P is an crucial ribonuclease to generate the mature 5' end of tRNAs in all organisms (Gopalan et al., J Biol Chem 277, 6759-6762 (2002). Defects in these enzymatic functions prevent protein synthesis in the cell.

In preferred embodiments of the present invention, certain features are employed in the plasmids and donor cells of the invention to minimize potential risks associated with the use of DNA or genetically modified organisms in the environment. For instance, in environmentally sensitive circumstances it may be preferable to utilize non-self-transmissible plasmids. Thus, in some embodiments, the plasmids are mobilizable by conjugative machinery but are not self-transmissible. As discussed herein, this may be accomplished in some embodiments by integrating into the host chromosome all tra genes whose products are necessary for the assembly of conjugative machinery. In such embodiments, plasmids are configured to possess only an origin of transfer (oriT). This feature prevents the recipient, before or even after it dies, from transferring the plasmid further.

Another biosafety feature comprises utilizing conjugation systems with predetermined host-ranges. As discussed above, certain elements are known to function only in few related bacteria (narrow-host-range) and others are known to function in many unrelated bacteria (broad-host-range or promiscuous) (del Solar et al., Mol. Microbiol. 32: 661-666, (1996); Zatyka and Thomas, FEMS Microbiol. Rev. 21:29 1 319, (1998)). Also, many of those conjugation systems can function in either Gram-positive or Gram-negative bacteria but generally not in both (del Solar, 1996, supra; Zatyka and Thomas, 1998, supra).

In some embodiments, donor bacterial cells of the present invention comprise auxotrophic mutant(s). There are large numbers of auxotrophic mutants known in the art. Examples of genes causing such phenotype are dapA and aroA. dapA encodes an enzyme dihydropicolinate synthase, a key enzyme for lysine biosynthesis in plant and bacteria (see, e.g., Ledwidge and Blanchard, Biochemistry 38, 3019-3024 (1999)), and aroA encodes an enzyme 5-enolpyruvylshikimate 3-phosphate synthase, catalyzing a key step in the synthesis of aromatic amino acids (see, e.g., Rogers et al., Appl Environ Microbiol 46, 37-43 (1983)). These mutants can be grown under laboratory conditions with the supplement of lacking amino acids for these bacteria. However, upon application, these mutants cannot grow well because the key nutritional factor is missing. These are but two examples, and there are many similar auxotrophic mutations known to be available to those of skill in the art.

In some embodiments, the present invention utilizes environmentally safe bacteria as donors. Safe bacteria are known in the art. For example, delivery of DNA vaccines by attenuated intracellular Gram-positive and Gram-negative bacteria has been reported (Dietrich et al., 2001 Vaccine 19, 2506-2512; Grillot-Courvalin et al., 1999 Current Opinion in Biotech. 10, 477-481). In addition, the donor strain can be one of thousands of harmless bacteria that colonize the non-sterile parts of the body (e.g., skin, gastrointestinal, urogenital, mouth, nasal passages, throat and upper airway systems). In some preferred embodiments, low virulence strains are used.

b) Non-Viable Donor Cells

In another strategy non-viable donors are utilized instead of living cells. For example, minicells and maxicells are well studied model systems of metabolically active but nonviable bacterial cells. Minicells lack chromosomal DNA and are generated by special mutant cells that undergo cell division without DNA replication. If the cell contains a multicopy plasmid, many of the minicells will contain plasmids. Minicells neither divide nor grow. However, minicells that possess conjugative plasmids are capable of conjugal replication and transfer of plasmid DNA to living recipient cells. (see, e.g., U.S. Pat. No. 4,968,619).

Maxicells are cells that are treated so as to destroy their chromosomal DNA, while retaining the function of plasmids that they contain. Maxicells can be obtained from a strain of E. coli that carries mutations in the key DNA repair pathways (recA, uvrA and phr). Because maxicells lack so many DNA repair functions, they die upon exposure to low doses of UV light. Importantly, plasmid molecules (e.g., pBR322) that do not receive UV irradiation continue to replicate. Transcription and translation (plasmid-directed) can occur efficiently under such conditions (Sancar et al., J. Bacteriol. 137: 692-693 (1979)), and the proteins made prior to irradiation should be sufficient to sustain conjugation. This is supported by the following two observations: i) that streptomycin-killed cells remain active donors, and ii) that transfer of conjugative plasmids can occur in the presence of antibiotics that prevent de novo gene expression (see, e.g., Heineman and Ankenbauer, J. Bacteriol. 175. 583-588 (1993); Cooper and Heineman, Plasmid 43, 171-175 (2000)). Accordingly, UV-treated maxicells will be able to transfer plasmid DNA to live recipients. It should also be noted that the conservation of recA and uvrA genes among bacteria should allow maxicells of donor strains other than E. coli to be obtained.

In some embodiments, the present invention utilizes non-dividing cells (e.g., a described in U.S. patent application Ser. No. 10/884,257, filed Jul. 2, 2004, incorporated herein by reference in its entirety for all purposes) as donor cells. Non-dividing cells are generally treated such that the ability to divide and grow is removed but conjugation efficiency is preserved. In preferred embodiments, non-dividing cells are treated such that chromosomal DNA is damaged but is not destroyed to the same extent as it is in the creation of maxicells.

B. Construction and Use of GN-4474 Preparations

Particular embodiments of the technology, e.g., GN-4474, can be used to treat any of these types of skin infections. One method of application would be to apply GN-4474 topically as an ointment; this method of application would be suited to infections such as impetigo. Alternatively, GN-4474 can be injected or infused directly into the infected tissue; this method of application would be particularly suited to abscesses and ulcers. Application of GN-4474 both topically and injected would be advantageous in some circumstances.

1. Construction of E. coli CON31-85A

Example 1 details the genetic modifications made to produce E. coli CON31-85A. The resulting strain has the genotype:

K-12 E. coli MG 1655 $\Delta$msbB::lacIQ, $\Delta$dapA::immE3-Arc/mnt, $\Delta$aroA::imm$\times 10^7$-lacI$^Q$, attB::tra-P$_L$-Mnt, $\Delta$recA 2. Construction of pCON44-74 Plasmid and GN-4474

Figure 2:
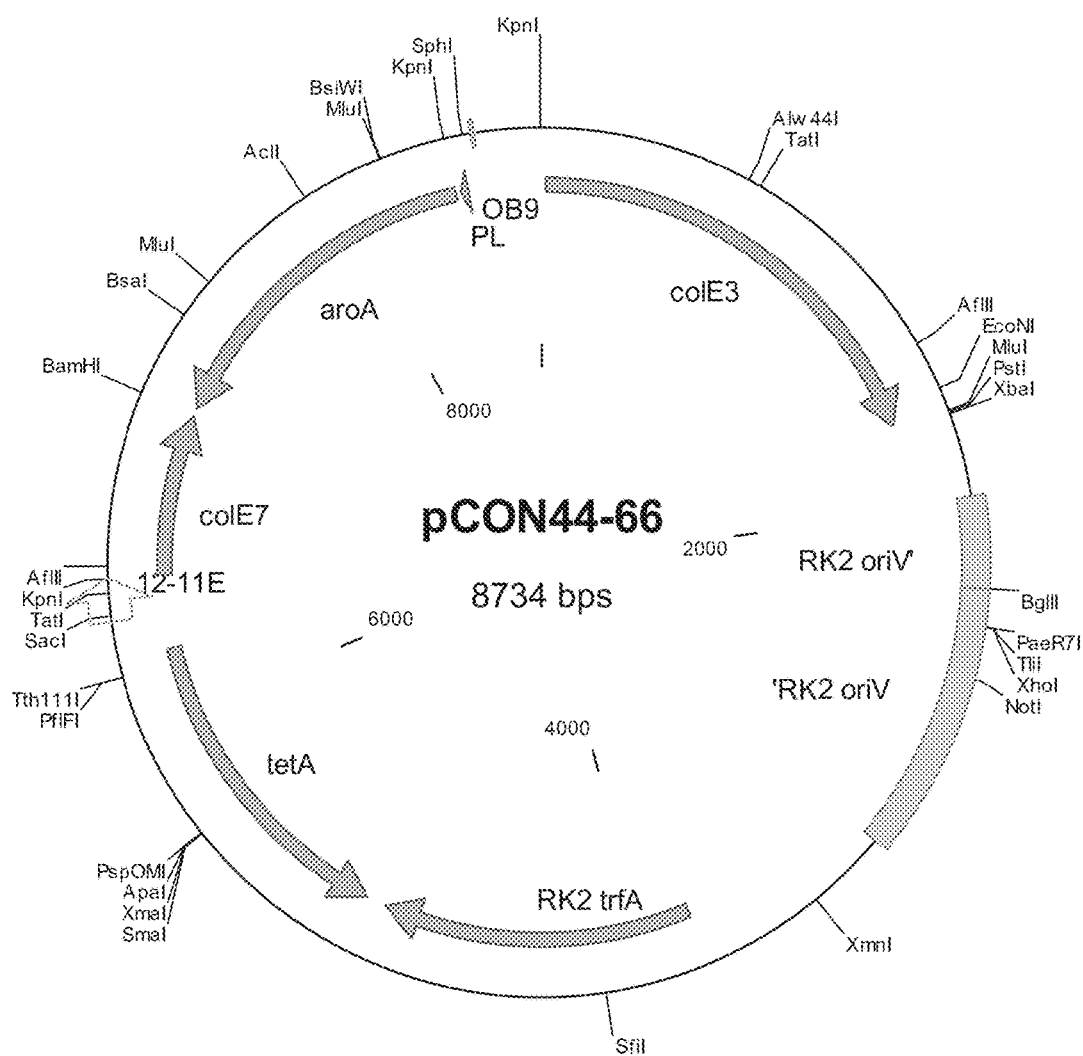
FIG. 2 is a flow diagram describing the generation of an exemplary bacteriocidal killing cassette, and provides a plasmid map of a vector containing a killing cassette, pCON44-66.
Figure 3:
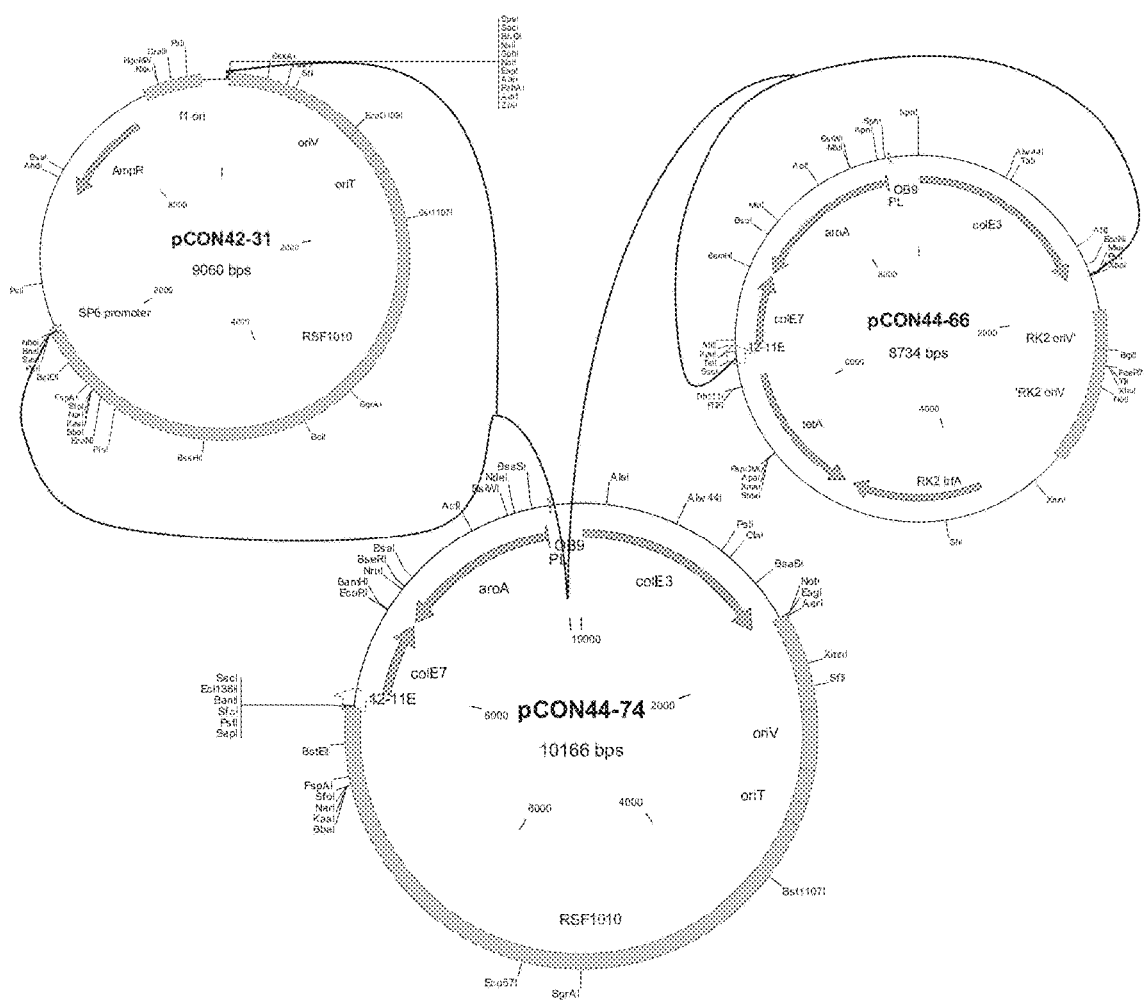
FIG. 3 is a diagram describing the generation of an exemplary bacteriocidal donor killer vector, and provides a plasmid map of a donor killer vector pCON44-74.

FIGS. 1-3 provide a detailed flow diagram of the assembly of the killing plasmid pCON44-74. The skilled person will appreciate that modifications can be made to the plasmid without altering its function in the technology, e.g., removing portions of nucleic acid that do not affect the function of the conjugation, replication, or toxin functions of the plasmid. Further, the plasmid may be transformed into different types of non-pathogenic donor cells, or variant strains of E. coli. It is contemplated that the present technology encompasses such variants of both pCON44-74 and GN-4474. See, e.g., WO 2006/128089, which is incorporated by reference herein in its entirety for all purposes.

3. Administration of GN-4474 for Prevention and Treatment of Infection

The active ingredient in GN-4474 is a harmless genetically engineered strain of E. coli that possesses conjugation machinery that can transfer "a killer plasmid" into target bacteria, that, once expressed, kills the recipient bacteria. Typically, antibiotics that are taken orally or that are injected are dosed as the amount (grams, milligrams, etc) that are given so many times per day. Topical antibiotics such as Neosporin are dosed as the number of units of each antibiotic in a particular amount (3.5 mg of neomycin, 5,000 units of polymyxin B and 400 units of bacitracin per 1.0 gram of Neosporin).

Neither measure of dosing is appropriate for a composition such as GN-4474. Using a mass or weight of the active substance, i.e., *E. coli* GN-4474 bacteria in the final formulation, to indicate dosage is not practical. Rather, the dosage indicator as used herein is colony forming units (cfus), typically indicated in relation to a volume of a formulation or a unit of area treated or to be treated.

a) Prevention Dosing: Topical

The GN-4474 composition has been shown to be effective in preventing infection when used as a preventative, i.e., when applied at the same time as exposure to a pathogen. It was demonstrated that when infecting burned mice with between $1\times10^4$ and $1\times10^5$ cfu of pathogen (*P. aeruginosa* or *Acinetobacter baumannii*) a dose response for GN-4474 is observed that prevents death in the mice and also will clear the pathogen from the burn site.

Figure 23:
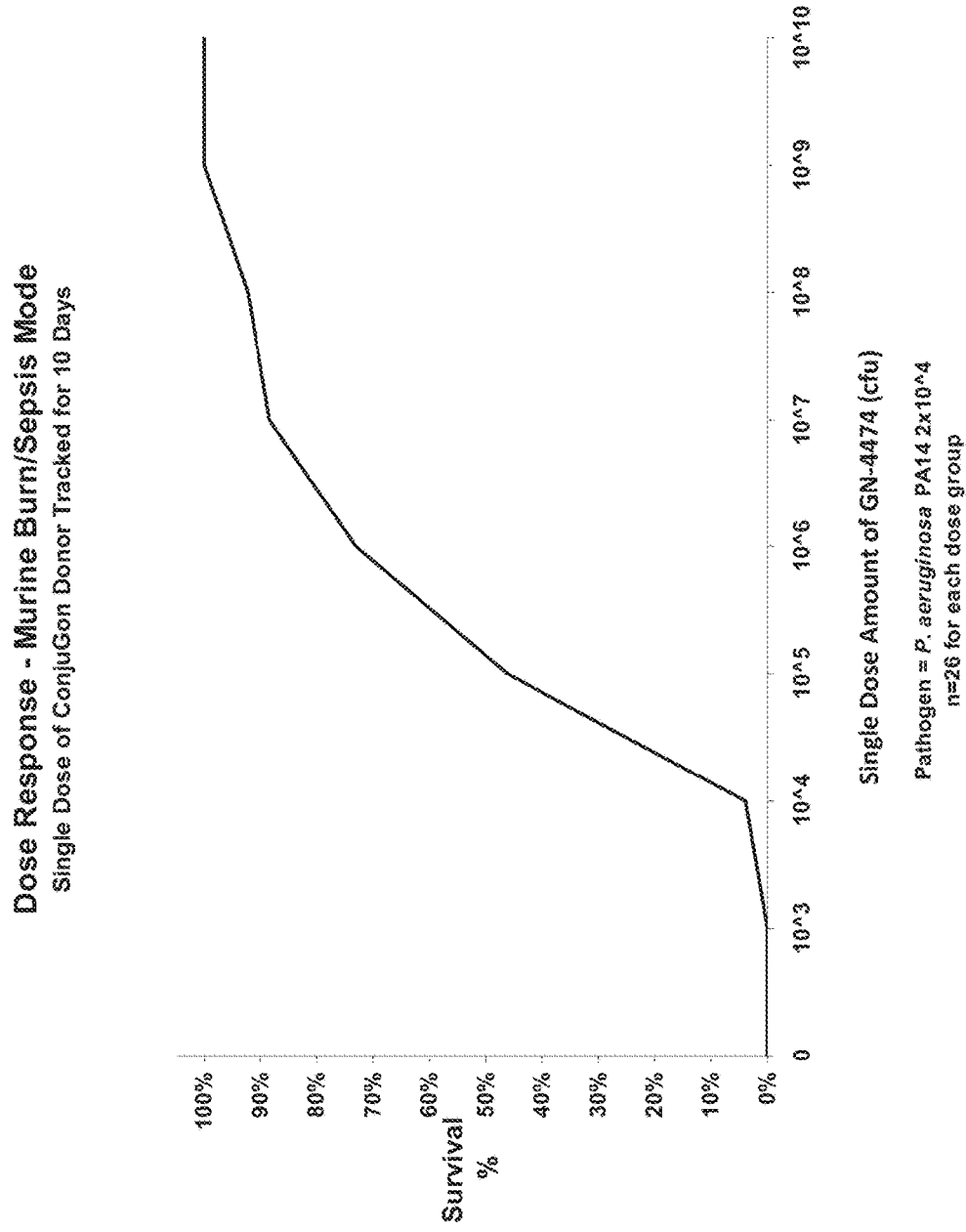
FIG. 23 shows dose response and efficacy testing of GN-4474 against *Pseudomonas aeruginosa* PA14 in skin burns.
Figure 24:
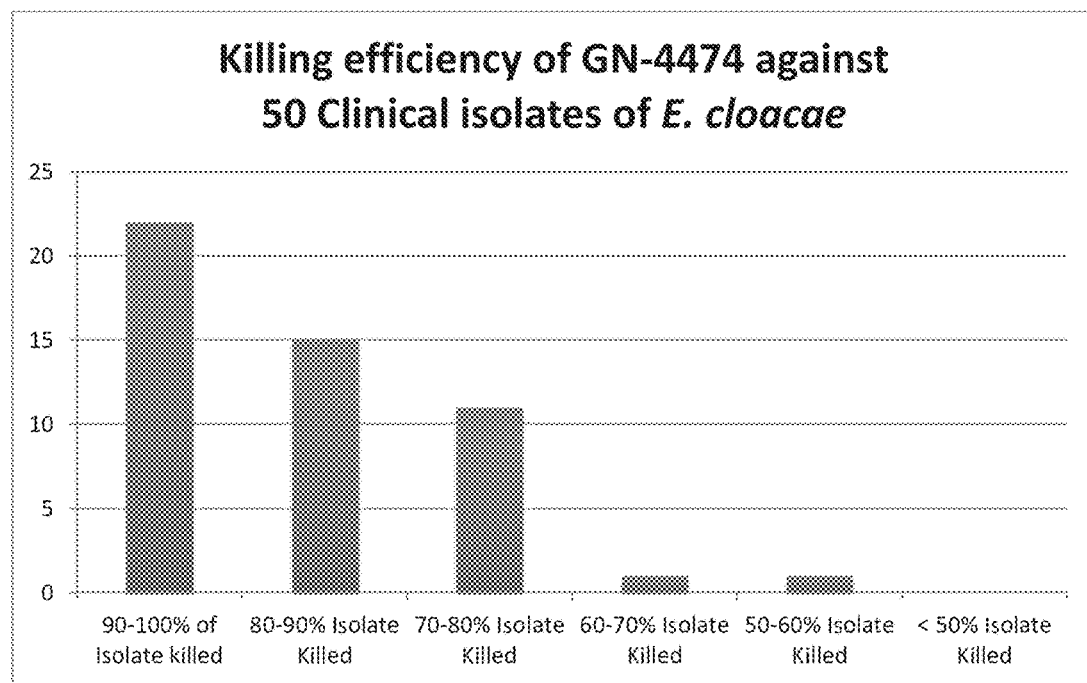
FIGS. 24A-24E show graphs showing the killing efficacy of GN-4474 against clinical isolates of *E. cloacae, K. pneumoniae, A. baumannii, E. coli*, and *P. aeruginosa*. The number of clinical isolates of each pathogen are indicated. The graphs show the percent killed for each isolate tested on the x axis, with the number of isolates of a particular pathogen falling into each percentage range is shown on the y axis.
Figure 24:
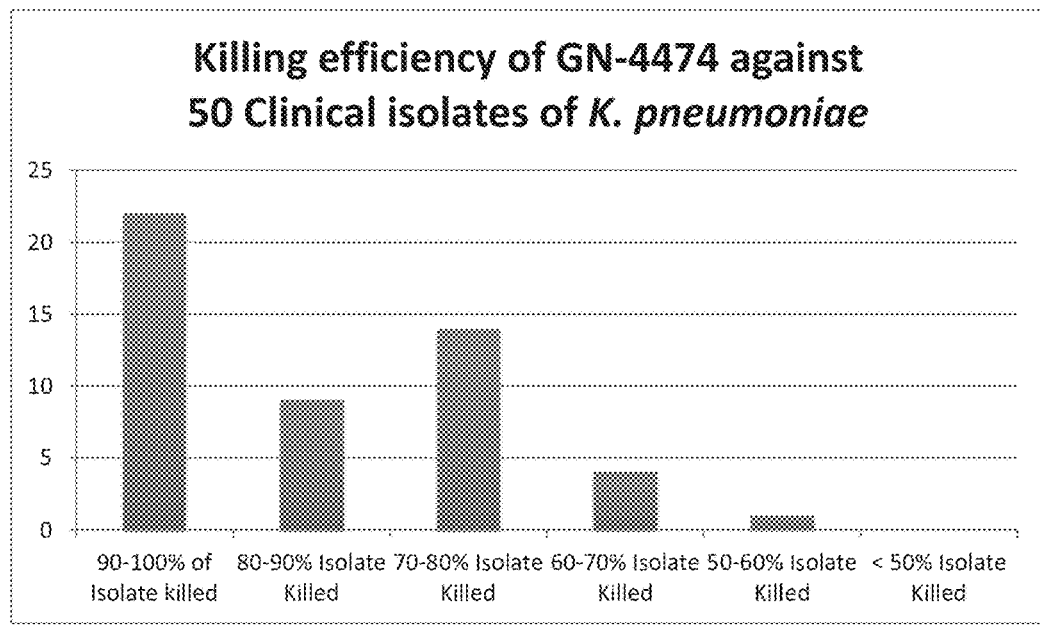
Figure 24:
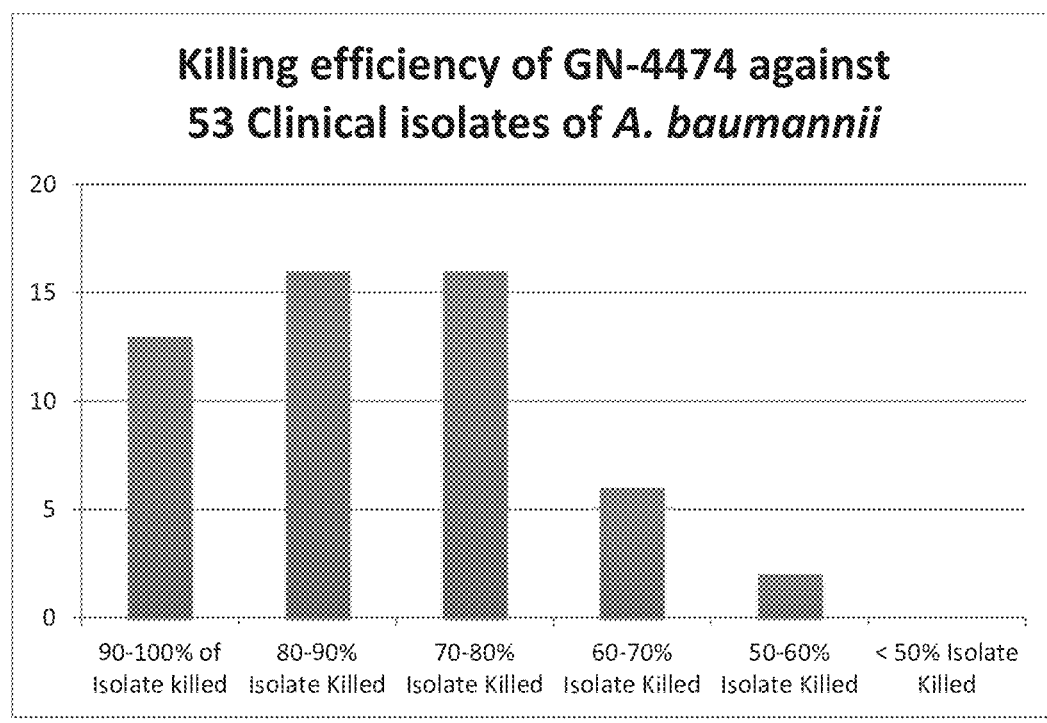
Figure 24:
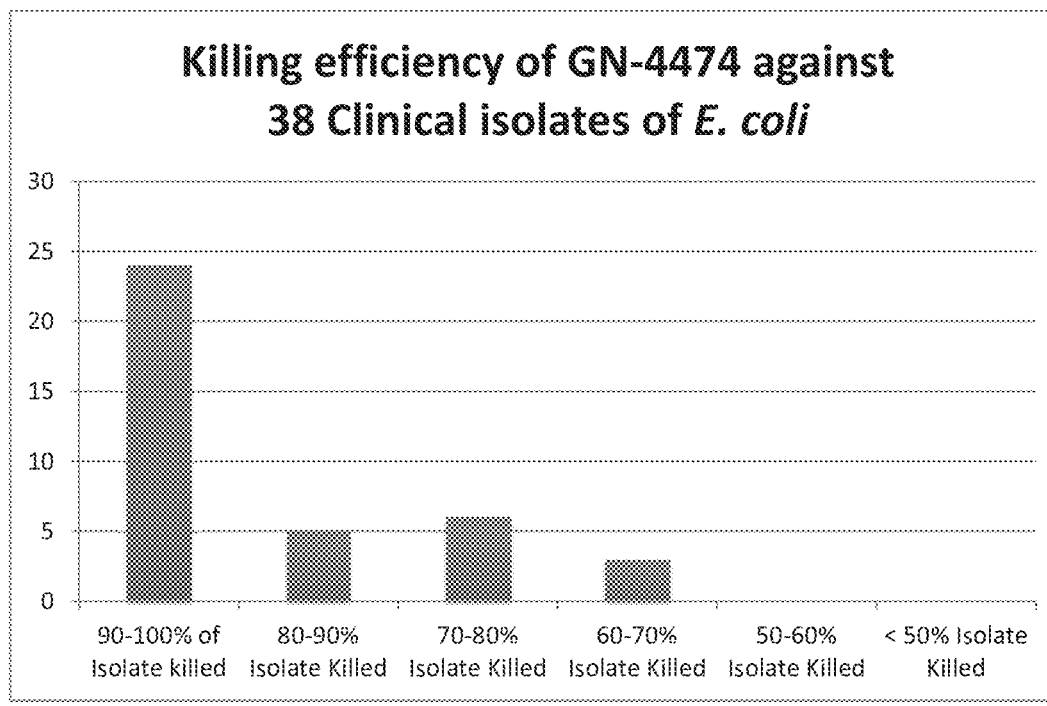
Figure 24:
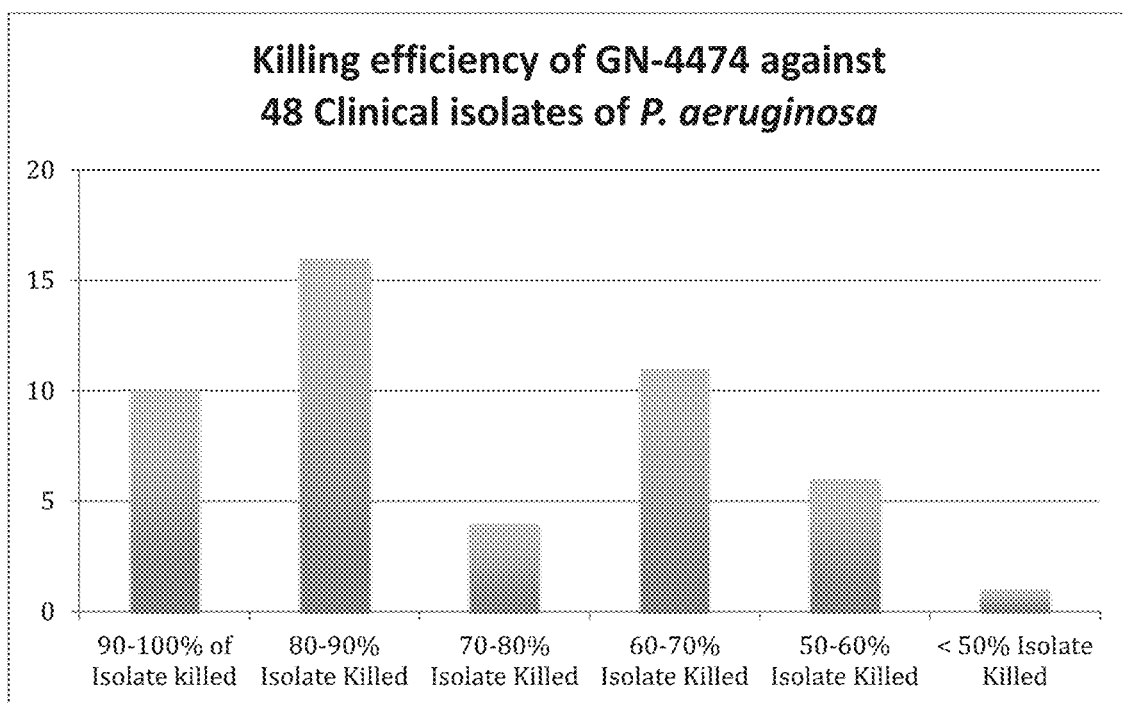

For mice infected with *P. aeruginosa*, approximately 50% survival of mice occurred with treatment with $6.0\times10^5$ cfu of GN-4474 to a burn area of about 20 mm$^2$. As shown in FIG. 23, the treatment under these conditions produced the following results:

Approximately 75% survival was achieved with treatment with $7.0\times10^6$ cfu of GN-4474. Greater than 85% survivability was achieved with treatment with $5\times10^7$ cfu of GN-4474. Greater than 90% survivability was achieved with $5\times10^8$ cfu of GN-4474 and 100% survivability was achieved with doses of $4.9\times10^9$ cfu or greater.

In some embodiments, tissue injuries may be debrided prior to treatment, while in some embodiments, the formulations of the invention may be applied without debridement.

b) Treatment Dosing: Topical

During development of the technology, it was determined that GN-4474 could be used in treating established infections. In certain preferred embodiments, topical treatment of an infected lesion comprises at least one administration of $1\times10^{10}$ cfu of GN-4474 for a lesion of 20 mm$^2$ of tissue area. In some embodiments, the treatment at this dosage is repeated 2 times, preferably 3 times, or more. In certain preferred embodiments, the treatments are repeated at regular intervals, e.g., every 4 to 6 hours.

It was further determined that treatment of established infections typically required higher or more frequent dosing than preventive treatments. Thus, treatment regimens applicable for existing infections are also useful as preventative treatments.

c) Subeschar Treatments

In some embodiments, treatment of a burn is done without debriding the burn wound. GN-4474 is applied, e.g., by injection below the eschar but above the underlying muscle tissue. In certain embodiments, treatment by subeschar injection reduces the dosage of GN-4474 needed to treat or prevent infection. For example, on a 20 mm$^2$ burn site, injection of a single dose of $1.0\times10^9$ cfu GN-4474 resulted in nearly 1 log reduction in the number of surviving pathogen organisms.

C. Growth and Storage of GN-4474

The compositions of the technology are configured such that they require supplemental amino acids in order to grow, so that in use, e.g., as applied to a skin lesion, they are deprived of essential amino acids and cannot further divide. In particular, GN-4474 requires 2,6-diaminopimelic acid in order to grow. As applied to tissue, e.g., on a skin lesion, 2,6-diaminopimelic acid is not available and the donor bacterium thus cannot grow at the application site (i.e., it cannot colonize the site or otherwise propagate). However, the conjugation function of donor cell is maintained, so that the transmissible plasmid carrying toxin genes may be transferred into a recipient pathogen cell. The plasmid is configured to express encoded toxins in susceptible target pathogens, killing the pathogens.

Different types of bacteria can typically only remain viable for a finite period of time without being "manipulated". For most applications, bacteria can be stored in a state (or set of conditions) that doesn't require optimized conditions, since a relatively small amount of viable bacteria can be grown and expanded to achieve the desired number of bacteria. However, the GN-4474 composition is a live viable *E. coli* bacteria that is intended to be used as a topical therapeutic to treat, e.g., antibiotic resistant bacteria. For therapeutic use, the GN-4474 cannot be "regrown", it must be in its final formulation and concentration that it is intended to be used at in the hospital setting. During development of the technology, it has been shown that to achieve therapeutic levels, GN-4474 is typically applied at a high concentration (e.g., approx. $1\times10^{10}$ cfu/ml).

There are many different ways to store bacteria: frozen in glycerol or other sugars, in a freeze dried powder, or even on agar plates for short time, but not at levels that maintain the necessary high concentration of live cells, without the need for further expansion and growth prior to use. In some embodiments, the technology is directed to ways to store GN-4474 for both short term (~2 weeks) and long term (>1 year) periods of time, while maintaining a very high level of viability and conjugation efficiency. Indeed, some typical bacteria storage conditions may maintain viability, but these same conditions may not maintain conjugation efficiency.

a) Short Term Storage: 4° C. in Liquid

During development of the technology, it was determined that the concentration at which *E. coli* configured for conjugative transfer is maintained during short term storage (e.g., prior to either freezing or lyophilization) has a significant effect on both viability of the *E. coli* strain and on the efficiency with which it can conjugate with recipient cells. For *E. coli*, e.g., GN-4474 as provided herein, it has been determined that $1\times10^6$ to about $1\times10^9$ cfu/ml may be used for storage, preferably $1\times10^8$ to $1\times10^9$ cfu/ml, with $1\times10^9$ cfu/ml being a particularly preferred concentration for short-term storage, whereby maintenance of both viability and conjugation efficiency are improved significantly relative to significantly more concentrated preparations.

b) Storage Formulations

At the preferred concentration, the composition of the storage medium appears to have an influence on conjugation, but little influence on viability. It was very surprising that conjugation efficiency was better for short term storage when the cells were maintained in spent medium rather than in fresh buffer, as it is typically considered that bacteria should be healthier and more stable when they are removed from a milieu that is depleted of nutritional elements and is laden with waste products. Therefore it is clear that multiple factors influence the stability of the *E. coli* GN-4474 for short term storage, and that once proper storage concentration is maintained, exact buffer composition influences conjugation efficiency, but has less effect on viability. This would indicate through multiple experiments, that as long as the concentration of *E. coli* is maintained at or below $1\times10^9$ cfu/ml, viability of the bacteria at 4° C. can be maintained in spent medium, or in excipient buffer with or without HEC. However, the conjugation efficiency of the bacteria at 4° C. is better maintained in spent medium rather than in buffer with or without HEC.

c) Short Term Storage at 4° C.

Short term storage temperature influences both viability and conjugation efficiency. Different sugars also influence viability. As discussed below in Example 8, glucose as a sugar in short term storage medium is not as good as sucrose or trehalose for maintaining viability. However, all three sugars maintain conjugation efficiency when stored at 4° C. These data show that viability and conjugation efficiency are not directly related and that varying conditions, e.g., sugars, can affect one feature without affecting the other.

d) Controlled Freezing for Long and Short-Term Storage

In general, when bacteria are frozen it is considered that the cells are metabolically inactive (no biological processes are happening until the bacteria are thawed and incubated at their appropriate temperature, which for E. coli is typically at least 30° C.). The data shown for the controlled freeze experiment is therefore quite surprising, as viability was maintained throughout the course of the experiment (no appreciable death of the bacteria occurred). For the first 14 days of the experiment the controlled frozen bacteria maintained excellent conjugation efficiency, in fact it was indistinguishable from freshly prepared GN-4474. However, starting at day 28, the conjugation efficiency started to decrease and continued to get worse throughout the course of the experiment until it was terminated. As it is understood that the bacteria should have been essentially biologically inactive at this frozen −20 C temperature, yet even though viability remained constant, conjugation efficiency decreased. This decrease is obviously not a result of a loss in viability. Also it was not the result of the "initial stresses of the freezing procedure" since conjugation efficiency was unaffected for the first 2 weeks.

e) Snap Freezing

Snap freezing, or flash freezing, is the process by which the samples are lowered to ultra-low temperatures, e.g., below −70° C., very rapidly. Snap freezing typically involves using dry ice or liquid nitrogen. The snap-freezing protocol described in Example 9 maintains both the viability and killing efficiency of GN-4474 in excipient buffer (50 mM KPO$_4$ buffer, 10% trehalose or sucrose, 2% glycerol) for extended periods of time at −80° C. Snap freezing protocols have been developed that maintain the both the viability and killing efficiency using a much lower percentage of glycerol than used in typical bacterial freezing protocols (2% vs. the typical 15-40%).

d) Freeze Drying

Example 10 shows that GN-4474 freeze dried in excipient buffer (50 mM KPO$_4$ buffer, 10% trehalose or sucrose, 2% glycerol and 0.5% HEC) may be stored for extended periods of time at −80° C. while maintaining both the viability and killing efficiency.

EXPERIMENTAL

The following examples are provided in order to demonstrate and further illustrate certain preferred embodiments and aspects of the present invention and are not to be construed as limiting the scope thereof. During the development of the technology herein, a dose range was determined in which GN-4474 is therapeutic for both the prevention of and treatment of gram negative bacterial infections in a burn using a variety of different application strategies. Provided hereinbelow are exemplary methods for applying the GN-4474 in combination with a wide range of burn dressings and bandages.

In the experimental disclosure that follows, the following abbreviations apply: ° C. (degrees Centigrade); cm (centimeters); g (grams); l or L (liters); μg (micrograms); μl (microliters); μm (micrometers); μM (micromolar); μmol (micromoles); mg (milligrams); ml (milliliters); mm (millimeters); mM (millimolar); mmol (millimoles); M (molar); mol (moles); ng (nanograms); nm (nanometers); nmol (nanomoles); N (normal); pmol (picomoles); bp (base pairs); cfu (colony forming units); Invitrogen (Invitrogen, Carlsbad, Calif.); lacOP (region encoding the E. coli lac operator/promoter); Kan (determinant for kanamycin resistance); Cm (determinant for chloramphenicol resistance); Tra1 (region encoding genes responsible for conjugative transfer); Control (region encoding control region); oriV (region encoding the origin of vegetative replication); oriT (region encoding the origin of conjugative transfer); tetR (gene encoding repressor of tetA); tetA (gene encoding resistance to tetracycline); Rep (region encoding genes responsible for replication); Primase (region encoding genes involved in replication); Tra2 (region encoding genes responsible for mating pair formation); colE3 (gene encoding colicin E3); colx10$^7$ (gene encoding colicinx10$^7$); immE3 (gene encoding the immunity protein for colicin E3); immE7 (gene encoding the immunity protein for colicinx10$^7$), repA, repB and repC (encode proteins essential for vegetative replication of plasmid RSF1010); mobA, mobB and mobC (encodes proteins responsible for mobilization of RSF1010); region encoding iterons, ssiA and ssiB (origins of vegetative replication), lacI$^Q$ (gene encoding the lac repressor protein) Arc/Mnt (hybrid repressor system), msbB (gene encodes an enzyme responsible for attaching a myristoyl group to lipopolysaccharide), dapA (gene encoding dihydropicolinate synthase) aroA (gene encoding 5-enolpyruvylshikimate 3-phosphate synthase), recA (gene encoding the recA DNA recombination protein)

Example 1

Donor Bacterium Construction: Construction of E. coli CON31-85A

This example describes the construction of an exemplary donor strain, E. coli CON31-85A. This strain was derived from the wild type E. coli strain MG1655 following the steps shown in FIG. 12. E. coli MG1655 was the first completely sequenced strain of E. coli (Blattner et al, Science. 1997 Sep. 5; 277(5331):1453-62.)

1. msbB Deletion and lacI$^Q$ Insertion

The first genetic alteration to E. coli MG1655 was the deletion of msbB with a lacI$^Q$ insertion to take the place of msbB. The msbB gene encodes an enzyme responsible for attachment of an acyl group in the lipid A of lipopolysaccharide (LPS), the primary component of bacterial endotoxin. This mutant strain of E. coli still synthesize LPS lacking the acyl group, and this modified LPS represents significantly reduced (almost 1 million fold) endotoxic effect. This modification in E. coli CON31-85A will significantly reduce the endotoxic effect of GN-4474 upon its application in humans.

Figure 13:
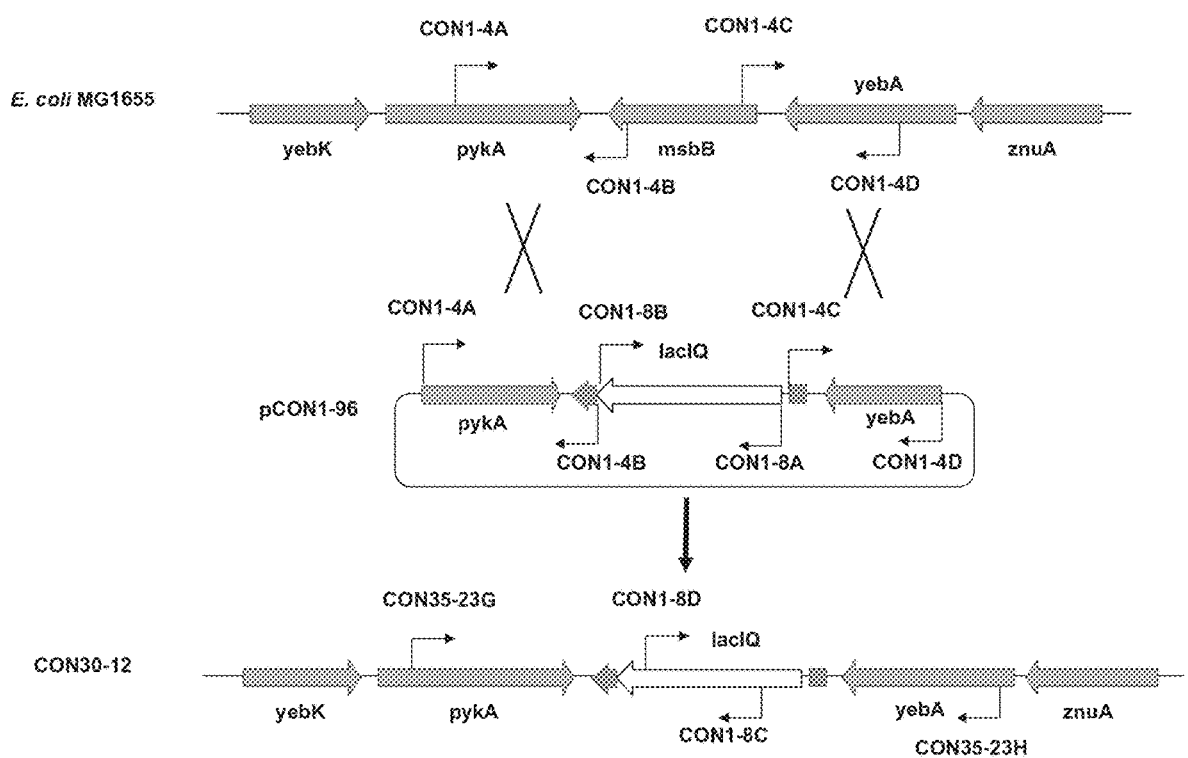
FIG. 13 shows a schematic representation of the two-step homologous recombination event that deletes msbB in *E. coli* MG1655 and replaces msbB with lacI$^Q$, using the suicide plasmid pCON1-96.

The msbB gene in MG1655 was deleted using a standard two-step homologous recombination procedure. This gene deletion (or knock out (KO)) was combined with insertion of lacI$^Q$ to take the place of msbB using a gene replacement plasmid (pCON1-96). Since expression of colE3 was repressed with LacI; overexpression of lacI was designed by introducing a second copy of lacI$^Q$. Note that lacI$^Q$ has a point mutation in its promoter region, which yields higher expression of lacI. The summary of this gene replacement is depicted in FIG. 13. Table 1 lists the individual primers and corresponding primer sequences used to create the pCON1-96 suicide vector and to detect the homologous recombination events that delete the msbB gene and insert the lacI$^Q$ gene in replacement.

TABLE 1

Table sequence of primers used to detect the msbB deletion and lacI$^Q$ insertion

| Primer name | DNA sequence | SEQ ID NO: |
|---|---|---|
| Con1-4A | 5'-CCTCGAGCGTTGATTGGCGTAGATTACCTG | 1 |
| Con1-4B | 5'-CGGATCCCAACCGTATAAGCGCAAAGATCT | 2 |
| Con1-4C | 5'-CGGATCCTTTTCCCAGTCGTCCGGCAAAAC | 3 |
| Con1-4D | 5'-GAAGCTTTGTTGCCAGCGCCAGAAA | 4 |
| Con1-8A | 5'-CGGATCCAATTATGGTGCAAAACCTTTCGC | 5 |
| Con1-8B | 5'-GGGATCCGCGCTAACTCACATTAATTGCG | 6 |
| Con1-8C | 5'-GCACAATCTTCTCGCGCAAC | 7 |
| Con1-8D | 5'-GATCGTTGGCAACCAGCATC | 8 |
| Con35-23G | 5'-GTCAGCAATGTACGCAGCTAAC | 9 |
| Con35-23H | 5'-GTATCGCGCTTTCCCGGTAATAC | 10 |

Primer names and corresponding sequences of the primers used to create the suicide vector pCON1-96 and to detect the deletion of msbB and insertion of lacI$^Q$.

Figure 14:
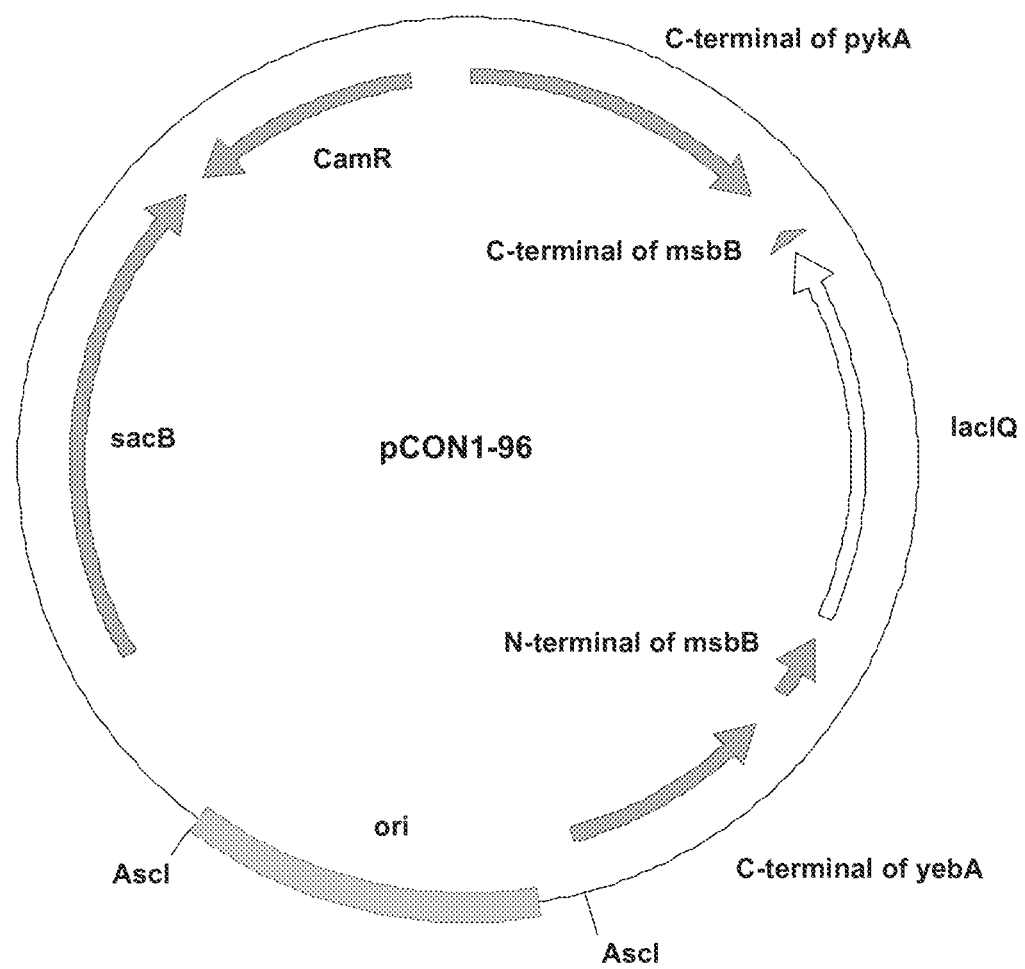
FIG. 14 shows a plasmid map of the pCON1-96 suicide vector used to create the msbB deletion and lacI$^Q$ insertion in *E. coli* MG1655. A portion of pykA and yebA are included in the vector to facilitate homologous recombination. Positive selection gene CamR and counter selective gene sacB are also shown on the map. The ori was excised using AscI restriction enzyme digestion followed by recirculation with T4 DNA ligase prior to transforming *E. coli* MG1655. This gene replacement process deleted 756 bp or the majority of the msbB coding region, and instead an 1197 bp fragment containing lacI$^Q$ was inserted in place of msbB.

Construction of the msbB gene replacement vector pCON1-96 is shown in FIG. 14. The 5' and 3' flanking regions of msbB were PCR cloned using primer pairs, con1-4C/con1-4D, and con1-4A/con1-4B, respectively. The lacI$^Q$ region was also PCR cloned from E. coli JM109 using the pair of primers con1-8A/1-8B. The cloned DNA fragments were verified by DNA sequencing. These fragments were assembled into a plasmid pCON1-96 (FIG. 14). This vector has both a selectable marker CamR and counter selective marker sacB on the plasmid. Prior to transformation, pCON1-96 was digested with AscI to eliminate the replication origin (ori) of the plasmid, and the replicon-less plasmid was circularized by T4 ligase prior to transforming E. coli MG1655. Transformants were selected on Luria bertani agar containing 50 µg/mL chloramphenicol (Cam, 50 µg/mL), and growing colonies were analyzed by PCR to verify homologous recombination at either 5' or 3' flanking region of msbB. The PCR primers used for this analysis are listed in the Table 1 above, and locations of these primers are indicated in FIG. 13. The candidate colonies containing the integrated pCON1-96 were subsequently grown in LB broth cultures containing 7% sucrose (with no chloramphenicol), overnight. The cultures were then subcultured for 2 days and were diluted and plated on LB agar containing 7% sucrose without chloramphenicol selection to counter select sacB-containing bacterial cells. Colonies growing on the plate are either msbB-deletion mutants or revertants to wild type, which was verified by PCR using the primer pairs listed in the Table 2.

Recombined homologous regions are verified by phenotypes (sucrose insensitive, and chloramphenicol sensitive), and PCR products specific to these recombinations. The primers and the sized of the PCR products are listed in table 2 below.

Table 2. PCR primer combinations used in PCR analysis to detect the msbB deletion and lacI$^Q$ insertion following homologous recombination. Correct amplicon sizes are shown for the resulting E. coli CON30-12 strain, while amplification of the parental E. coli MG1655 strain, will not yield any amplicons.

TABLE 2

Specific PCR products from recombinant strain CON30-12

| PCR primers* | Product size from CON30-12 | Product size from parental strain MG1655 (wild-type) |
|---|---|---|
| Con1-8C/con35-23G | 1297 bp | none |
| Con1-8D/con35-23H | 1306 bp | none |

*See the locations of the primers in FIG. 13.

Genotype of resulting strain CON30-12: K-12 E. coli MG1655 ΔmsbB::lacI$^Q$ 2. dapA Deletion and immE3-Arc/Mnt Insertion The second genetic alteration to E. coli MG1655 was the deletion of dapA with an immE3-arc/mnt insertion to take the place of dapA. The dapA gene encodes an enzyme partially responsible for the synthesis of the bacterial cell wall and lysine. A dapA mutant can grow with medium supplementation with the compound diaminopimelic acid (DAP), which is a precursor in the biosynthetic pathway. The dapA gene in E. coli CON30-12 was deleted using a standard two-step homologous recombination procedure. The dapA gene deletion was combined with integration of immE3 and mnt/arc using a gene replacement plasmid, pCON30-31. LacI represses expression of the bactericidal gene colE3 on the plasmid pCON44-74. However, leaky expression of colE3 could cause a detrimental effect on the host survival; thus immE3 was integrated into the host chromosome to neutralize the toxicity of even the smallest amounts of ColE3 within the CON31-85A host cell. The dapA deletion genotype was introduced to restrict the growth of the host stain in a DAP limiting environment; thus it prevents spread of the bacterium. This process caused a deletion of 833 bp within the dapA coding region. However, the immE3 and Mnt/Arc genes were integrated into this site. The summary of this gene replacement strategy is depicted in the FIG. 15.

Table 3 lists the individual primers and corresponding primer sequences used to create the pCON1-96 suicide vector and to detect the homologous recombination events that delete the msbB gene and insert the lacI$^Q$ gene in replacement. Primer names and corresponding sequences of the primers used to create the suicide vector pCON30-31 and to detect the deletion of dapA and insertion of immE3-Arc/mnt.

TABLE 3

Sequence of primers used to detect the dapA deletion and immE3-Arc/Mnt insertion.

| Primer name | DNA sequence | SEQ ID NO: |
|---|---|---|
| Con8-59A | 5'-GAAGCTTTGCCATCAGCGTCAATCAGGAAG | 11 |
| Con8-59B | 5'-GGGATCCGACAATACTTCCCGTGAACATGGG | 12 |
| Con8-59C | 5'-GGGATCCAAGCATGCCGGTTTGGTGTAAAGT | 13 |
| Con8-59D | 5'-CACTAGTGACGCACACGTTTGCGTATCATATC | 14 |
| Con13-4A | 5'-ACAACGTCGTGGTGATTGCTGGTTT | 15 |
| Con13-4D | 5'-CGAATTACCGCTAAAATCGC | 16 |
| Con35-23c | 5'-GCAACGATGCAGAACGACTC | 17 |
| Con35-75c | 5'-CTTCAGCGTATCAAACACCATCTTC | 18 |

Figure 15:
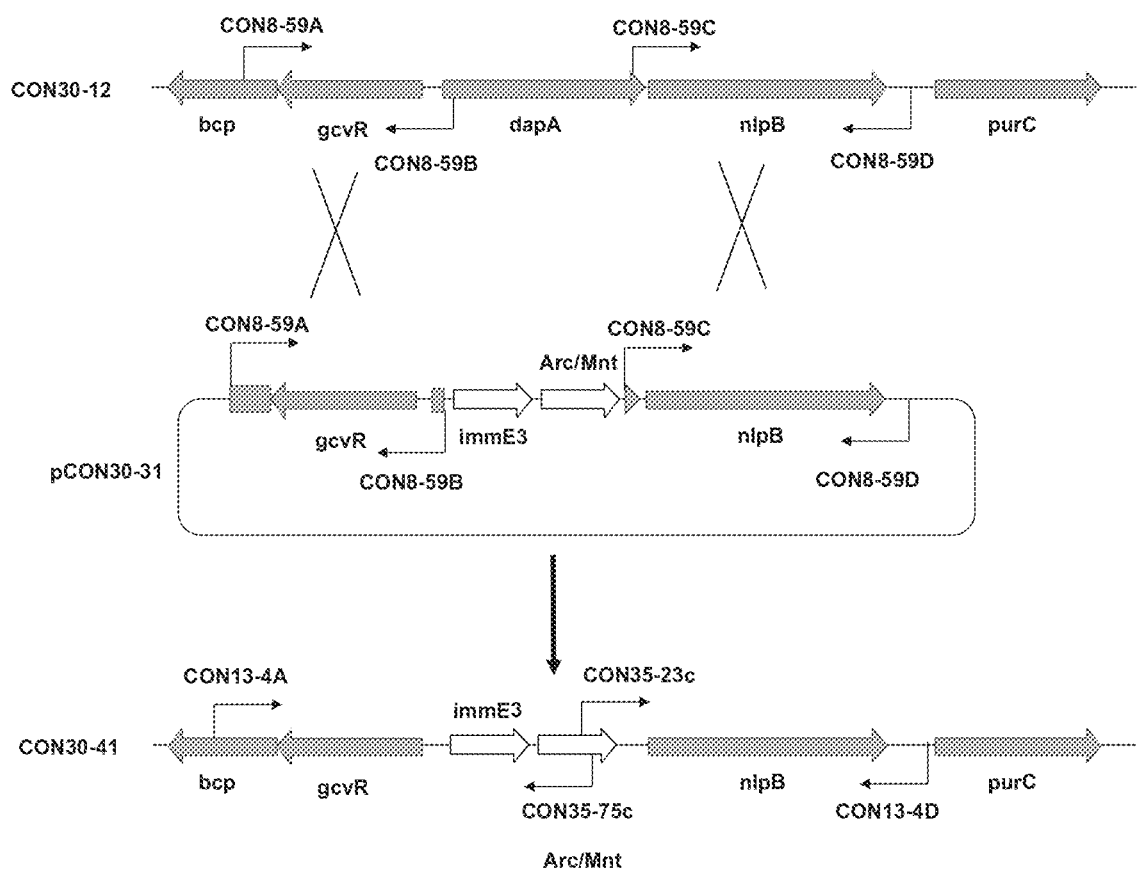
FIG. 15 shows a schematic representation of the two-step homologous recombination event that deletes dapA in *E. coli* CON30-12 and replaces dapA with immE3-Arc/mnt, using the suicide plasmid pCON30-31.
Figure 16:
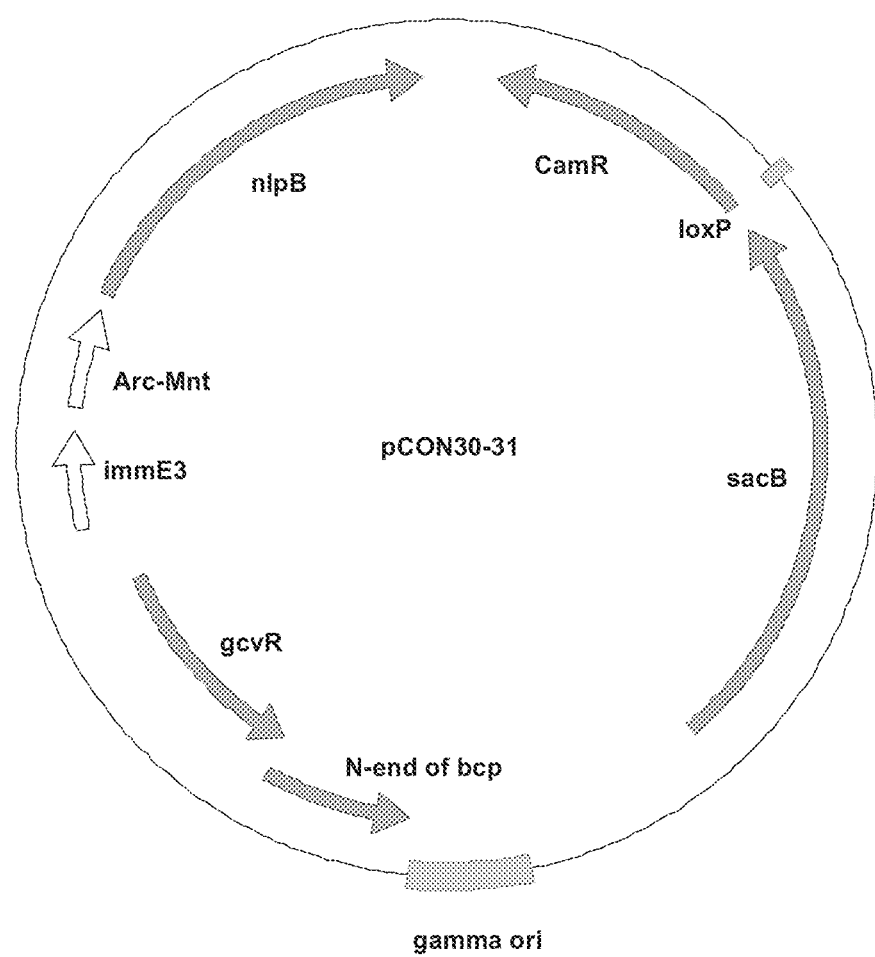
FIG. 16 shows a plasmid map of the pCON30-31 suicide vector used to create the dapA deletion and immE3-Arc/mnt insertion in *E. coli* CON30-12. A portion of nlpB and gcvR are included in the vector to facilitate homologous recombination. Positive selection gene CamR and counter selective gene sacB are also shown on the map. This suicide vector utilizes a R6K gamma origin of replication, that requires the Pi protein that is not found on this plasmid or in the CON30-12 strain, therefore the plasmid cannot replicate and is deemed a suicide vector.

Construction of a dapA gene replacement vector pCON30-31 is shown in the FIG. 16 below. The 5' and 3' flanking regions of dapA were PCR cloned from the chromosomal DNA of *E. coli* MG1655 using two pairs of primers con8-59A/con8-59B and con8-59C/con8-59D, respectively (FIG. 15). The immE3 and the arc/mnt hybrid genes were PCR cloned using two pairs of primers. These fragments were assembled into a plasmid pCON30-31 (FIG. 16). This vector has both a selectable marker CamR and counter selective marker sacB on the plasmid. The suicide plasmid pCON30-31 has a gamma R6K origin of replication that cannot replicate in *E. coli* MG1655 (or CON30-12) since these strains do not have the pir gene coding for the Pi replication protein required for R6K origins of replication. This pCON30-31 suicide vector was then electroporated into *E. coli* CON30-12. Transformants were selected on Luria bertani agar containing 100 μg/mL of 2,6-diaminopimelic acid and 50 μg/mL chloramphenicol (Cam, 50 μg/mL), and growing colonies were analyzed by PCR to verify homologous recombination at either 5' or 3' flanking region of dapA. The PCR primers used for this analysis are listed in the Table 3 above, and locations of these primers are indicated in FIG. 15. The candidate colonies containing the integrated pCON30-31 were grown in LB broth cultures containing 100 μg/mL of 2,6-diaminopimelic acid and 7% sucrose (no chloramphenicol) overnight. These overnight cultures were then subcultured for 2 days, diluted and plated on LB agar containing 100 μg/mL of 2,6-diaminopimelic acid and 7% sucrose without chloramphenicol selection to counter select sacB-containing bacterial cells. Colonies growing on the plate are either dapA-deletion mutants or revertants to wild type, which was verified by PCR using the primer pairs listed in the Table 4. In addition growing colonies were also checked phenotypically, by replica plating on LB agar alone, since isolates that underwent a successful second counter selection should be unable to grow on LB agar alone without supplementation with 2,6-diaminopimelic acid.

Recombined homologous regions are verified by phenotypes (sucrose insensitive, and chloramphenicol sensitive), and PCR products specific to these recombinations. The primers and the sized of the PCR products are listed in Table 4, below. This process caused a deletion of 832 bp within the dapA-coding region. However, the immE3 and Mnt/Arc genes were integrated into this site.

TABLE 4

PCR primer combinations used in PCR analysis to detect the dapA deletion and immE3-Arc/mnt insertion following homologous recombination. Correct amplicon sizes are shown for the resulting *E. coli* CON30-41 strain, while amplification of the parental *E. coli* CON30-12 strain, will not yield any amplicons. Specific PCR products from recombinant strain CON30-41

| PCR primers* | Product size from CON30-41 | Product size from parental strain |
|---|---|---|
| Con35-23c/con13-4D | 1282 bp | None |
| Con35-75c/con13-4A | 1800 bp | none |

*See the locations of the primers in the FIG. 15.

Genotype of CON30-41:K-12 *E. coli* MG1655 ΔmsbB:: lacI$^Q$, ΔdapA::immE3-Arc/mnt 3. aroA Deletion and immx10$^7$-lacI$^Q$ Insertion The third genetic alteration to *E. coli* MG1655 was the deletion of aroA with an immx10$^7$-lacI$^Q$ insertion to take the place of aroA. Disruption of the aroA gene results in a block in the shikimate pathway of *E. coli*. This pathway is mainly responsible for the biosynthesis of aromatic amino acids; however, it can provide precursors for folate, enterochelin, and quinine biosynthesis. Published reports of *E. coli* aroA mutants demonstrated that these strains require the addition of aromatic amino acids, p-aminobenzoate, and p-hydroxybenzoate when grown in minimal medium. The aroA genotype was used to make the host strain dependent on a group of amino acids; thus aroA was used as a selective marker for the bactericidal plasmid. In a synthetic culture medium, the bactericidal killer plasmid carrying aroA was demonstrated to be stably maintained. The summary of this gene replacement is depicted in the FIG. 17.

Table 5. Primer names and corresponding sequences of the primers used to create the suicide vector pCON29-93 and to detect the deletion of aroA and insertion of immx10$^7$-lacI$^Q$.

TABLE 5 sequence of primers used to detect the aroA deletion and immE7-lacIQ insertion.

| Primer name | DNA sequence | SEQ ID NO: |
|---|---|---|
| Con29-28A | 5'-GGGAATTCATCGATGGTATCGCCATCGACGAAA | 19 |
| Con29-28B | 5'-GGGGATCCATATCATTGCTACCCAGACAAAGAGC | 20 |
| Con29-28E | 5'-GGGCATGCATGATTATATTTCCTGCACGCGTGG | 21 |
| Con29-28F | 5'-CGTGCGGCAACGATCGCATAAGAAGCTTTC | 22 |
| Con29-77B | 5'-CCTGTGCTCAGTATCACCGCCAGTG | 23 |
| Con29-91A | 5'-GCGTGGACCGCTTGCTGCAACTCTC | 24 |
| Con29-95A | 5'-CAGGTTGCAGAGGAAGCCGAGAAGG | 25 |
| Con29-95B | 5'-CTGAAATGGCATCGCGTGCGGCAAC | 26 |

Figure 17:
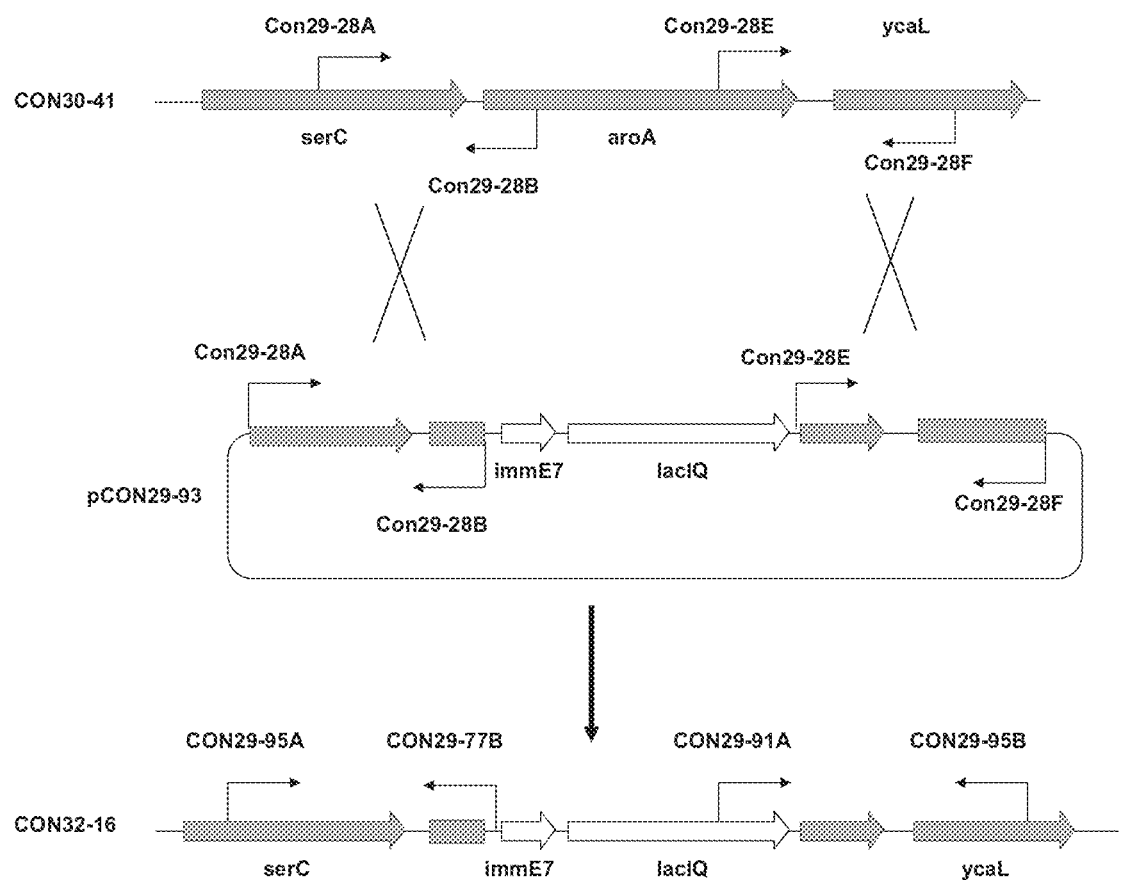
FIG. 17 shows a schematic representation of the two-step homologous recombination event that deletes aroA in *E. coli* CON30-41 and replaces aroA with immx10$^7$-lacI$^Q$, using the suicide plasmid pCON29-93.
Figure 18:
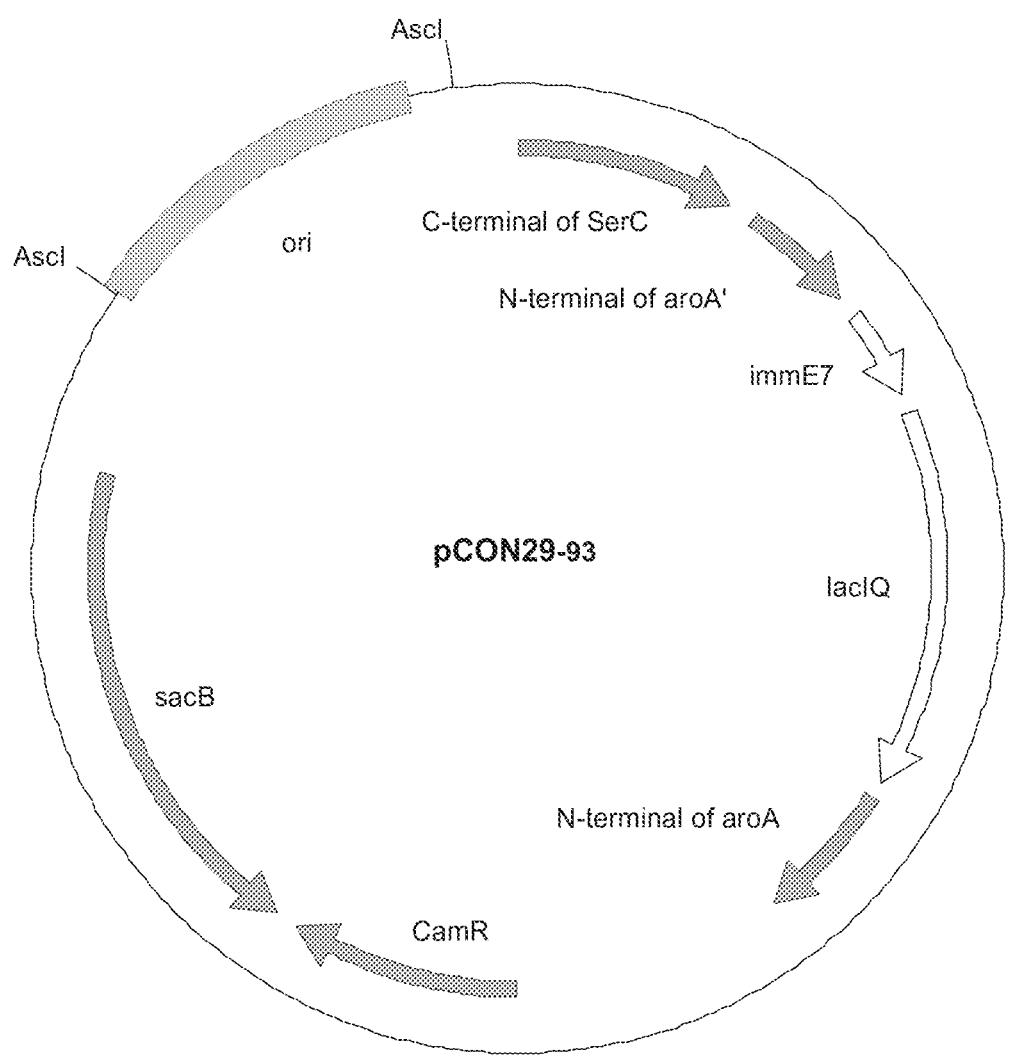
FIG. 18 shows a plasmid map of the pCON29-93 suicide vector used to create the aroA deletion and immx10$^7$-lacI$^Q$ insertion in *E. coli* CON30-41. A portion of serC and ΔaroA are included in the vector to facilitate homologous recombination. Positive selection gene CamR and counter selective gene sacB are also shown on the map. The ori was excised using AscI restriction enzyme digestion followed by recirculization with T4 DNA ligase prior to transforming *E. coli* CON30-41. This gene replacement process deleted an internal 756 bp or majority of the aroA coding region, and replaced this with immx10$^7$ and lacI$^Q$ genes that are inserted.

Construction of an aroA gene replacement vector, pCON29-93, is shown in the FIG. 18. The 5' and 3' flanking regions of aroA were PCR cloned from the chromosomal DNA of *E. coli* MG1655 using two pairs of primers con29-28A/con29-28B and con29-28E/con29-28F, respectively. The immx10$^7$ and the lacI$^Q$ genes were combined with these fragments and cloned into a plasmid to generate pCON29-93. This vector has both a selectable marker CamR and counter selective marker sacB on the plasmid. Following the cloning of the aroA flanking sequences and the immx10$^7$-lacIQ insert, the pCON29-93 plasmid was digested with AscI, and the replication origin was removed from the plasmid generating a replicon-less plasmid. The resulting replicon-less plasmid was circularized with T4 DNA ligase, and transformed into CON30-41. Since the plasmid is replicon-less the plasmid cannot be stably maintained as a plasmid in this strain. Chloramphenicol resistance was used as a positive selective marker for initial integration of DNA fragment, and sacB was used as a counter selective marker for the second homologous recombination. Initial transformants were selected on Luria bertani agar containing 100 μg/mL of 2,6-diaminopimelic acid and 50 μg/mL chloramphenicol (Cam, 50 μg/mL), growing colonies were analyzed by PCR to verify homologous recombination at either 5' or 3' flanking region of aroA. The PCR primers used for this analysis are listed in the Table 5 above, and locations of these primers are indicated in FIG. 17. The candidate colonies containing the integrated pCON29-93 were subsequently cultured in LB broth containing 100 μg/mL of 2,6-diaminopimelic acid and 7% sucrose without chloramphenicol overnight. These cultures were then subcultured for two days in the same medium without chloramphenicol, followed by dilution and plating on LB agar containing 100 μg/mL of 2,6-diaminopimelic acid and 7% sucrose without chloramphenicol selection to counter select sacB-containing bacterial cells. Correct recombinants were verified by PCR and the aroA-minus phenotype. Colonies growing on these plates are either aroA-deletion mutants or revertants to wild type, which was verified by PCR using the primer pairs listed in the Table 6. In addition growing colonies were also checked phenotypically, by replica plating on M9 minimum medium and M9 medium supplemented with aromatic amino acids (tyrosine, tryptophan and phenylalanine (100 μg/ml each), p-aminobenzoate (20 μg/ml) and p-hydroxybenzoate (20 μg/ml). Colonies possessing the correct aroA deletion phenotypically cannot grow on M9 minimal medium by itself, however the correct aroA deletion mutants can grow on M9 minimal medium with the aromatic amino acids and the p-aminobenzoate and p-hydroxybenzoate.

TABLE 6

PCR primer combinations used in PCR analysis to detect the aroA deletion and imm × $10^7$ -lacI$^Q$ insertion following homologous recombination. Correct amplicon sizes are shown for the resulting E. coli CON32-16 strain, while amplification of the parental E. coli CON30-41 strain, will not yield any amplicons.
Specific PCR products from recombinant strain CON32-16

| PCR primers* | Product size from CON32-16 | Product size from parental strain CON30-41 |
| --- | --- | --- |
| Con29-95A/ con29-77B | 1413 bp | None |
| Con29-91A/ con29-95B | 1303 bp | none |

*See the locations of the primers in the FIG. 17.

Figure 19:
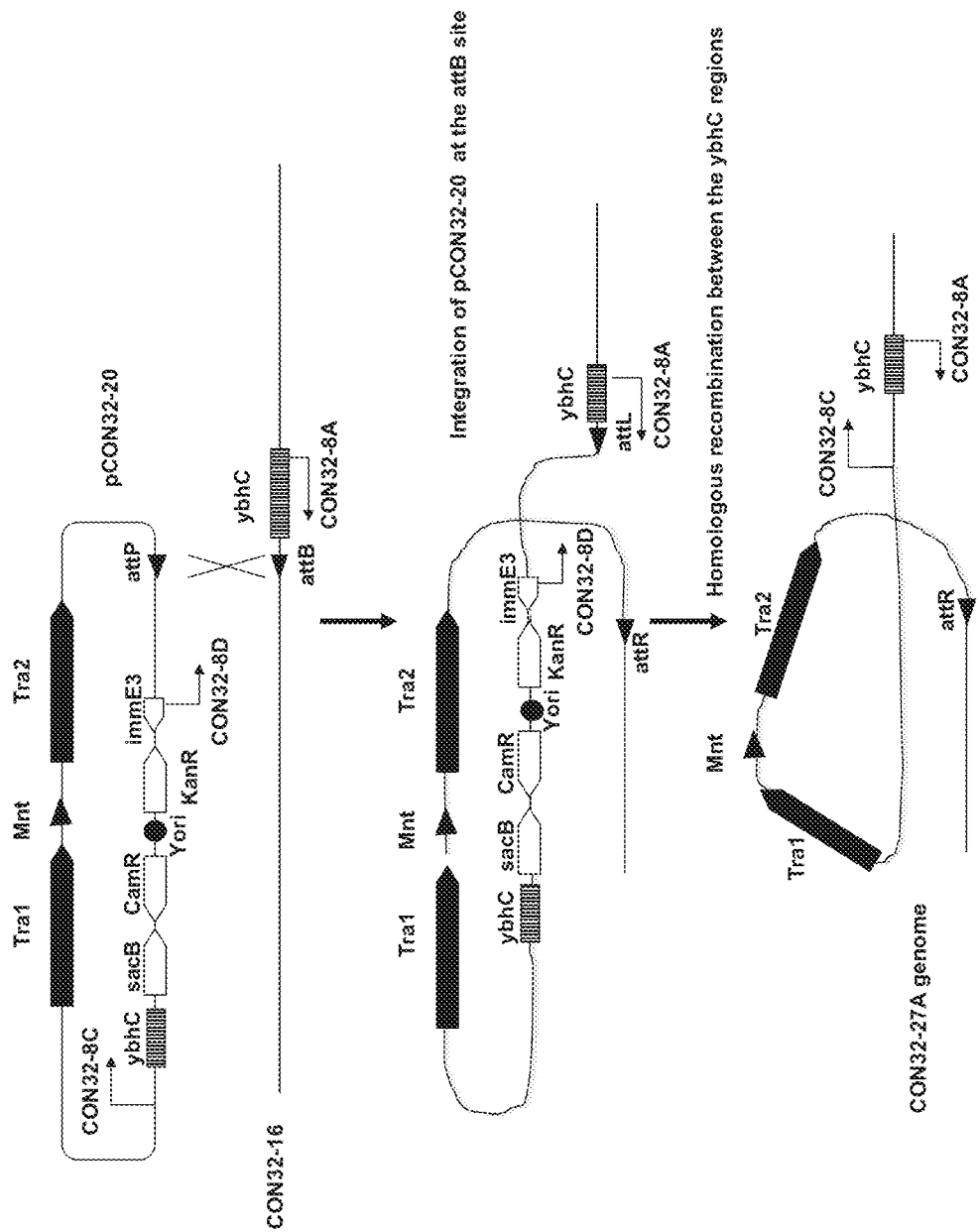
FIG. 19 shows a schematic diagram of pCON32-30 containing the RK2 tra genes integrated at the attB site. The following homologous recombination eliminated selective, counter selective and other unwanted genes from the plasmid. This process also eliminated attL, and excision of the fragment from the attB locus became irreversible. The two primers con32-8A and C were used to monitor the homologous recombination.

Genotype of CON32-16:
K-12 E. coli MG1655 ΔntsbB::lacIQ ΔdapA:ammE3-Arc/mnt, ΔaroA::immx$10^7$-lacIQ 4. Tra Integration with No Deletion The fourth genetic alteration to E. coli MG1655 was the integration of the tra operon into the chromosome of E. coli MG16556 at the lambda bacteriophage attachment site, attB (FIG. 19). The bactericidal plasmid pCON44-74 is a mobilizable plasmid that requires a set of tra genes to mediate its transfer from the donor cell (E. coli CON31-85A) to a recipient cell. The plasmid pCON44-74 utilizes RSF1010 for its transfer and replication, and the products of the RK2 tra genes can facilitate this process efficiently. A suicide plasmid containing the RK2 tra genes was constructed, and was integrated at the attB site of the host E. coli genome. Recombination of DNA Molecules between attB and attP is reversible, and catalyzed by the Int-Xis system of lambda bacteriophage. To avoid its potential gene transfer from the donor strain to another bacterial strain, the integrated plasmid was further modified to prevent its excision process (see the strategy in the FIG. 19). Briefly, the suicide plasmid carrying a DNA fragment of E. coli chromosome flanking to the attB site, part of the ybhC gene was cloned into this suicide vector as well. Following the site-specific integration of the plasmid at the attB site, homologous recombination between the two ybhC fragments took place. This process eliminated attL, and prevented potential excision of the plasmid DNA integrated at this location. The diagram of this plasmid integration is depicted in the FIG. 19.

Figure 20:
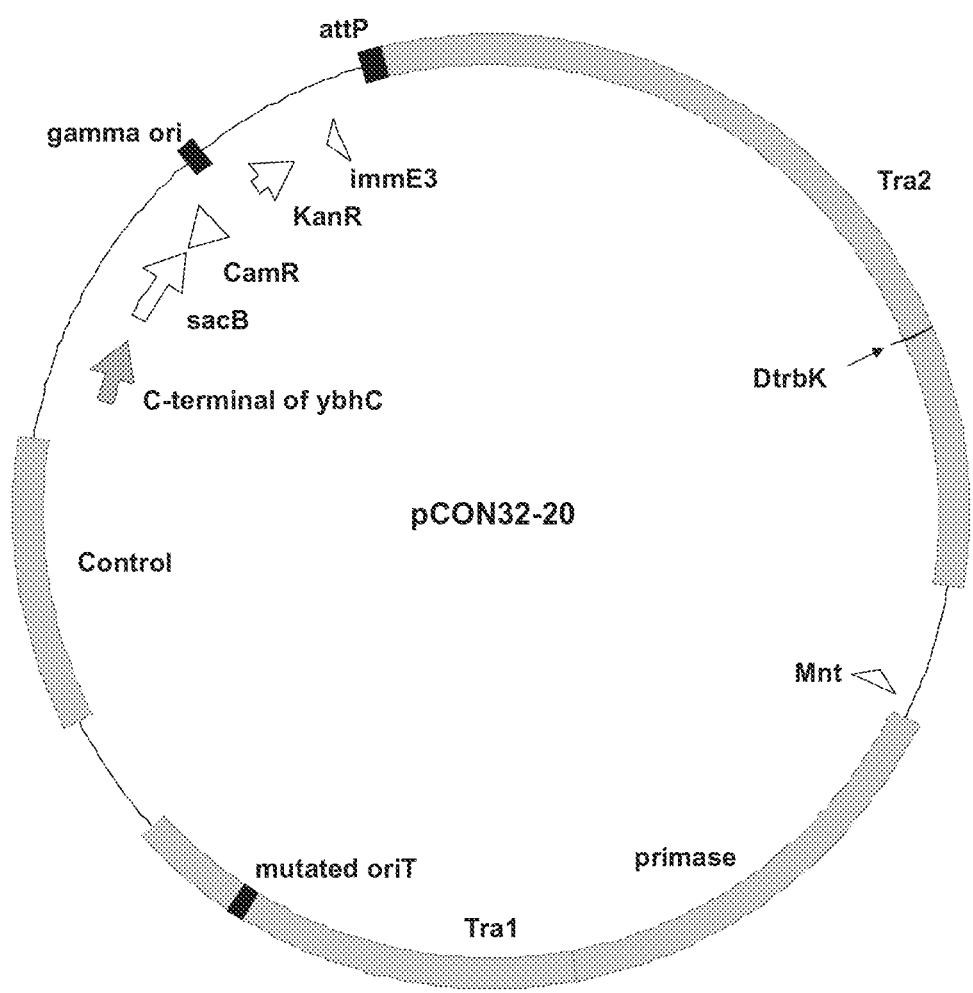
FIG. 20 shows a plasmid map of the pCON32-20 suicide vector used to create the tra integration in *E. coli* CON32-16. The attP recognition sequence for lambda integration was cloned into the plasmid. Also a portion of ybhC was included in the vector to facilitate the second homologous recombination event after the initial lambda based integration. Positive selection genes CamR or KanR and counter selective gene sacB are also shown on the map.

Construction of the tra-integrating suicide plasmid pCON32-20 is shown in FIG. 20. Many of the same features that were used in the other suicide vectors used to generate the chromosomal gene deletions in CON31-85A were also used in pCON32-20. The plasmid pCON32-20 is a large plasmid, in excess of 43 kb. The tra1 and tra2 regions that were cloned into this plasmid are responsible for providing conjugation machinery necessary for transferring plasmids in the final donor strain. The tra1 and tra2 regions must be inserted or integrated into the chromosome of CON31-85A. Since these regions are very large, using standard two-step homologous recombination to insert these regions into the chromosome is not feasible. Therefore the pCON32-20 suicide plasmid was designed to utilize the Int-Xis system of the lambda bacteriophage and the corresponding attB site in the host chromosome and the attP site in pCON32-20, which was specifically cloned into this suicide vector. The attB/attP site recombination event is normally reversible in nature. ConjuGon designed pCON32-20 to prevent excision from the host chromosome once integration occurred. To accomplish this, the pCON32-20 suicide vector was designed to carry a DNA fragment (part of the ybhC gene) of the host E. coli chromosome flanking attB site. Following the site-specific integration of the pCON32-20 plasmid at the attB site in the chromosome, homologous recombination between the two ybhC gene fragments takes place. During this homologous recombination event at the ybhC genes, the attL gene is eliminated, with prevents the potential excision of the plasmid DNA that is integrated at this location.

The suicide vector pCON32-20 has several important features (FIG. 20). The Tra1, Tra2 and Control regions (all required for conjugation) were cloned from the well-characterized plasmid RK2. The entire Tra1, Tra2 and control regions from RK2 were cloned with the exception trbK. Expression of the trbK gene has been shown to reduce conjugation efficiency dramatically in recipient cells. In order to prevent unwanted gene transfer of trbK from CON31-85A into bacterial pathogens, the gene was deleted. Elimination of trbK in the donor strain, CON31-85A, does not affect conjugation efficiency of the donor strain. Two separate antibiotic resistance markers, KanR for resistance to kanamycin and CamR for chloramphenicol resistance were cloned into the pCON32-20 plasmid to be used for positive selection for the first homologous recombination event (FIG. 19). The sacB gene was also cloned into pCON32-20 and used for negative selection to counter select the pCON32-20 plasmid, which will force the second homologous recombination event (FIG. 19). A copy of the immE3 gene was cloned into the pCON32-20 suicide plasmid however; immE3 was not essential for the purpose of this plasmid development, and after the gene-replacement process, immE3 was designed to be deleted. Expression of the Int protein is essential for recombination between attB and attP. The protein was expressed in trans from the plasmid pJW27, which expresses Int under a heat-inducible promoter. The plasmid pJW27, is not transferred into the final donor strain CON31-85A and is actually selected against in the final strain. Prior to cloning the entire Tra1, Tra2 and control regions from RK2, the origin of transfer (oriT) was mutated. ConjuGon specifically mutated the oriT to prevent the potential transfer of chromosomal DNA from CON31-85A into pathogenic target bacteria. The suicide vector pCON32-20 also carries the Mnt repressor protein that is under control of the lambda $P_L$ promoter that is constitutively expressed. This repressor protein is part of ConjuGon's novel Arc/Mnt hybrid promoter/repressor system used to regulate colx$10^7$ expression in the CON31-85A donor strain. The suicide plasmid pCON32-20 has a gamma R6K origin of replication that cannot replicate in E. coli MG1655 (or CON31-85A) since these strains do not have the pir gene coding for the Pi replication protein required for R6K origins of replication. During the plasmid construction, the Pi protein was provided in trans from a specific vector-construction host genome. Since the recipient of the plasmid CON32-16 did not express the Pi protein, the plasmid was not capable of replication; thus only the integrated plasmid could provide resistance against antibiotics, chloramphenicol and kanamycin.

The tra integration vector (pCON32-20) has to be integrated at the attB site in the chromosome of CON32-16 (FIG. 19). Since the E. coli CON32-16 or pCON32-20 vector doesn't contain the lambda integrase gene that is required for integration the lambda integrase needs to be supplied in trans. The plasmid pJW27 containing a temperature sensitive replicon, and a heat inducible lambda integrase was transformed into E. coli CON32-16. Following this transformation, electrocompetent E. coli CON32-16/pJW27 were prepared. The tra integration vector, pCON32-20, was transformed into the electrocompetent E. coli CON32-16/pJW27 cells. After electroporation the bacterial cells were incubated at 43° C. for 1 hour (to induce the lambda integrase, and also to cure the strain of pJW27) and then spread onto LB agar containing 100 µg/mL of 2,6-diaminopimelic acid and 50 µg/mL kanamycin (Kn, 50 µg/mL). These plates were incubated overnight at 37° C. Resulting colonies were analyzed by PCR to verify the initial integration of pCON32-20 at the attB site using the primer pairs con32-8A with con32-8D (FIG. 19 and Table 7) which would generate a 1987 bp amplicon from the integrant strain, with no amplicon from CON32-16. The PCR-positive clones (those with the integration of pCON32-20 at the attB site) were then grown in LB broth containing 100 µg/mL of 2,6-diaminopimelic acid and 7% sucrose without antibiotics overnight. These cultures were then subcultured for two days in the same medium, followed by dilution and plating on LB agar containing 100 µg/mL of 2,6-diaminopimelic acid and 7% sucrose without antibiotic selection to counter select sacB-containing bacterial cells. This culturing in LB broth with 100 µg/mL of 2,6-diaminopimelic acid and 7% sucrose facilitated the homologous recombination between the ybhC regions (FIG. 19). The homologous recombination should eliminate the immE3-KanR-gamma ori-CamR-sacB portion of pCON32-20A generating a Tra containing strain without any antibiotic marker. The integration and second step homologous recombination of pCON32-20 at the attB site was verified by conjugation efficiency and PCR analysis. A mobilizable plasmid pCON15-49 was transformed into the potential recombinant, and its conjugation efficiency was compared to the well-studied host E. coli S17-1. The efficiencies of conjugation were same between these strains, thus all the tra genes were properly integrated into the host chromosome. A pair of PCR primers, con32-8A and con32-8C, was used to identify the 2$^{nd}$ step, homologous recombination at the ybhC regions. Locations of these primers are indicated in the FIG. 19 above, and their actual sequences are shown in the Table 7 below. PCR analysis using the primers con32-8A and con32-8C will yield a 1695 bp amplicon if the second step homologous recombination event took place. The resulting strain that contains the integrated tra genes was called CON32-27A.

TABLE 7

Sequence of primers used to detect the tra integration

| Primer name | DNA sequence | SEQ ID NO: |
|---|---|---|
| CON32-8A | 5'-TTGTAGTTAGTGTCATTCAGATTGCGCTGT | 27 |
| CON32-8C | 5'-TGCTACTGCTTCGCAATGCTGGAC | 28 |
| CON32-8D | 5'-CAAGAAAGCCATCCAGTTTACTTTGCAG | 29 |

Primer names and corresponding sequences of the primers to detect the integration of the tra genes.

TABLE 8

PCR primer combinations used in PCR analysis to detect the tra integration and subsequent homologous recombination Correct amplicon sizes are shown for the resulting E. coli CON32-27A strain, while amplification of the parental E. coli CON32-16 strain, will not yield any amplicons that will be amplified in the PCR conditions used for detection.
Specific PCR products from recombinant strain CON32-27A

| PCR primer pair | Product size from CON32-27A | Product size from parental strain CON32-16 |
|---|---|---|
| CON32-8A × CON32-8C | 1695 bp | 8897 bp, too large to amplify under the condition used* |

*PCR condition: 94 C.-5 min, (94 C.-30 sec, 59 C.-30 sec, 72 C.-1 min), 72 C.-5 min, 5% DMSO, 1 u/20 uL Taq Genotype of CON32-27A: K-12 E. coli MG1655 ΔmsbB::lacI$^Q$, ΔdapA::immE3-Arc/mnt, ΔaroA::immx10$^7$-lacI$^Q$, attB::tra-P$_L$-Mnt 5. recA Deletion with No Insertion The last genetic alteration to E. coli MG1655 was the deletion of recA without any insertion taking the place of recA. The ΔrecA genotype was introduced to minimize potential genetic instability by recombination, and also to attenuate fitness of the host strain. This was the last genetic alteration to the donor strain since the other deletions and insertions listed above required RecA to help facilitate these genetic deletions and insertion to the donor strains chromosome. The recA gene in E. coli MG1655 was deleted using the standard two-step homologous recombination. The summary of this gene replacement is depicted in the FIG. 21.

TABLE 9

Sequence of primers used to create the suicide vector pCON31-45

| Primer name | DNA sequence | SEQ ID NO: |
|---|---|---|
| Con31-10A | 5'-GTGGATCCGATGCGATCGGTAGCGTG | 30 |
| Con31-10B | 5'-GGTCTAGACCGGGTAATACCGGATAGTC | 31 |
| Con31-10C | 5'-GCGTTGACGATACACAAGGGTCGCATCTG | 32 |
| Con31-10D | 5'-GGAAGCTTGTAGGCTTCGTCGTCGC | 33 |
| Con29-133D | 5'-GCACCAGTCGATGTCACATTC | 34 |
| Con29-133H | 5'-CGTGCTGATTATGCCGTGTC | 35 |

Primer names and corresponding sequences of the primers used to create the suicide vector pCON31-45 and to detect the deletion of recA in the genome.

Construction of the ΔrecA gene deletion suicide vector, pCON31-45 is described here. The 5' and 3' flanking regions of recA were PCR cloned using two pairs of primers, con31-10A/con31-10B, and con31-10C/con31-10D, respectively. The cloned DNA fragments were verified by DNA sequencing. These fragments were assembled into a plasmid pCON31-45 (FIG. 22). This vector has both a selectable marker CamR and counter selective marker sacB on the plasmid. Prior to transformation, pCON31-45 was digested with AscI to eliminate the replication origin (ori) of the plasmid. The replicon-less plasmid was circularized by T4 ligase prior to transforming *E. coli* CON32-27A. Transformants were selected on LB agar containing 2,6-diaminopimelic acid (100 μg/ml) and chloramphenicol (Cam, 50 μg/ml), growing colonies were analyzed by PCR to verify homologous recombination at either 5' or 3' flanking region of recA. The PCR primers used for this analysis are listed in the Table 9 above, and locations of these primers are indicated in the FIG. 21. The candidate colonies containing the integrated pCON31-45 were subsequently grown in LB broth containing 2,6-diaminopimelic acid (100 μg/ml) and 7% sucrose (with no chloramphenicol) overnight. These cultures were then subcultured for 2 days and were diluted and plated on LB agar containing 2,6-diaminopimelic acid (100 μg/ml) and 7% sucrose without chloramphenicol selection to counter select sacB-containing bacterial cells. Colonies growing on these agar plates are either recA-deletion mutants or revertants to the parental strain, and this was screened by PCR using the primer pair listed in the Table 10 below.

Recombined homologous regions are verified by phenotypes (sucrose insensitive, and chloramphenicol sensitive), and PCR products specific to these recombinations. The primers and size of the PCR products are listed in the Table 10 below. In addition to the PCR analysis, phenotype of recA was verified by sensitivity of the strain to UV light. This gene deletion process eliminated 1098 bp of the entire coding region of recA.

TABLE 10

Specific primer combination used in PCR analysis to detect the recA deletion following homologous recombination. Correct amplicon sizes are shown for the resulting *E. coli* CON31-85A strain, while amplification of the parental *E. coli* MG1655 and CON32-27A are 1 kb larger.
Specific PCR products from recombinant strain CON31-85a

| PCR primer pair* | Product size from CON31-85A | Product size from parental strain CON32-27A or WT MG1655 |
|---|---|---|
| Con29-133D Con29-133H | 692 bp | 1779 bp |

Figure 21:
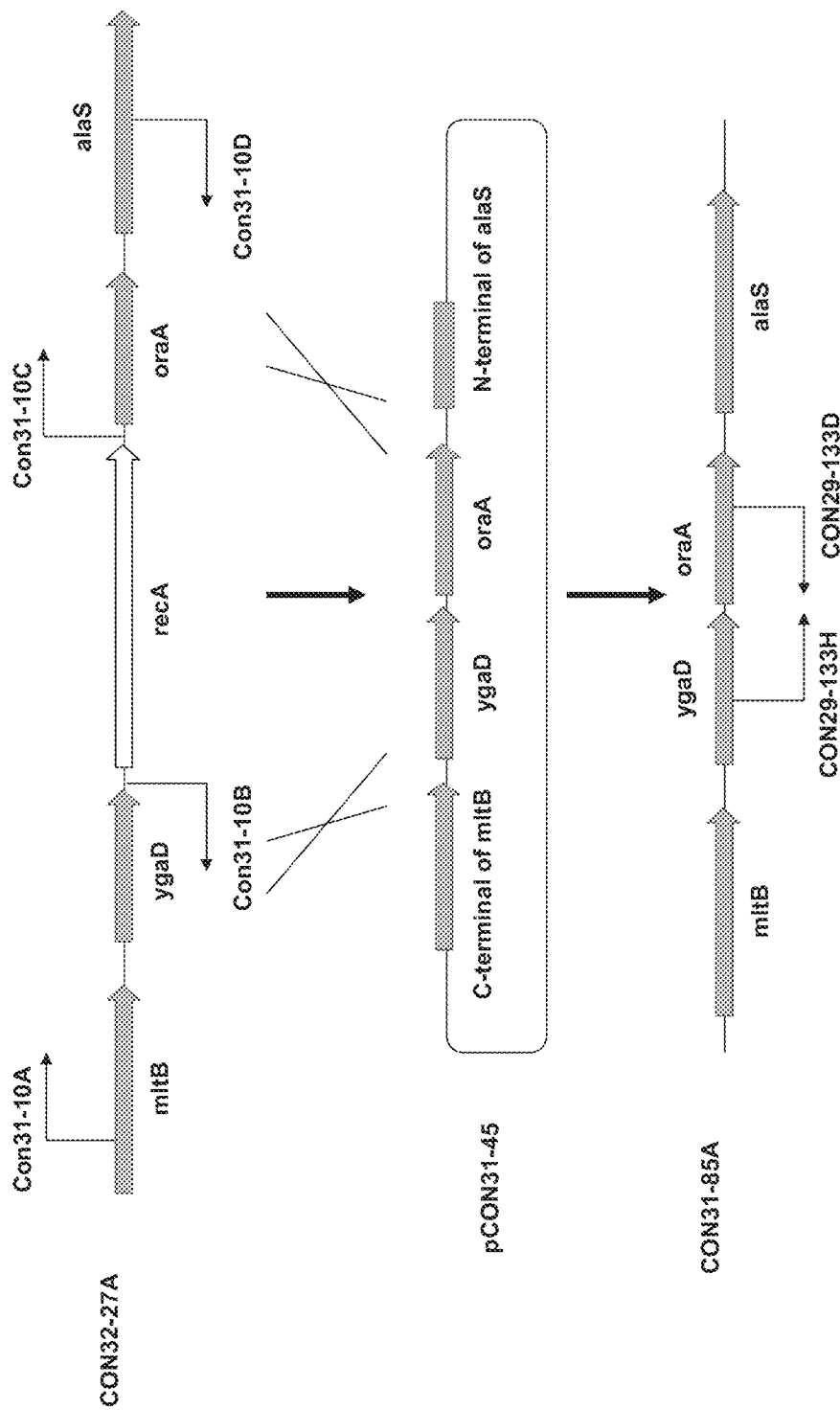
FIG. 21 shows a schematic representation of the two-step homologous recombination event that deletes recA in *E. coli* CON32-27A, using the suicide plasmid pCON31-45.
Figure 22:
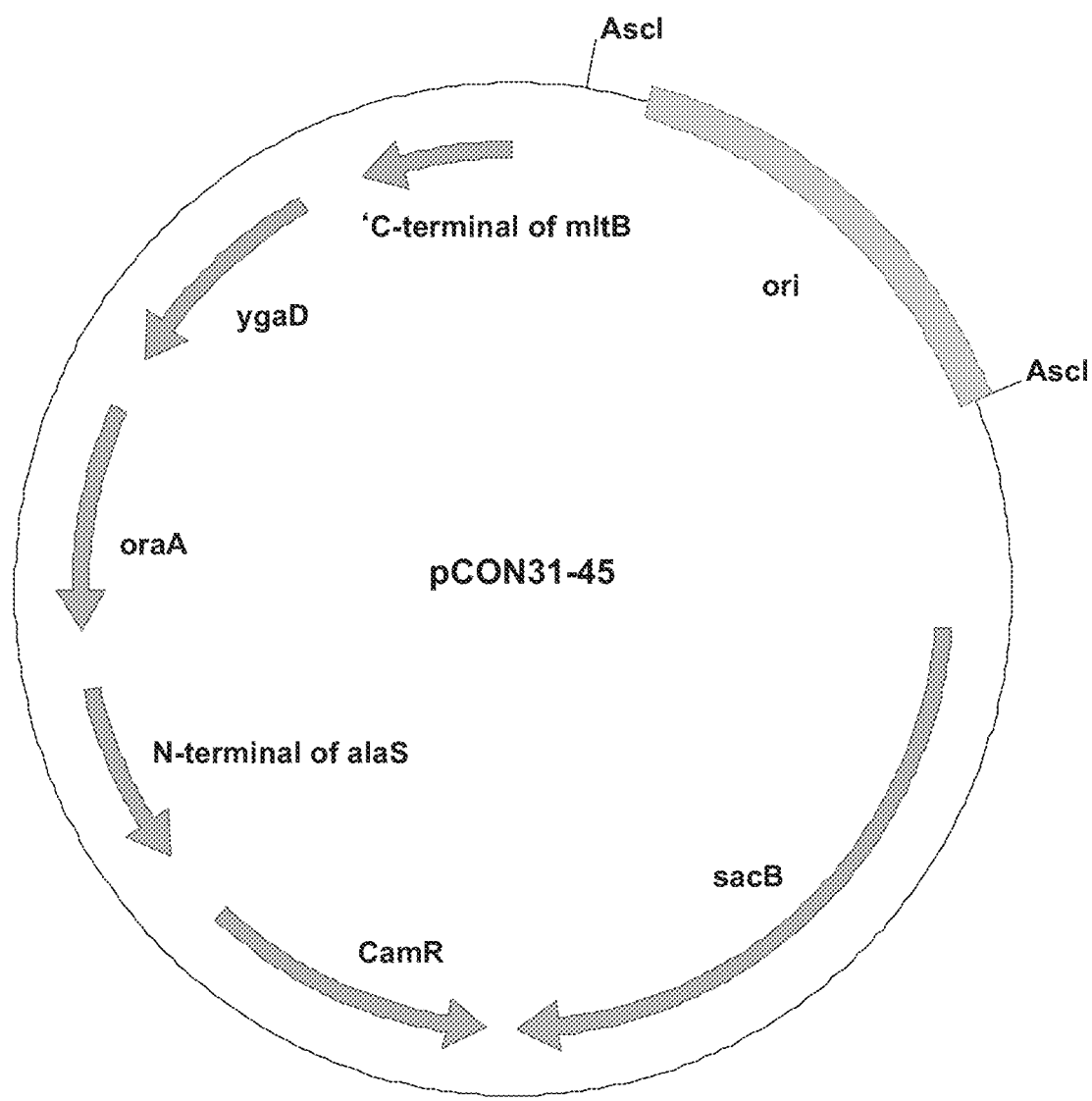
FIG. 22 shows a plasmid map of the pCON31-45 suicide vector used to create the recA deletion in *E. coli* CON32-27A. The C-terminal end of mltB, all ygaD, all of oraA and the N-terminal end of alaS are included in the vector to facilitate homologous recombination. Positive selection gene CamR and counter selective gene sacB are also shown on the map. The ori was excised using AscI restriction enzyme digestion followed by recirculization with T4 DNA ligase prior to transforming *E. coli* CON32-27A. This gene replacement process deleted the majority of the recA coding region.

*See the locations of the primers in the FIG. 21.

Genotype of CON31-85A:
K-12 *E. coli* MG1655 ΔmsbB::lacIQ, ΔdapA::immE3-Arc/mnt, ΔaroA::immx10$^7$-lacIQ, attB::tra-P$_L$-Mnt, ΔrecA
In Vitro Killing of Pathogens with GN-4474

As noted above, *E. coli* CON31-85A transformed with plasmid pCON44-74 is termed "GN-4474." In these experiments, GN-4474 is compared to a negative control strain CON37-55A to assess its effect on killing different target pathogens.

In these sets of experiments, the pathogen strains were all cultured over night from freezer stocks. The GN-4474 and CON37-55A were also cultured overnight from freezer stocks. After overnight growth, the densities of the cultures were standardized spectrophotometrically. Target pathogen was then mixed with either GN-4474 or CON37-55A separately, the suspensions were then pelleted in a centrifuge, supernatant removed, and the resulting "mixed" cell pellet was resuspended in saline. The resulting suspensions were then spotted onto nitrocellulose filter disks that were placed on top of 0.9% saline agar plates, to ensure that no bacterial growth took place directly on the plates themselves. The saline agar plates were then quickly dried in a laminar flow hood, then placed at 37° C. for two hours to allow conjugation to occur.

After two hours, the plates were removed from the incubator, the filter disks (still containing the target pathogen and treatment cells) were removed from the surface of the agar plates and, then placed in 1.5 ml centrifuge tubes containing 1.0 ml sterile saline. The tubes were then vortexed to release the bacterial cells from the filter disks. Serial dilutions were then prepared and plated onto Luria Bertani medium. This medium would allow for growth of all of the pathogens tested (*Klebsiella, Pseudomonas, Acinetobacter, Enterobacter, Escherichia coli*), however, since this medium was not supplemented with 2,6-diaminopimelic acid, neither the GN-4474 nor the CON37-55A control could grow, ensuring that only target pathogen would be recovered. The plates were incubated overnight at 37° C., after which the resulting pathogen colonies were counted. The results are reported as "percent of test strain killed by GN-4474" in FIGS. 24A-24E.

The counts from the CON37-55A negative control plates were used as a baseline. The killing efficiency of GN-4474 was calculated by dividing the cfu/ml of recovered target pathogen treated with GN-4474 by the cfu/ml of recovered target pathogen treated with CON37-55A, multiplied by 100 to give the % surviving bacteria, as shown in FIGS. 24A-24E.

TABLE 11

| Bacterial Species | Number of isolates tested |
|---|---|
| *E. cloacae* | 50 |
| *K. pneumoniae* | 50 |
| *A. baumanii* | 53 |
| *E. coli* | 38 |
| *P. aeruginosa* | 48 |
| Total | 239 |

These data show that the GN-4474 is not limited to treating *P. aeruginosa*, as shown in the examples below, but finds use in treating infection by a range of different pathogens.

Example 2

Treatment of Gram-Negative Bacterial Infections in Burns

These experiments describe the testing of dosages and systems of administration of GN-4474 for inhibition and killing of *P. aeruginosa* MAK1 in burns on mice.

The following describes a standard protocol for testing compositions of the present invention.
A. Standard Debrided Burn Treatment
 a. Day 0 mice are burned in hot water at ~9:00 am generating a full thickness burn. After the burns are cooled and dried the burn is then infected with ~3500 cfus of *P. aeruginosa* MAK1 b. Day 1 (24 hours after burn and start of infection) the burns are debrided and treatments are started with GN-4474 in complete excipient buffer (50 mM $KPO_4$ buffer, 10% trehalose, 2% glycerol and 0.5% HEC) or vehicle control (excipient buffer). Between 1 and 3 applications of either vehicle control or GN-4474 treatment was applied on this day over the course of 8 hours.

c. Day 2 (48 hours after the burn and infection) the mice are sacrificed. Muscle biopsies from the infected burn site are taken. Also spleens (to represent systemic infection) are collected. Tissues are homogenized in sterile LB medium and plated onto LB agar plates for enumeration.

d. Modified protocols tested
   i. Different infection inoculums of *P. aeruginosa* MAK1
   ii. Second days of treatments (both GN-4474 and vehicle control) were performed on Day 2 (48 hours post burn and infection), followed on Day 3 (72 hours post burn and infection) mouse sacrifice and tissue collection.

e. Groups of mice ranged from 8-11 animals each.

f. The experimental animals received third degree 12% TBSA (total body surface area) dorsal scald burn by immersion in 85° C. water for 9 seconds. The 12% TBSA is approximately 20 $mm^2$.

Variations to this protocol and results are discussed below.

Treatment 1

In the first experiment to define the "treatment model," pathogen inoculation times and load are defined. For this experiment, the mice were burned and then infected with 7400 cfu of *P. aeruginosa* MAK1 delivered in a volume of 200 µl on day 0. Twenty four hours later (day 1), four groups of 8 mice each were treated as follows:

Group 1—treated with vehicle control (excipient buffer) only no bandage;

Group 2—treated with a low dose of GN-4474 ($3.78 \times 10^9$ cfu applied to animal wound) in excipient buffer no bandage;

Group 3—treated with a high dose of GN-4474 ($2.91 \times 10^{10}$ cfu applied to animal wound) in excipient buffer no bandage;

Group 4—treated with bandage saturated with excipient buffer only.

On Day 2 (48 hours post infection) the mice were sacrificed, muscle biopsies were taken, homogenized, and plated for viable counts. Spleen were also collected, homogenized, and plated for viable counts.

The *E. coli* GN-4474 that were used for this experiment were grown to the optimal stage of growth (mid logarithmic OD600=1.8). The GN-4474 bacteria were then concentrated just four hours prior to being applied to the debrided burn site. It is noted that prolonged storage in concentrated form reduces conjugation efficiency.

Figure 4:
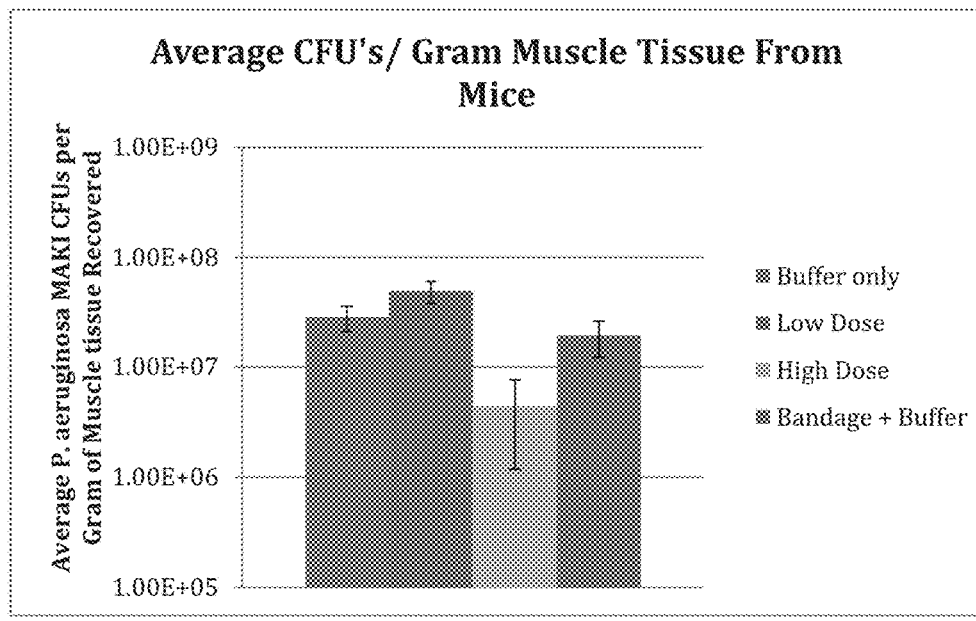
FIG. 4A shows recovered pathogen (*P. aeruginosa* MAK1) from muscle punches after treatments with GN-4474.
FIG. 4B shows recovered pathogen (*P. aeruginosa* MAK1) from spleen tissue after treatments with GN-4474.
Figure 4:
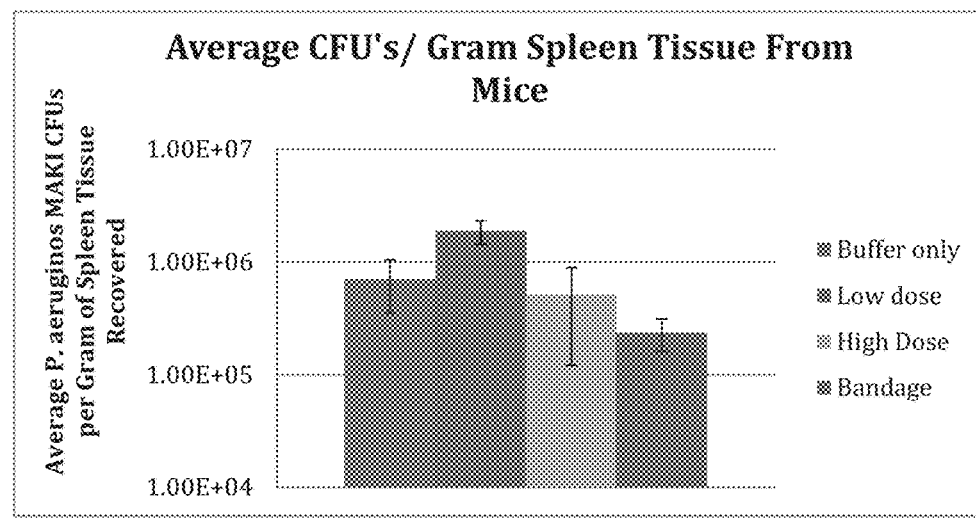

Results are shown in FIGS. 4A and 4B. These data shows that there is a significant difference between use of the high-dose treatment and the use of either the buffer alone, or the bandage+ buffer treatments. Further, as seen in FIG. 4A, there is an observable decrease in the *Pseudomonas* load after the high dose treatment. The low dose treatment group shows no decrease in *Pseudomonas* load.

The spleen data (FIG. 4B) shows there is no difference in *Pseudomonas* loads, indicating that the treatment did not stop sepsis from occurring. However, it was not determined whether sepsis existed prior to treatment, and pre-existing sepsis would not be expected to yield to this topical treatment.

Treatment 2

B. Revised Debrided Burn Treatment

In this experiment, the protocol described in Example 1 was modified by using two different pathogen inoculum amounts to cause the infection. The data from Treatment 1 suggested that too large of a *P. aeruginosa* MAK1 inoculum was used to generate this infection. The *E. coli* GN-4474 that was used for this experiment was prepared virtually identically to those in the prior experiment. The *E. coli* GN-4474 was grown to the optimal stage of growth (mid logarithmic OD600=1.7). The GN-4474 bacteria were then concentrated just four hours prior to being applied to the debrided burn site.

Two groups of eight mice each received a *P. aeruginosa* inoculum of (6893 cfu of MAK1). Two other groups of eight mice each received an inoculum of *P. aeruginosa* MAK1 that was roughly one half of the other two groups (3492 cfu of MAK1). Twenty four hours later (day 1), four groups of 8 mice each were treated as follows:

Group 1—higher inoculum *P. aeruginosa* treated with vehicle control (excipient buffer);

Group 2—higher inoculum *P. aeruginosa* treated with a single dose of GN-4474 ($3.70 \times 10^{10}$ cfu applied to animal wound) in excipient buffer;

Group 3—lower inoculum *P. aeruginosa* treated with vehicle control (excipient buffer);

Group 4—lower inoculum *P. aeruginosa* treated with a single dose of GN-4474 ($3.70 \times 10^{10}$ cfu applied to animal wound) in excipient buffer.

Figure 5:
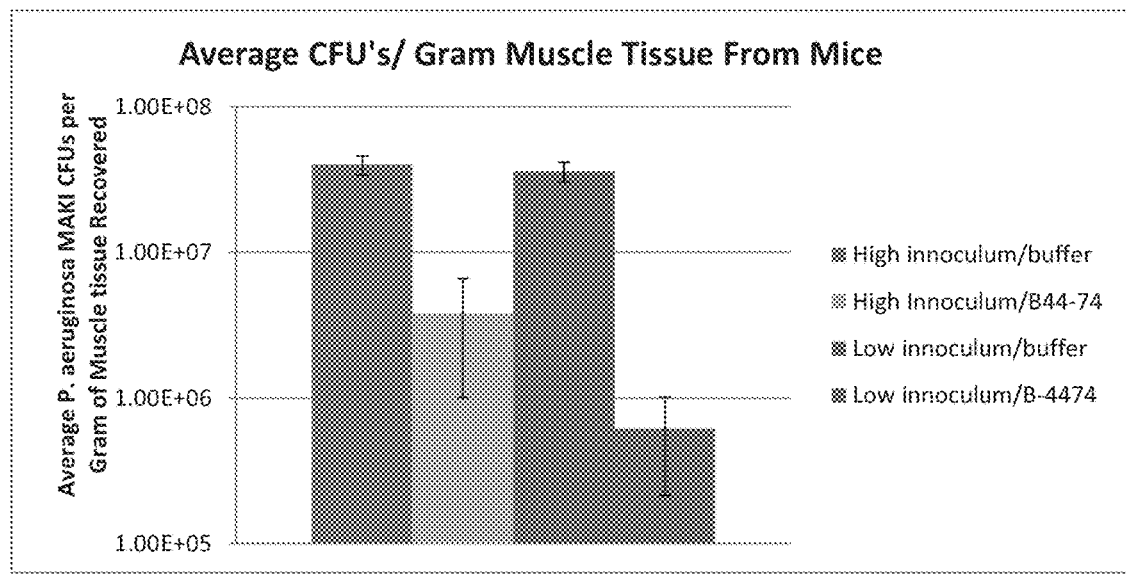
FIG. 5A shows recovered pathogen (*P. aeruginosa* MAK1) from muscle punches using two different *P. aeruginosa* MAK1 inoculums to cause infection subsequently treated with GN-4474 or vehicle control.
FIG. 5B shows recovered pathogen (*P. aeruginosa* MAK1) from spleen tissue using two different *P. aeruginosa* MAK1 inoculums to cause infection subsequently treated with GN-4474 or vehicle control.
Figure 5:
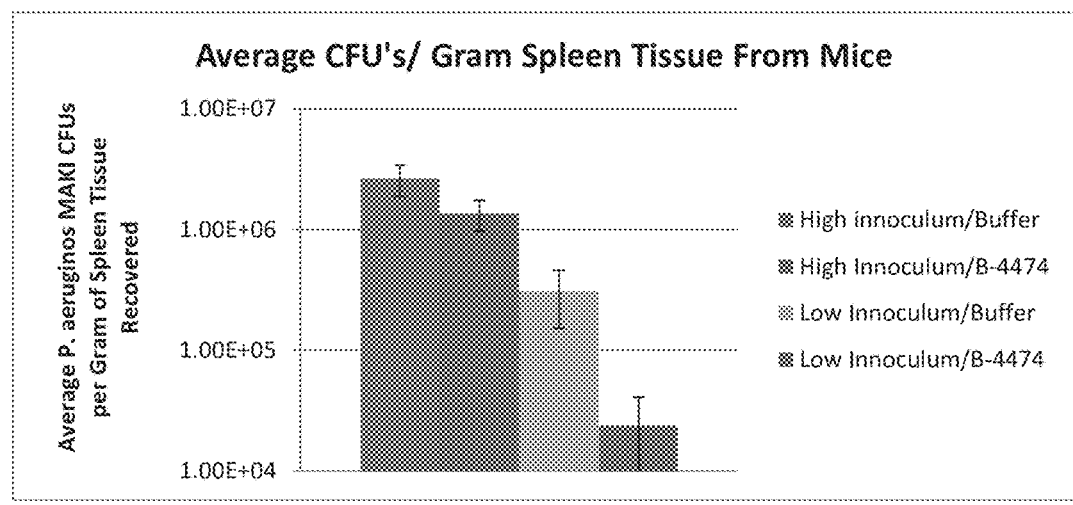

On Day 2 (48 hours post infection) the mice were sacrificed, muscle biopsies were taken, homogenized and plated for viable bacterial counts. Spleens were also collected, homogenized, and plated for viable counts. The results are shown in FIGS. 5A and 5B.

The resulting data shows that the numbers of *P. aeruginosa* MAK1 in the groups that only got excipient buffer as a treatment are just about equal, even when different starting inoculums were used to create the infection (low inoculum versus high inoculum *P. aeruginosa* MAK1). Both infections ended up between $1.7 \times 10^7$ and $3.5 \times 10^7$ cfu (FIG. 5A). When GN-4474 was applied to the high inoculum *P. aeruginosa* MAK1 group, the *P. aeruginosa* MAK1 cfu declined to $3.8 \times 10^6$ cfu. An even greater reduction in residual infection was observed when the same amount of GN-4474 treatment was applied to the low inoculum *P. aeruginosa* MAK1 mice, such that the recovered bacteria were at 6.1 e5 cfu.

When the cfu data from spleens (indicating systemic spread) is examined (FIG. 5B) virtually no difference is seen between the mice that were infected with the high inoculum of *P. aeruginosa* MAK1 strain ($5.6 \times 10^6$ compared to $3.0 \times 10^6$), suggesting that with the high inoculum of *P. aeruginosa* MAK1 being administered, the mice had already started to go septic before treatment with GN-4474 commenced, and the topical application of GN-4474 does not decrease the cfu of systemic bacteria. However, when a lower inoculum of *P. aeruginosa* MAK1 is given to mice to establish an infection, treatment with GN-4474 appears to inhibit or at least decrease the amount of *P. aeruginosa* MAK1 that enters the blood stream, thereby partially inhibiting sepsis (FIG. 5B).

Standardized Low-Inoculum Protocol

The lower dose inoculum of *P. aeruginosa* MAK1 was used for additional characterization of GN-4474 treatments. A standard protocol for additional testing is as follows:

Day 0: Groups of mice are burned and infected with ~3500 cfu of *P. aeruginosa* MAK1.

Day 1: Twenty four hours later, the mice are debrided and treated with GN-4474 or vehicle control (excipient buffer). Depending on the specific experiment being conducted, a single treatment with GN-4474 is performed in the morning (e.g., 9:00 AM). In some experiments, multiple applications of GN-4474 are performed at day 1 (2-3 applications applied between about 9:00 am and 4:00 pm).

Day 2: Then the following day (48 hours post infection) the mice are sacrificed, muscle punches are taken from the burn site, and spleens are collected.

Treatment 3

This experiment examined whether multiple applications of the same concentration of GN-4474 product would decrease the *P. aeruginosa* bacterial load in the burn sites. GN-4474 was prepared grown and concentrated as for Treatments 1 and 2.

Four groups of 8 mice each were burned and infected with 3400 cfu of *P. aeruginosa* MAK1. Twenty four hours later the mice were divided into four groups of eight mice each. The groups were treated as follows:

Group 1—burned, infected with 3400 cfu of *P. aeruginosa* MAK1 and treated with excipient buffer 1×;

Group 2—burned, infected with 3400 cfu of *P. aeruginosa* MAK1 and treated with a single dose of GN-4474 ($1.38 \times 10^{10}$ cfu applied to animal wound) in excipient buffer;

Group 3—burned, infected with 3400 cfu of *P. aeruginosa* MAK1 and treated with excipient buffer 2× (one initially at ~9:00 am and another 5 hours later);

Group 4—burned, infected with 3400 cfu of *P. aeruginosa* MAK1 and treated with two doses of GN-4474 ($1.38 \times 10^{10}$ cfu applied to animal wound) in excipient buffer (one treatment at 9:00 am and another 5 hours later.

On Day 2 (48 hours post infection) the mice were sacrificed, muscle biopsies were taken, homogenized and plated for viable counts. Spleens were also collected, homogenized and plated for viable counts. The data for this set of experiments is shown in FIGS. 6A and 6B.

Figure 6:
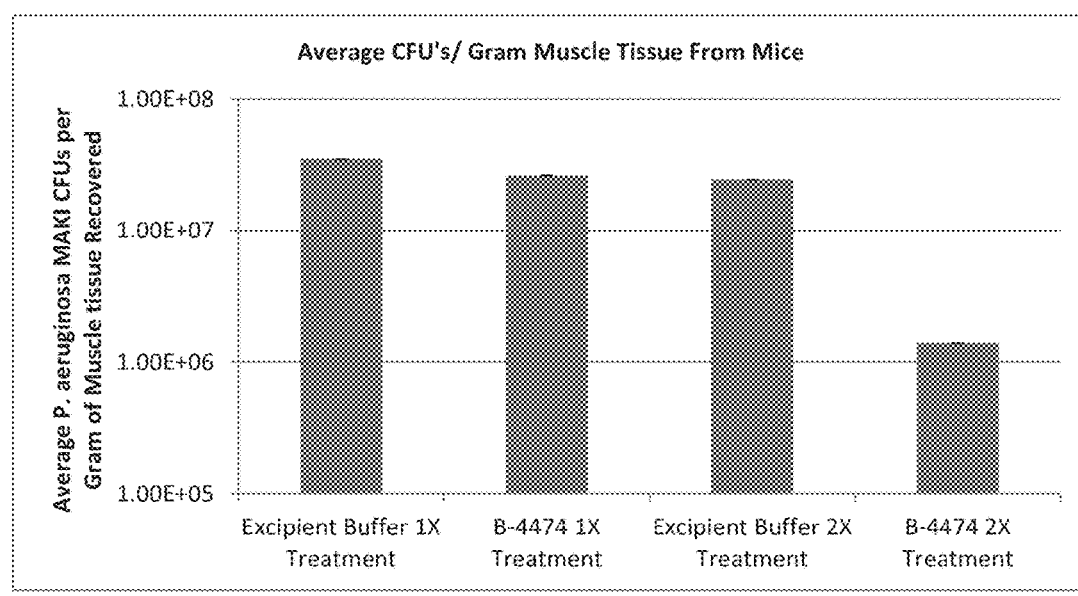
FIG. 6A shows recovered pathogen (*P. aeruginosa* MAK1) from muscle punches after two treatments with GN-4474.
FIG. 6B shows recovered pathogen (*P. aeruginosa* MAK1) from spleen tissue after two treatments with GN-4474.
Figure 6:
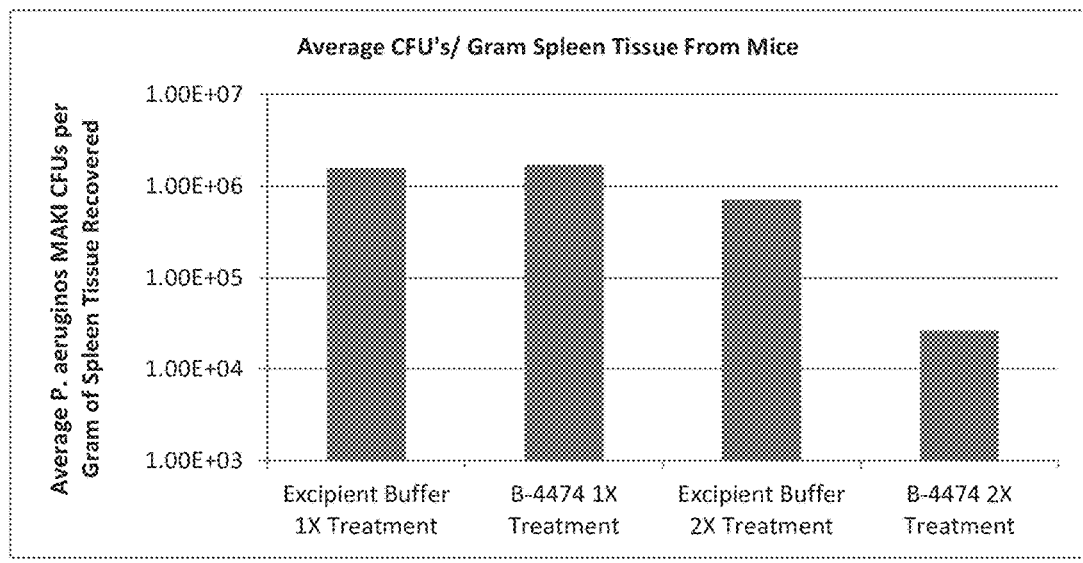

The number of recovered *P. aeruginosa* MAK1 in the group that were treated 1 time with excipient buffer was $3.51 \times 10^7$ cfu/gram of tissue (FIG. 6A). There was a small reduction of *P. aeruginosa* MAK1 ($2.63 \times 10^7$ cfu/gram of muscle tissue in the group that was treated 1 time with $1.38 \times 10^{10}$ CFU of GN-4474. It is noted here that in the previous animal experiment showed better clearing of *P. aeruginosa* MAK1 in the burn sites after a single treatment with GN-4474, where for this experiment clearing was not significant, although it should be noted that the CFUs of GN-4474 that were applied as a treatment were lower than in the previous experiment.

When mice were treated 2 times, approx. 5 hours apart, with GN-4474, there was a significant decrease in *P. aeruginosa* MAK1 in the burn sights compared to the treatment with excipient buffer 2 times. After two treatments with GN-4474, the average *P. aeruginosa* MAK1 cfu/gram of tissue was $1.39 \times 10^6$ cfu/gram of tissue versus $2.45 \times 10^7$ cfu/gram tissue when treated 2 times with excipient buffer (FIG. 6A). It should be noted here that 4 of the 8 mice that received 2 treatments of GN-4474 had burn sites completely cleared of *P. aeruginosa* MAK1, and two of the remaining mice in this group had significant decreases in *P. aeruginosa* MAK1 burden in the burn sites.

A similar trend was observed in the spleen data (FIG. 6B). Again, with only a single treatment of GN-4474, no significant decrease was observed in the number of CFUs of *P. aeruginosa* recovered in the spleens of these mice ($1.70 \times 10^6$ CFU/gram of spleen tissue for the 1 time GN-4474 treatment versus $1.59 \times 10^6$ CFU/gram of spleen tissue for the 1 time excipient buffer treatment) (FIG. 6B).

These data show that one treatment of $1.38 \times 10^{10}$ CFU of GN-4474 does not prevent sepsis, but the mice treated with 2 treatments of GN-4474 had an average *P. aeruginosa* MAK1 burden of $2.63 \times 10^4$ CFU/gram of spleen tissue, while the control group of mice treated with 2 treatments of excipient buffer had an average *P. aeruginosa* MAK1 burden of 7.12 e5 CFU/gram of spleen tissue (FIG. 6B). Five of the eight mice in the 2 times treatment with GN-4474 group had no detectable *P. aeruginosa* MAK1 in their spleens. One of the remaining 3 mice in this group had a significant decrease in *P. aeruginosa* MAK1 burden as well.

Treatment 4

This experiment examined the effect of treating the infected burn site 1×, 2×, and 3× during eight hours. As above, mice were burned and infected with 3500 cfu of *P. aeruginosa* MAK1 at day 0. Then, 24 hours later, the treatments with vehicle control or with GN-4474 commenced. The test groups were as follows:

Group 1 was treated with excipient buffer 1× at 9:00 am;

Group 2 was treated 1× with GN-4474 at 9:00 am;

Group 3 was treated 2× with GN-4474 at 9:00 am and 12:00 pm; and

Group 4 was treated 3× with GN-4474 at 9:00, 12:00 pm and 2:00 pm.

In contrast to the prior treatments, rather than using freshly prepared GN-4474 product for this experiment, resuspended preparation of lyophilized GN-4474 was used.

Using a resuspended vial of GN-4474 significantly altered the dose of GN-4474 that was applied to the wound site. In previous experiments about $1-3 \times 10^{10}$ cfu of freshly cultured GN-4474 was applied to the wound site. In this experiment using resuspended lyophilized GN-4474, 33 times less GN-4474 ($1.1 \times 10^9$ cfu) was applied to each burn site, at each treatment time.

Treatment with the resuspended preparation showed no inhibition or decrease in cfu of *P. aeruginosa* MAK1 recovered from either muscle or spleen tissue, regardless of the number of treatments applied. (data not shown)

Treatment 5

This experiment repeats the protocol of Treatment 3, with the hypothesis that increasing the number of treatments with GN-4474 will continue to decrease the *P. aeruginosa* MAK1 pathogen in the burn site and spleen. This experiment utilized GN-4474 that was grown under a slightly different set of conditions.

Three cultures of GN-4474 were grown and the cultures were stopped at OD600s of 2.2-2.5 and prepared on the morning of the day the animals were to be treated. The cultures were grown longer than optimum and were concentrated early in the morning and stored on ice until application. Four groups of 10 mice each were burned and then infected with 3489 CFU of *P. aeruginosa* MAK1. Twenty four hours later, the eschars were removed and the four groups of 10 mice each were treated as follows:

Group 1—treat one time (1×) with 150 µl of excipient buffer that is pipetted onto the burn site, Group 2—treat with a single dose of ($1.04 \times 10^{10}$ cfu) of GN-4474 applied to the wound site;

Group 3—treat two times (2×) with a dose of ($1.04 \times 10^{10}$ cfu) GN-4474 applied to the wound site, One treatment initially followed by a second treatment GN-4474 2 hours later;

Group 4—treat three times (3×) with a dose (1.04×10$^{10}$ cfu) GN-4474. One treatment initially, followed by a second treatment GN-4474 2 hours later, followed by a third treatment 3 hours after the second treatment (5 hours total).

Figure 7:
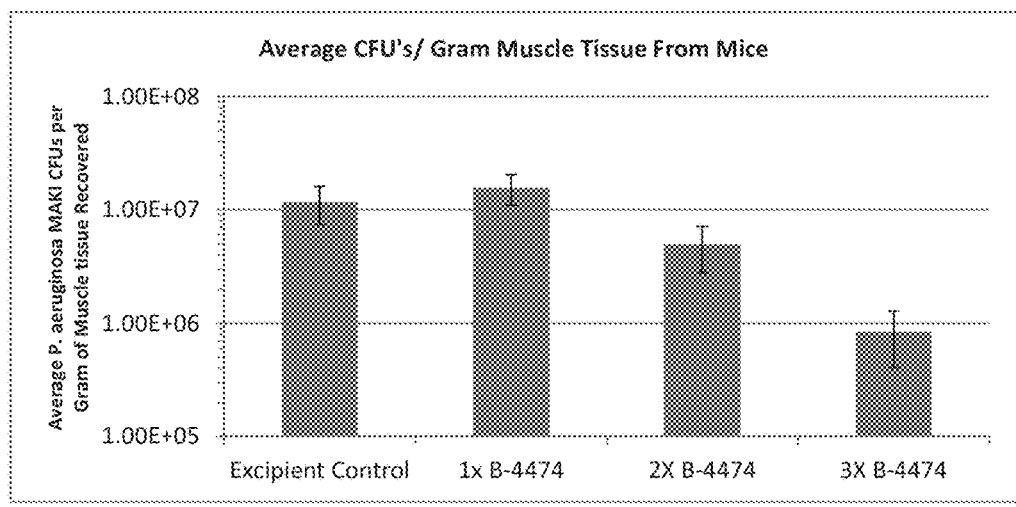
FIG. 7A shows recovered pathogen (*P. aeruginosa* MAK1) from muscle punches after sequential treatments with GN-4474.
FIG. 7B shows recovered pathogen (*P. aeruginosa* MAK1) from spleen tissue after sequential treatments with GN-4474.
Figure 7:
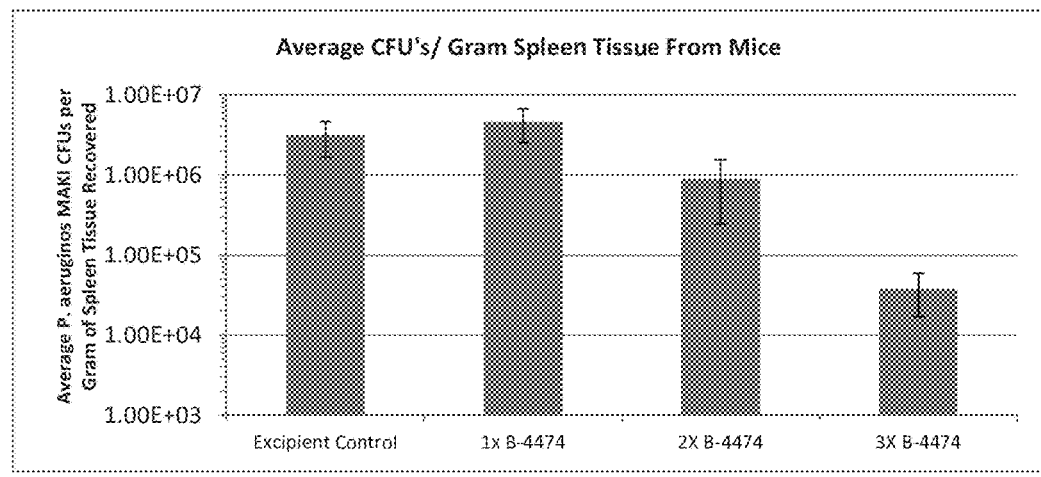

The treated animals were sacrificed and the tissues processed as described above. The results are shown below in Table 12 and 13 and in FIGS. 7A and 7B.

TABLE 12

Recovered pathogen (*P. aeruginosa* MAK1) from muscle punches

|  |  | Mean CFUs/Gm Tissue | Standard Error |
|---|---|---|---|
| Muscle | Excipient Control | 11,744,311 | 4,323,708 |
|  | 1x GN-4474 | 15,619,341 | 4,670,534 |
|  | 2X GN-4474 | 4,959,367 | 2,172,470 |
|  | 3X GN-4474 | 844,225 | 435,054 |

TABLE 13

Recovered pathogen (*P. aeruginosa* MAK1) from spleen tissue

|  |  | Mean CFUs/Gm Tissue | Standard Error |
|---|---|---|---|
| Spleen | Excipient Control | 3,148,364 | 1,476,464 |
|  | 1x GN-4474 | 4,624,565 | 2,076,163 |
|  | 2X GN-4474 | 899,491 | 653,886 |
|  | 3X GN-4474 | 37,587 | 20,754 |

These data show that the pathogen counts in both muscle and spleen tissues decrease with increased numbers of treatments with GN-4474, and that three treatments improves not only burn site infection, it also decreased sepsis, as indicated by the spleen tissue. Three of the ten mice in the 3× group showing no detectable *P. aeruginosa* in the spleen tissue.

These findings all further define the application and dosing procedure for the administering of GN-4474 to infected burns. It was observed that if the burn sites were debrided and left for greater than 16 hours without treatment, the treatment had minimal if any efficacy in clearing the infection. However, if treatment was started shortly after debridement, and then continued at approx. 4 hour intervals, the efficacy of treatment using GN-4474 increased as the concentration of GN-4474 product increased, and as the number of applications increased.

Example 3

Dosing for Treatment of Gram-Negative Bacterial Infections in Burns Using Subeschar Injection This experiment investigated applying the GN-4474 product without debridement, below the burn eschar. In this approach, the eschar is left in place and the GN-4474 product is injected using a needle below the eschar.

The following procedure was used for subeschar injections:

Mice are thermally injured, and then infected with *P. aeruginosa* MAK1, and left for 24 hours. The next day, groups of infected mice are injected using a needle and syringe below the eschar but above the muscle tissue, with either 300 μl of excipient buffer (vehicle control) or 300 μl of resuspended lyophilized GN-4474.

Injection Treatment 1

Lyophilized GN-4474 was resuspended in sterile water. Based on the concentration of GN-4474 in the lyophilized vials, it was calculated that 1.0×10$^9$ cfus of GN-4474 would be injected in the 300 μl of treatment that is injected subeschar in the mice. The two groups of six mice each were treated as follows:

Group 1—burned, infected with *P. aeruginosa* MAK1; left for 24 hours and then treated by injecting 300 μl of 1× excipient buffer below the eschar (vehicle control):

Group 2—burned, infected with *P. aeruginosa* MAK1; left for 24 hours and then treated by injecting a single 300 μl dose of resuspended GN-4474 from a lyophilized vial (1×10$^9$ cfu/300 μl).

Figure 8:
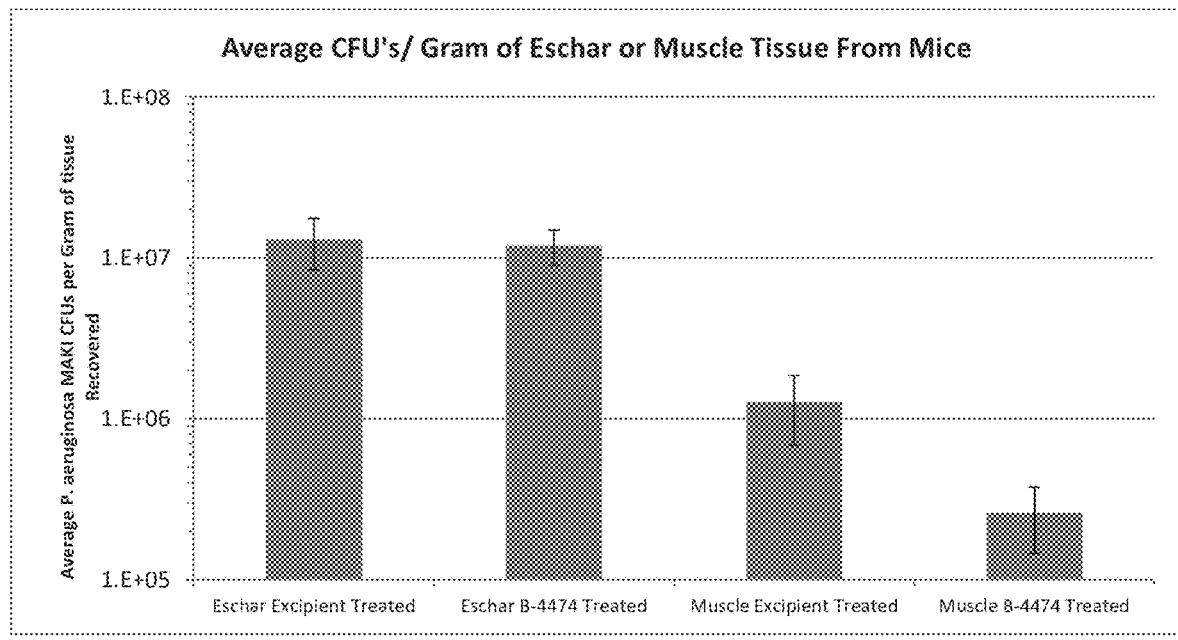
FIG. 8 shows recovered pathogen (*P. aeruginosa* MAK1) from eschar and muscle punches after treatment with GN-4474.

The eschar and muscle tissue of the treated mice was then assayed for recoverable *P. aeruginosa* MAK1. The results are shown in FIG. 8.

These data show that treatment with sub-eschar injection did not reduce the bacterial load in the eschar itself (it wasn't expected to and shouldn't affect the bacterial burden in the eschar itself), but that did significantly reduce the bacterial load in the muscle tissue at the burn site. Further, as compared to the debridement treatment protocol, administering the GN-4474 product below the burn eschar itself led to a significant reduction in *P. aeruginosa* MAK1 bacterial burden in the muscle using significantly less GN-4474 (1.0×10$^9$ cfu), administered in a single-dose treatment. Further, this treatment does not require debridement of the wound.

Example 4

Prevention of Gram-Negative Bacterial Infections in Burns

This experiment examined the prevention of infection by administration of *P. aeruginosa* MAK1 and GN-4474 to wound sites. The mice are treated as follows: Two groups of 4 mice were used, with burning and topical administration as described in Example 2. The mice are then treated as follows:

Group 1—burned, infected with *P. aeruginosa* MAK1; treated with excipient buffer 1× immediately afterwards and Group 2—burned, infected with *P. aeruginosa* MAK1; treated with a single dose of resuspended lyophilized GN-4474 at 5.0×10$^8$ cfu per treatment.

Figure 9:
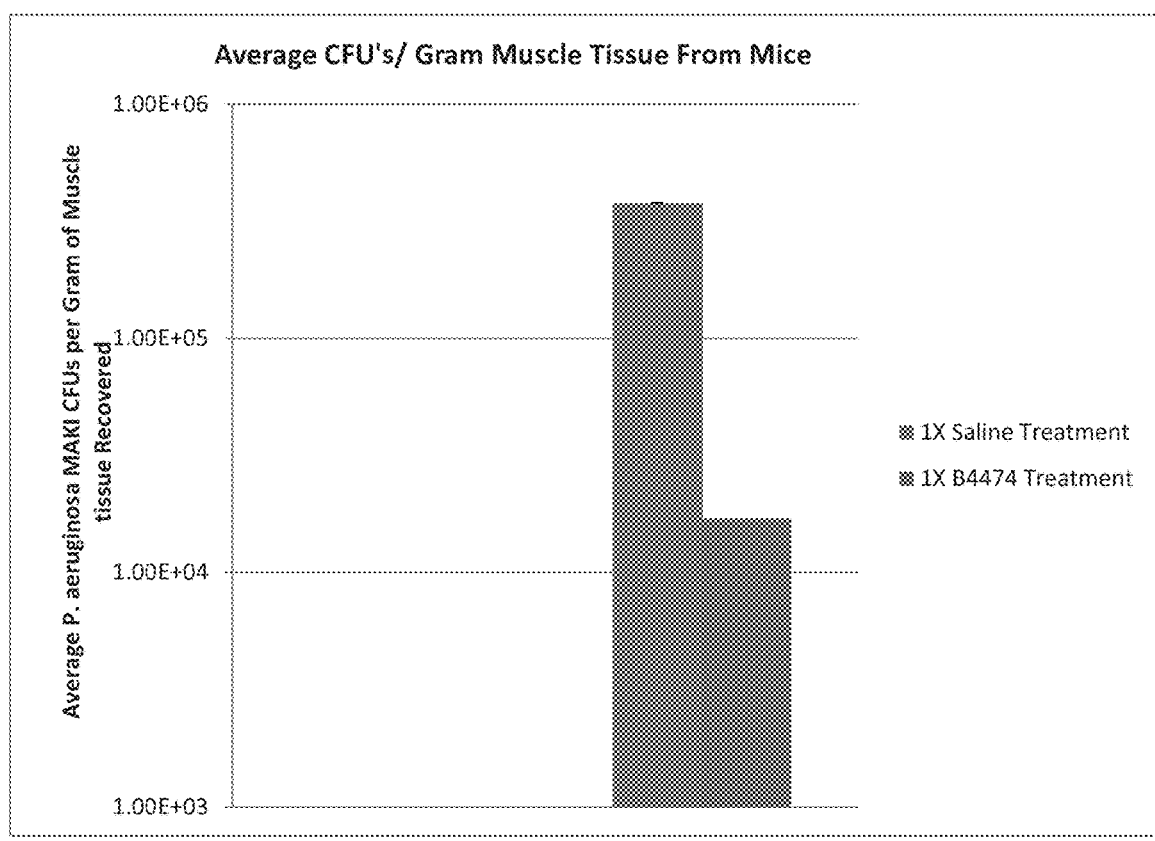
FIG. 9 shows recovered pathogen (*P. aeruginosa* MAK1) from muscle punches after co-application of GN-4474 or a saline control with *P. aeruginosa* MAK1.

The data are shown in FIG. 9. These data show that immediate treatment with GN-4474 significantly reduced infection by *P. aeruginosa* MAK1, even when the GN-4474 was used in a single dose and at a lower concentration than was observed to be effective for pre-existing infections described in Example 1.

A single treatment with 5.0×10$^8$ GN-4474 resulted in a 1.5 log decrease in pathogen numbers in the burn site during this prevention model. This same treatment amount resulted in a greater than 90% survivability.

Example 5

Dose Response of Single Dose Treatments of Murine Burn/Sepsis Model

This experiment looked at dose-response of mice treated with different amounts of GN-4474 immediately after burn injury and infection.

The experimental animals received third degree 12% TBSA (total body surface area) dorsal scald burn by immersion in 85° C. water for 9 seconds. *Pseudomonas aeruginosa* PA14 was then applied topically to the burn wound. The pathogens were allowed to absorb into the burn wound, then GN-4474 was applied to the burn surface. The majority of this solution was absorbed into the burn wound as well. The mice are followed for 10 days and moralities were tracked.

The mice were infected with between $1 \times 10^4$ and $1 \times 10^5$ cfu of pathogen (*P. aeruginosa* or *Acinetobacter baumannii*) prior to treatment with the indicated doses of GN-4474. The results are shown in FIG. 23.

For mice infected with *P. aeruginosa*, approximately 50% survival of mice occurred with treatment with $6.0 \times 10^5$ cfu of GN-4474. Approximately 75% survival was achieved with treatment with $7.0 \times 10^6$ cfu of GN-4474. Greater than 85% survivability was achieved with treatment with $5 \times 10^7$ cfu of GN-4474. Greater than 90% survivability was achieved with $5 \times 10^8$ cfu of GN-4474 and 100% survivability was achieved with doses of $4.9 \times 10^9$ cfu or greater.

Similar numbers were observed when *Acinetobacter baumannii* was the target pathogen used to infect the burn sites.

The animals were sacrificed and biopsies were taken analyzed for surviving pathogens at the treatment site.

These data show that GN-4474 prevents death in the mice, and the biopsies showed that the GN-4474 treatments cleared the wound site of pathogens in a dose-dependent manner.

Example 6

Dosing for Treatment and Prevention of Gram-Negative Bacterial Infections in Burns Using Bandages For these experiments, GN-4474 is formulated into a thin gel to adhere to bandages, dressing, and for application directly to wound sites. Note the formulation of the gel used in these experiments is the same formulation used in the animal infection and prevention studies.

A single concentration (1001 µl of 10-3 dilution of standardized) *P. aeruginosa* was determined to be effective in generating a complete lawn of bacteria on the agar surface, if no treatment was present. The 100 µl of 10 e-3 dilution of standardized *P. aeruginosa* PA14 is spread on all LB agar plates. The GN-4474 was prepared and applied as follows:

1. GN-4474 is grown to OD600=1.5 The 1.0 L culture of GN-4474 was pelleted in 4 separate 250 ml centrifuge bottles at 6000 rpm for 15 minutes.
2. Decant the supernatent and resuspend each GN-4474 cell pellet in 25.0 mls of complete 1× excipient buffer. Combine the resuspended pellets together. This in now concentrated 10×.
3. Prepare a 1× GN-4474 formulation by diluting the 10× GN-4474 ten times in excipient buffer (2.5 mls of 10× GN-4474 into 22.5 mls of sterile excipient buffer).
4. Prepare a 0.1×GN-4474 formulation by diluting the 1× GN-4474 ten times in excipient buffer (2.5 mls of 1× GN-4474 into 22.5 mls of sterile excipient buffer).
5. Take 12 of the LB agar plates that was previously spread with 100 µl of the 10-3 dilution of standardized PA14.
6. Completely soak three separate 1"×1" 10 ply wide mesh bandages in 1× excipient buffer. (A 1"×1" 10 ply wide mesh bandage should hold ~2.0 mls when completely soaked. Place a single soaked bandage onto each of three separate LB agar plates that were spread with the PA14.
7. Repeat step 6 using three separate 1"×1" 10 ply wide mesh bandages that were completely soaked in the 0.1× GN-4474.
8. Repeat step 6 using three separate 1"×1" 10 ply wide mesh bandages that were completely soaked in the 1.0× GN-4474.
9. Repeat step 6 using three separate 1"×1" 10 ply wide mesh bandages that were completely soaked in the 10.0× GN-4474.
10. Take the remaining 12 LB agar plates that was previously spread with 100 µl of the 10-3 dilution of standardized PA14 and use these for the "overlay" part of the experiment.
11. Take three of these LB agar plates that was spread with the PA14 dilution and pipette 625 µl of 1× excipient buffer onto the surface in the middle of these three agar plates and immediately place a dry 1"×1" 10 ply wide mesh bandage on top of the spot of excipient buffer.
12. Take three more of these LB agar plates that was spread with the PA14 dilution and pipette 625 µl of 0.1× GN-4474 onto the surface in the middle of these three agar plates and immediately place a dry 1"×1" 10 ply wide mesh bandage on top of the spot of 0.1× GN-4474.
13. Take three more of these LB agar plates that was spread with the PA14 dilution and pipette 625 µl of 1.0× GN-4474 onto the surface in the middle of these three agar plates and immediately place a dry 1"×1" 10 ply wide mesh bandage on top of the spot of 1.0× GN-4474.
14. Take the last three of these LB agar plates that was spread with the PA14 dilution and pipette 625 µl of 10× GN-4474 onto the surface in the middle of these three agar plates and immediately place a dry 1"×1" 10 ply wide mesh bandage on top of the spot of 10× GN-4474.
15. Place all plates into the 37° C. incubator for two hours. Do not invert the plates and rather keep the agar side face up.
16. Carefully remove each bandage from the agar surface of all plates and return the plates agar facing up to the 37° C. incubator for overnight incubation.
17. After 16-18 hours of total incubation remove the plates and visualize.

Figure 10:
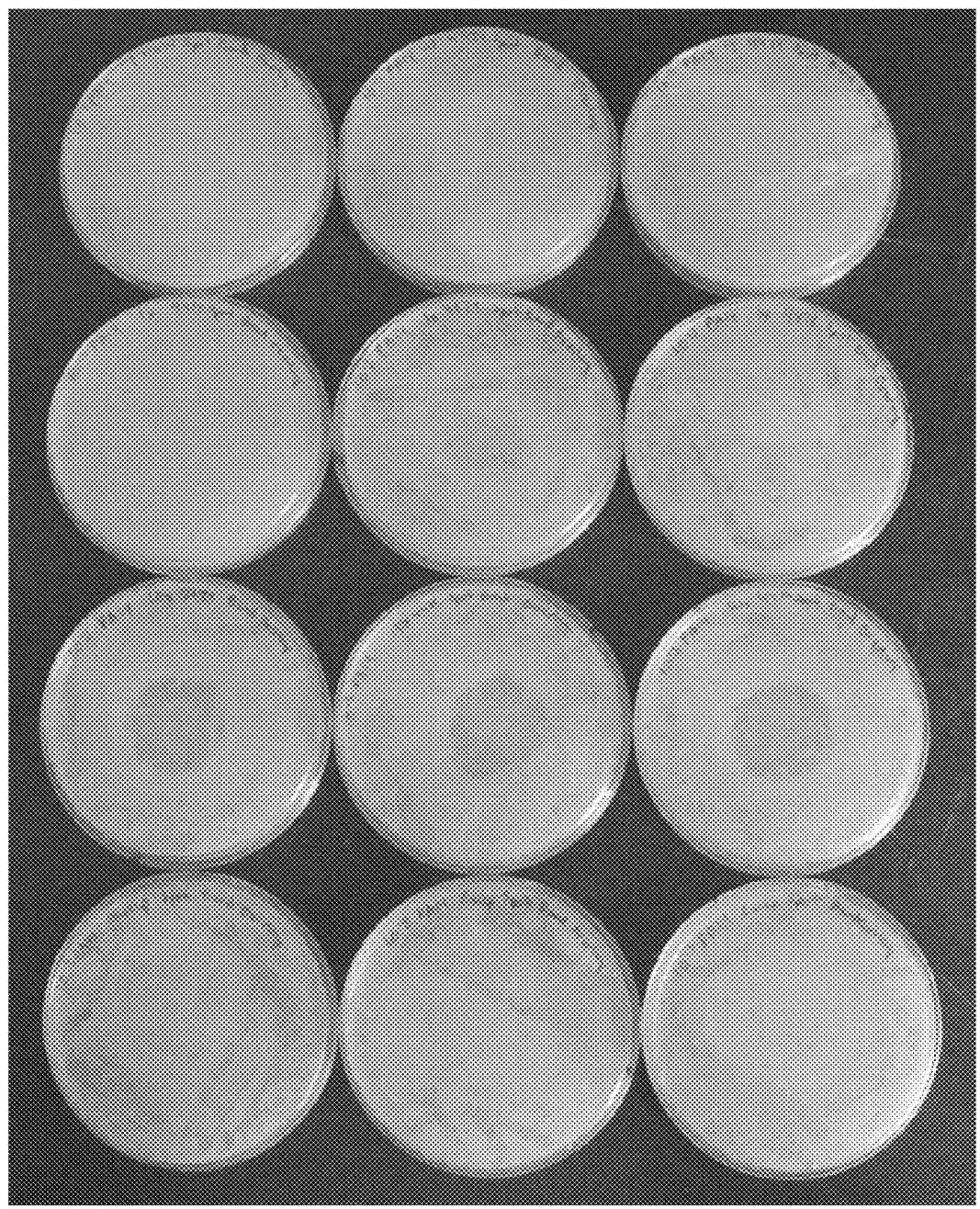
FIG. 10 shows culture plates in which different amounts (cfus) of GN-4474 have been applied to a bacterial lawn and subsequently covered with a bandage dressing to assess killing effects of different doses.

FIG. 10 shows the results of direct application of GN-4474 to the agar surface prior to placement of the bandage, with rows A-D as follows:

A. 0.1× Test Plates: 100 µl of PA14 (10-3) spread onto LB agar plate. 625 µl of 0.1× GN-4474 in excipient buffer (~$2 \times 10^7$ cfu/ml) was spotted onto the surface and a 1 in×1 in 10 ply wide mesh bandage was overlaid on top of the treatment, this was incubated at 37° C. for 2 hrs.
B. 1× Test Plates: 100 µl of PA14 (10-3) spread onto LB agar plate. 625 µl of 1× GN-4474 in excipient buffer (~$2 \times 10^8$ cfu/ml) was spotted onto the surface and a 1 in ×1 in 10 ply wide mesh bandage was overlaid on top of the treatment; this was incubated at 37° C. for 2 hrs.
C. 10× Test Plates: 100 µl of PA14 (10-3) spread onto LB agar plate. 625 µl of 10× GN-4474 in excipient buffer (~$2 \times 10^9$ cfu/ml) was spotted onto the surface and a 1 in ×1 in 10 ply wide mesh bandage was overlaid on top of the treatment; this was incubated at 37° C. for 2 hrs.
D. Control Plates: 100 µl of PA14 (10-3) spread onto LB agar plate. 625 µl of complete excipient buffer was spotted onto the surface and a 1 in ×1 in 10 ply wide mesh bandage was overlaid on top of the treatment, this was incubated at 37° C. for 2 hrs.

The bottom row, the controls having no GN-4474, show that the bandages themselves did not detectably inhibit growth of P. aeruginosa. It is clear in the plates in row C that the application of the 10× concentration of GN-4474 produced a clear zone on the plates indicative of inhibition or killing of the P: aeruginosa. The plates in row B, having $\frac{1}{10}^{th}$ the dosage, show a clearer zone in at least one plate, suggesting a dose-related effect of the treatment.

Figure 11:
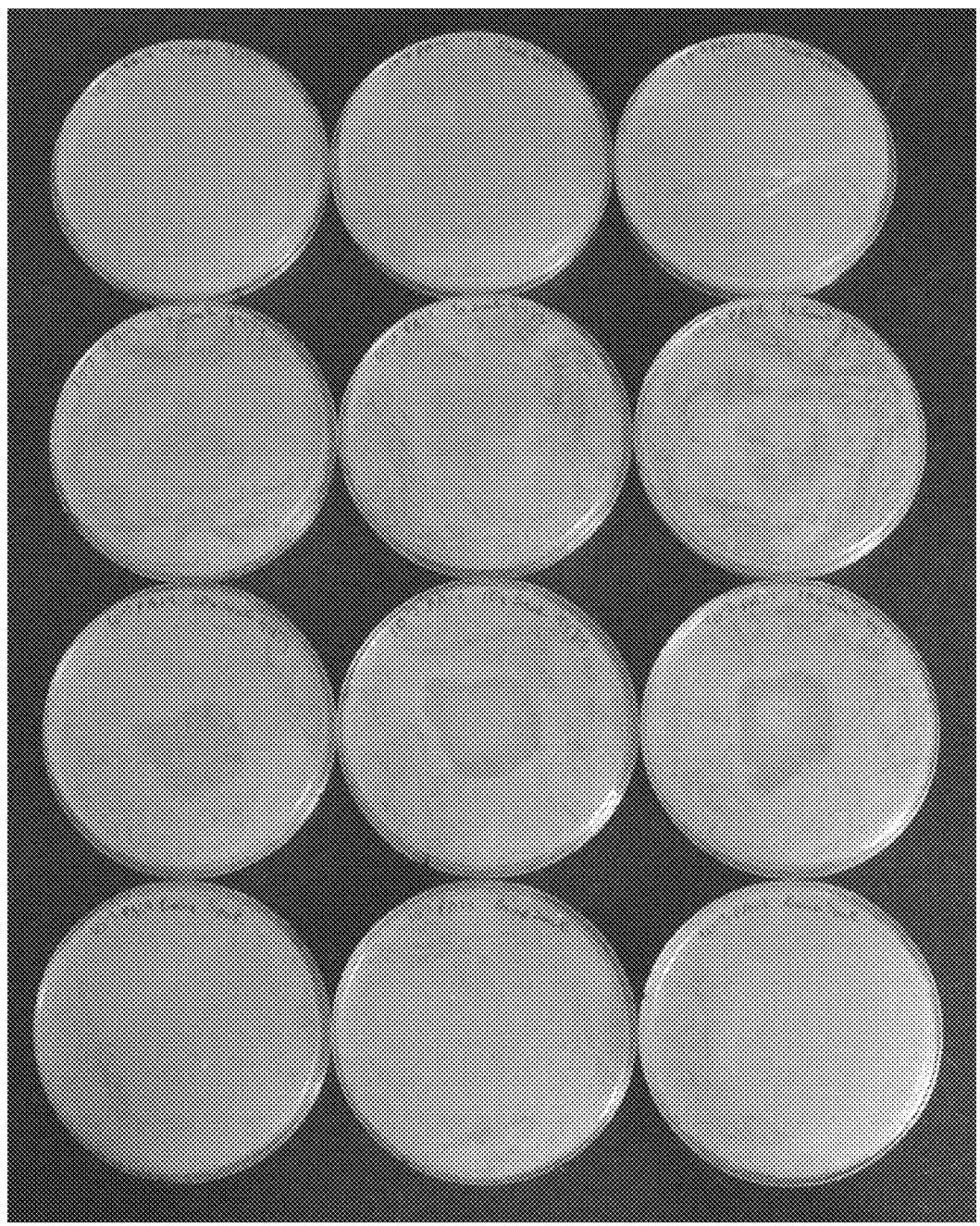
FIG. 11 shows culture plates in which different amounts (cfus) of GN-4474 have been applied to a bacterial lawn by applying bandage dressings that were presoaked with different amounts (cfus) of GN-4474 to assess killing effects of different doses.

FIG. 11 shows the results of soaking the bandages in preparations of B-4744 prior to placement on the agar surface, with rows A-D as follows:

A. 0.1× Test Plates: 100 µl of PA14 (10-3) spread onto LB agar plate. A 1 in ×1 in 10 ply wide mesh bandage soaked in 0.1× GN-4474 (~2×10$^7$ cfu/ml) in excipient buffer was placed onto the surface of the spread agar plate, which was incubated at 37° C. for 2 hrs.

B. 1.0× Test Plates: 100 µl of PA14 (10-3) spread onto LB agar plate. A 1 in ×1 in 10 ply wide mesh bandage soaked in 1× GN-4474 (~2×10$^8$ cfu/ml) in excipient buffer was placed onto the surface of the spread agar plate, which was incubated at 37° C. for 2 hrs.

C. 10× Test Plates: 100 µl of PA14 (10-3) spread onto LB agar plate. A 1 in ×1 in 10 ply wide mesh bandage soaked in 10× GN-4474 (~2×10$^9$ cfu/ml) in excipient buffer was placed onto the surface of the spread agar plate, which was incubated at 37° C. for 2 hrs.

D. Control Plates: 100 µl of PA14 (10-3) spread onto LB agar plate. A 1 in ×1 in 10 ply wide mesh bandage soaked in complete 1× excipient buffer was placed onto the surface of the spread agar plate, which was incubated at 37° C. for 2 hrs.

The bottom row, the controls having no GN-4474, show that the bandages themselves did not detectably inhibit growth of P. aeruginosa. It is clear in the plates in row C that the application of the bandages soaked in the 10× concentration of GN-4474 produced a clear zone on the plates indicative of inhibition or killing of the P. aeruginosa. The plates in row B, having $\frac{1}{10}^{th}$ the dosage, show a clearer zone in all three plates, suggesting a dose-dependent effect of the treatment.

The experiments described in which GN-4474 is applied directly to the agar were repeated using different types of bandage materials, including: 1 ply fine mesh, a 2 ply, 4 ply and 10 ply wide mesh, 10 ply fine mesh, and a 6 ply with a "wavy appearing" wide mesh. The result were very similar to the data shown in FIGS. 10 and 11, with the 10× applications showing a cleared zone, and with the 1× dilutions of GN-4474 showing little effect (data not shown). None of the bandage materials alone inhibited growth of the P. aeruginosa lawn, and none appeared to have an effect on the killing ability of the GN-4474 composition.

Example 7

Short Term Storage: 4° C.

Figure 25:
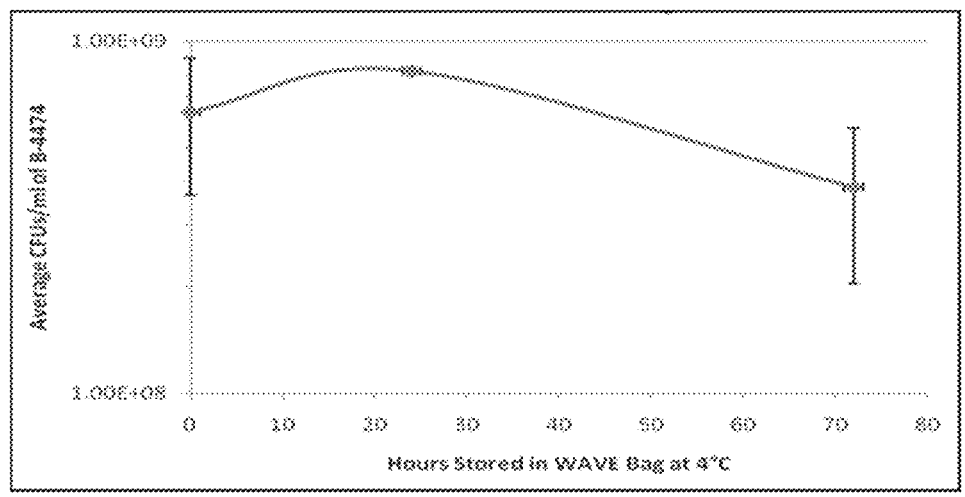
Figure 25:
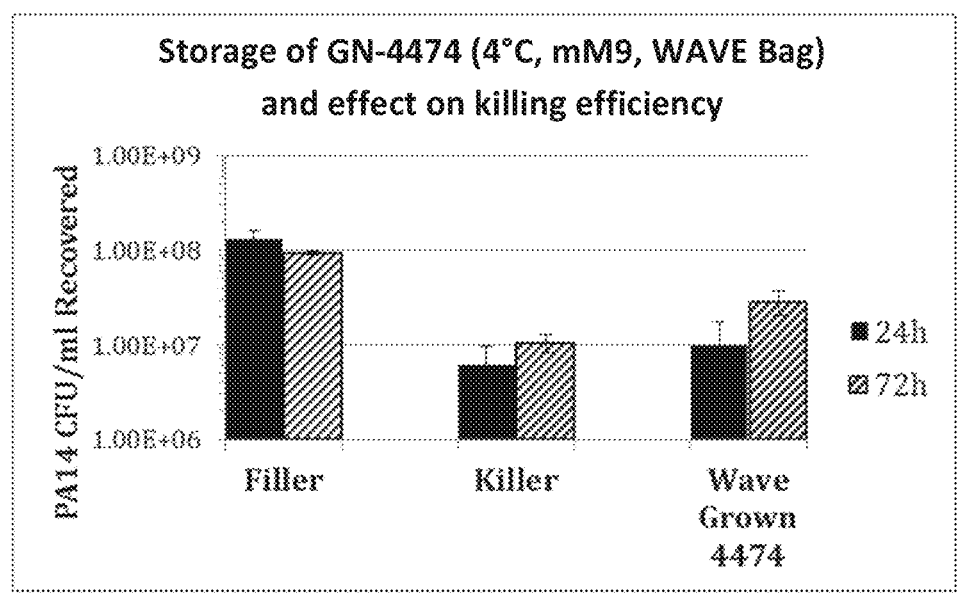

The stability (viability and conjugation competence) of GN-4474 grown to the late-exponential phase of growth (the stage of growth at which the cells would normally be harvested) and then transferred to a 4° C. refrigerator was examined. Bacteria were kept in the growth chamber in spent medium at a concentration of ~6×10$^8$ cfu/ml. As shown in FIG. 25A, no significant decrease in the viability of cells was observed at 24 h or at 72 h. However, as shown in FIG. 25B, the ability of GN-4474 to efficiently kill P. aeruginosa strain PA14 in an in vitro assay is slightly reduced after storage at 4° C. for 72 h. For this experiment, neither pH nor dissolved oxygen could be controlled using this particular bioreactor.

To examine the effects of concentration, bacteria were grown to the late exponential phase of growth in the GE Healthcare WAVE system, harvested, and resuspended in complete excipient buffer (10% trehalose+2.0% glycerol+0.5% hydroxyethylcellulose all in 50 mM potassium phosphate buffer, pH 7.0) to various concentrations as follows: [Low]=~5.0×10$^8$ cfu/ml; [Low-High]=~5.0×10$^9$; [Medium-High]=1.0×10$^{10}$ cfu/ml; and [High]=~5.0×10$^{10}$ cfu/ml. Bacteria were stored on ice, in the refrigerator at 4° C. Aliquots (triplicate) were removed from each of the four concentrations, at time points corresponding to Day 1 (24 h), Day 2 (48 h), Day 3 (72 h), Day 6 (144 h), Day 7 (168 h), and Day 10 (240 h); viability of the bacteria (FIG. 26A) and in vitro killing efficiency (FIG. 26B) were determined.

Figure 26:
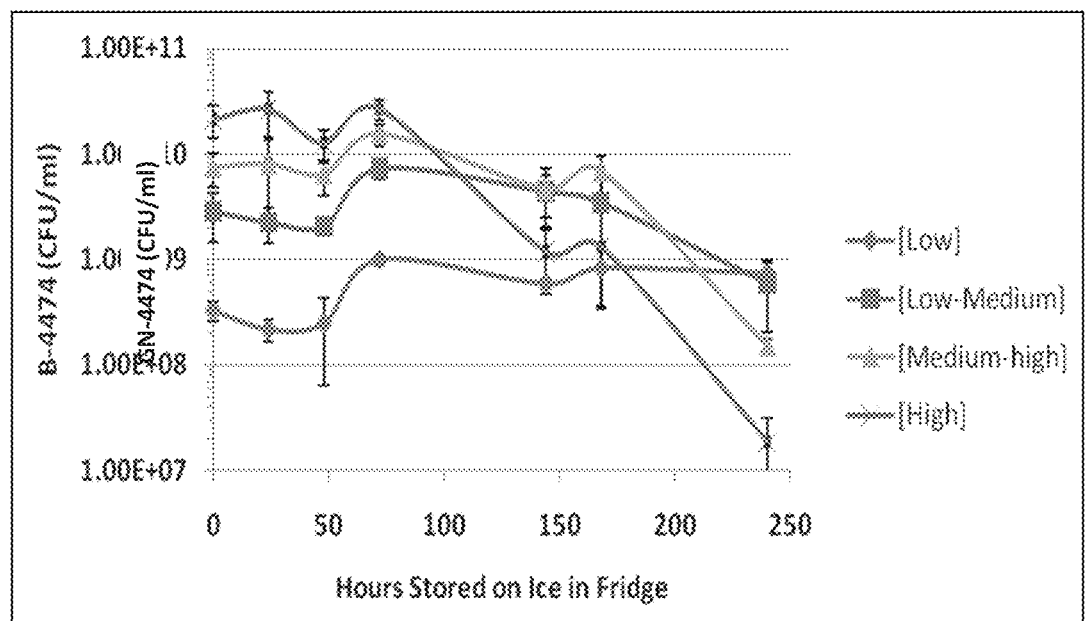
FIGS. 26A and 26B show the effects of bacterial concentration during short term storage on viability and conjugation efficiency of GN-4474.
Figure 26:
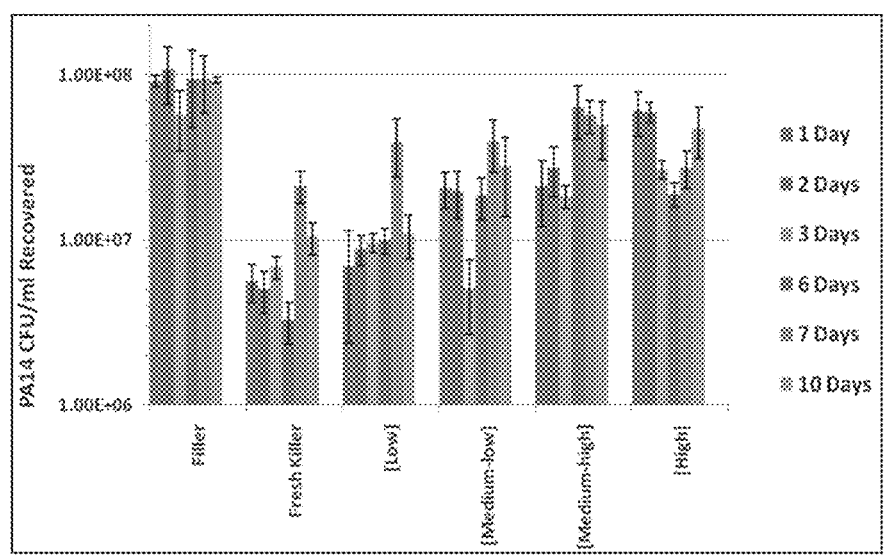

As seen in FIG. 26A, the GN-4474 bacteria remained viable for up to 72 hours (3 days) at all concentrations. However, by 144 hours (6 days) the [High] was showing a significant decrease in viability. By 10 days, only the [Low] of GN-4474 remained wholly viable with no significant decrease in viability whereas the bacteria at the other three doses had begun to die. Similarly, the data presented in FIG. 26B shows that the in vitro killing by GN-4474 ([Low]) was unchanged from Day 1 through Day 10 (with the exception of anomalous data points on Day 7 for both the [Low] sample and fresh killer control reactions). The largest decrease in in vitro killing was obtained from the [High] concentration of GN-4474. When stored at the [High] concentration, GN-4474 lost the ability to effectively conjugate after only 24 hours of storage.

Other experiments show E. coli GN-4474, when stored in excipient buffer at a concentration of 1×10$^{10}$ cfu/ml or higher is not stable in terms of viability, and that omission of hydroxyethylcellulose did not reduce the viability or killing ability of the stored cells. Based on viability data and in vitro killing data, this data suggests bacterial concentrations should preferably be maintained at <10$^9$ cfu/ml for short term storage.

Example 8

Storage Formulations

The effects of different storage media and buffer formulations for short term storage were investigated. In this experiment the E. coli GN-4474 was stored in an excipient buffer without the hydroxyethylcellulose gelling agent (50 mM KPO$_4$ buffer pH7.0, 10% w/v trehalose, 2% (w/v) glycerol and 0.5% (w/v)) or in spent M9 media. The effects that different storage buffer compositions have on both short term storage viability and conjugation efficiency were examined.

GN-4474 was grown under optimum conditions (50% dissolved oxygen, and pH 7.0) to an O.D.$_{600\ nm}$=1.8) and the cells were stored in three ways: 1) in spent medium, leaving the cells in the Cultibag without centrifugation; 2) in spent medium, but transferred to sterile conical tubes, pelleted, and resuspended in the supernatant to control for centrifugation; and 3) pelleted by centrifugation and resuspended in the lyophilization excipient buffer described above. Data are shown in FIGS. 27A and 27B.

Figure 27:
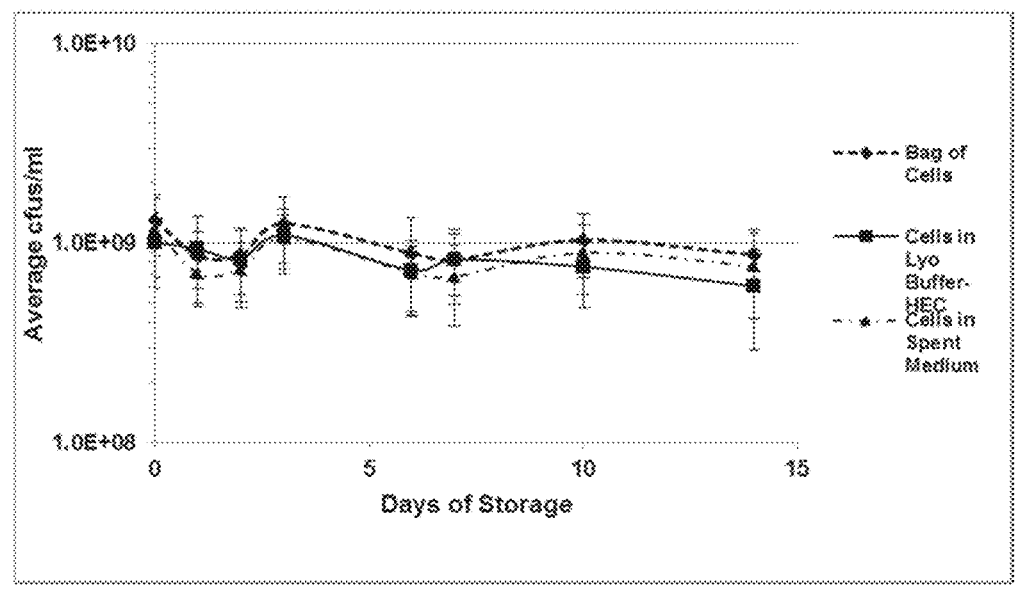
Figure 27:
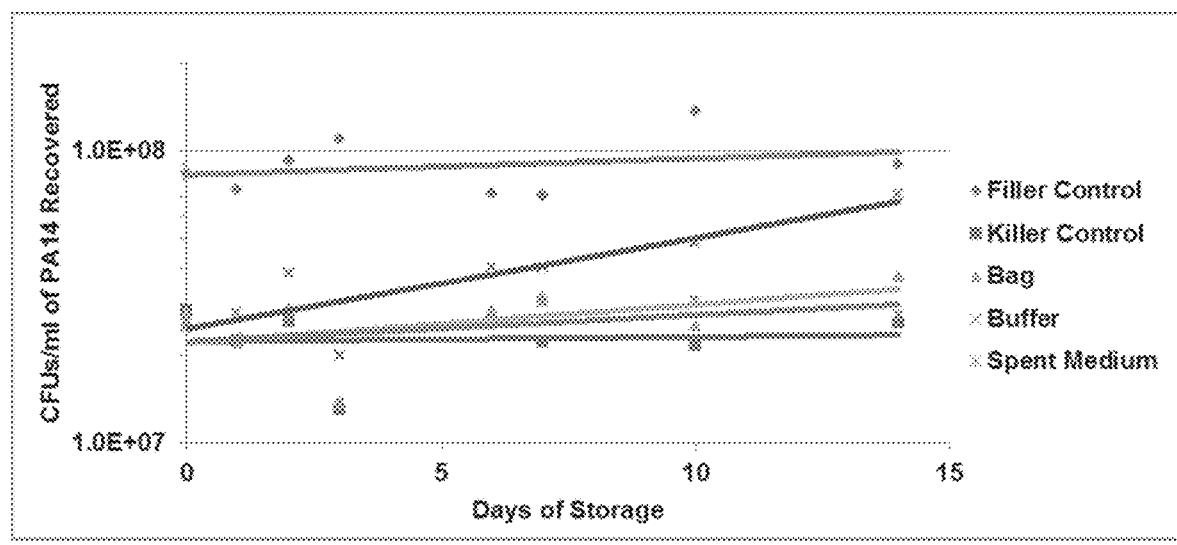

As shown in FIG. 27A, there was no significant decrease in viability of GN-4474 stored in spent medium (in the bag or in another container) or in the excipient buffer described above over 14 days at 4° C., as long as the concentration of GN-4474 is at 1×10$^9$ cfu/ml. It was observed over multiple experiments that, as long as the concentration of E. coli is maintained at or below 1×10$^9$ cfu/ml, viability of the bacteria at 4° C. can be maintained in spent medium, or in excipient buffer with or without HEC.

As shown in FIG. 27B, there was no noticeable difference in the efficiency of conjugation-based killing as measured by our in vitro assay for bacteria stored in spent medium. Surprisingly, the bacteria stored in excipient buffer showed a decrease in efficiency of conjugation-based killing within 24 hours and the efficiency continued to decrease over time.

In preferred embodiments, short term storage buffer will not be substantially different than the final excipient(s) buffer in which GN-4474 is frozen, with or without lyophilization. One buffer formulation identified for freezing purposes (10% trehalose+2.0% glycerol+0.5% hydroxyethylcellulose all in 50 mM potassium phosphate buffer, pH 7.0). Other formulations were tested for short-term storage purposes.

During development of the technology, one of component examined was the sugar or sugars present, e.g., glucose, sucrose, and trehalose. Viability data indicated that storage of GN-4474 in any of these buffers at −20° C. had modest protective effect. After just three days of storage at −20° C., the viability of GN-4474 was reduced by more than 70% in each of the three sugar-containing buffers, although viability of GN-4474 stored in these same buffers at 4° C. was much better than samples stored at −20° C. After three days in either 10% sucrose (100% recovery) or 10% trehalose (96% recovery) there was no loss of viability. Viability in 10% glucose was not as good (only 44% of the GN-4474 was viable after three days). Viability of GN-4474 decreased at days 5 and 7, in either 10% trehalose or 10% sucrose.

Addition of glycerol into the buffered sugar storage solutions was tested and the viability and in vitro killing efficiency of GN-4474. GN-4474 was stored at 4° C. in one of the following four sugar- and glycerol-containing, 50 mM phosphate buffers:
10% sucrose+1% glycerol;
10% sucrose+2% glycerol;
10% trehalose+1% glycerol; and
10% trehalose+2% glycerol.

GN-4474 stored in 10% sucrose+1% or 2% glycerol had good initial survivability, but viability decreased starting on day 3. From Day 1 to Day 2, recovery of GN-4474 in 10% sucrose+1% or 2% glycerol dropped from 84% to 59% or from 104% to 76% respectively (Table 2 and FIG. 3). There was no significant decrease in viability of GN-4474 in 10% trehalose+1% or 2% glycerol for 3 days. By Day 6, viability of GN-4474 decreases in either buffer.

TABLE 14

|  | Day 0 | Day 1 | Day 3 | Day 6 | Day 7 | Day 10 |
| --- | --- | --- | --- | --- | --- | --- |
| 10% Sucrose 1% Glycerol | 100.00 | 83.94 | 59.09 | 56.76 | 38.14 | 56.15 |
| 10% Sucrose 2% Glycerol | 100.00 | 104.13 | 76.48 | 68.16 | 33.97 | 34.28 |
| 10% Trehalose 1% Glycerol | 100.00 | 104.69 | 107.55 | 25.79 | 18.36 | 9.77 |
| 10% Trehalose 2% Glycerol | 100.00 | 169.96 | 150.19 | 41.68 | 22.67 | 12.93 |

The in vitro killing data confirms that GN-4474 stored at 4° C. is effective when stored in trehalose+1 or 2% glycerol or sucrose plus 1 or 2% glycerol. As discussed above, as long as the concentration of E. coli is maintained at or below 1×10$^9$ cfu/ml, viability and killing efficiency of the bacteria stored at 4° C. can also be maintained in spent growth media.

Example 9

Freezing Preparations of GN-4474

Experiments were conducted to examine the stability of GN-4474 frozen in excipient buffer. Controlled chilling and freezing was compared to snap freezing, with respect to maintaining viability and conjugation-based killing ability upon extended storage in a frozen state, at −20° C. or at −80° C.

Controlled Freezing

For these experiments, the GN-4474 was formulated in 50 mM KPO$_4$ buffer, 10% trehalose, 2% glycerol and 0.5% hydroxyethylcellulose. Following overnight storage at 4° C., the GN-4474 culture in spent medium was removed and agitated by hand to make sure the bacteria were fully suspended. The GN-4474 bacteria were then washed and concentrated to ~3×10$^{10}$ cfu/ml in complete excipient buffer. The concentrated GN-4474 in tubes were then subjected to the following chilling and freezing protocol/parameters.
1. Tubes were transferred to the 4° C. incubator, and cooled for 90 minutes.
2. The thermostat on the incubator was changed to −10° C. (82 minutes was required for the incubator to reach −10° C.).
3. The samples were incubated at −10° C. for 90 minutes (Some vials remained unfrozen).
4. All vials were transferred to a −20° C. freezer, and stored at −20° C. until analyzed for viability and in vitro killing efficiency.

Analysis of 'Controlled Frozen' Product:

Control cultures of E. coli GN-4474 (Positive control) and E. coli CON37-55 (Negative control), as well as P. aeruginosa PA14 (Target pathogen) were initiated the day prior to each time point that was monitored (days 0, 1, 2, 5, 6, 15, 27, 45, 51 and 65) and cultured overnight. The following day, the control cultures were placed on ice when the OD$_{600\ nm}$ between 1.5 and 1.9. The P. aeruginosa PA 14 culture usually had on OD$_{600\ nm}$ between 3.0 and 4.0. A single 1.0 ml aliquot of frozen GN-4474 in excipient buffer was removed from the −20° C. freezer and placed at room temperature for 1 hour prior to use in either viability testing or in vitro killing experiments.

Viability as Determined by Serial Dilutions and Viable Counts:
1. Sterile saline was used to prepare 10 fold serial dilutions of the thawed controlled frozen GN-4474.
2. Two separate dilution series were prepared through 10-8 dilution for each sample to be tested
3. Serial dilutions of 10$^{-5}$, 10$^{-6}$, 10$^{-7}$ and 10$^{-8}$ for the vials were plated on LB+Dap plates.
4. A single 10$^{-1}$ dilution from each dilution series was plated on LB agar to look for contamination.
5. The plates were placed in the 37° C. incubator to allow for colony growth (~48 hours).

Killing Efficiency as Determined by In Vitro Filter Based Conjugation Killing Assays:

In vitro killing assays (with target pathogen P. aeruginosa PA14), using the positive and negative control cultures as well as the thawed frozen GN-4474 in excipient buffer, were performed according to the standard protocol. The positive control, negative control and test thawed controlled frozen GN-4474 in excipient buffer had their volumes and concentrations adjusted to an $OD_{600\ nm}$=5.0 to standardize the inputs for the assay. Each in vitro killing reaction (PA14+ negative control, PA14+positive control, and PA14+thawed controlled frozen GN-4474 in excipient buffer) was performed in duplicate. Time points tested were 0, 1, 2, 5, 6, 15, 27, 45, 51 and 65 days stored at −20° C.

Figure 28:
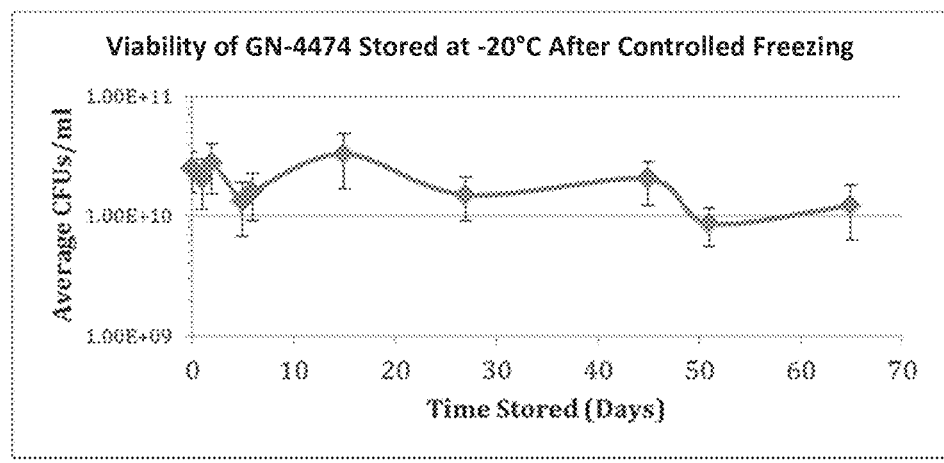
FIG. 28A-28C show the effects of controlled freezing on long-term viability and killing efficiency of GN-4474.
Figure 28:
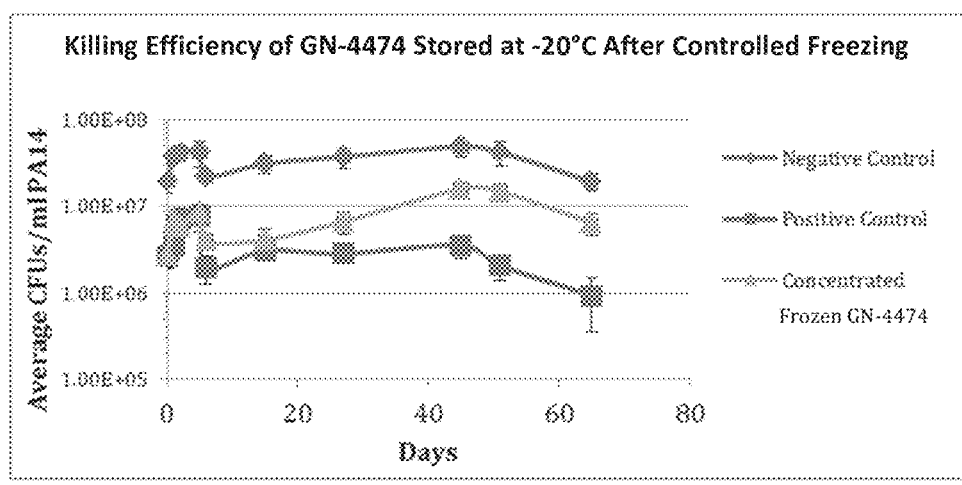
Figure 28:
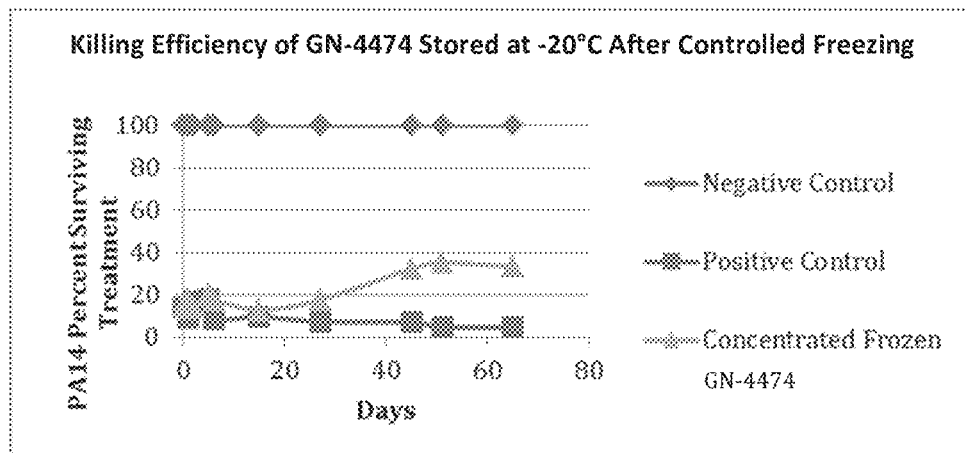

Resulting viability and conjugation efficiency results from the Controlled Freezing experiments are shown in FIGS. 28A-28C. The viability of these 'controlled frozen' samples of GN-4474 remained stable throughout the course of the experiment (65 days post freezing and storage at −20 C). FIG. 28A shows the viability of all samples examined throughout the 65 day time course remained between $9 \times 10^9$ cfu/ml and $3.0 \times 10^{10}$ cfu/ml (all within standard deviation of each other). Based solely on this viability data the 'controlled freezing' protocol that was tried worked quite well to stabilize and maintain viability of frozen GN-4474 cells in excipient buffer.

The in vitro killing efficiency data shown in FIGS. 28B-28C clearly show that freshly cultured positive control (GN-4474) killed target *P. aeruginosa* PA14 pathogen as expected, with surviving PA14 never exceeding 20%. The controlled frozen samples of GN-4474 killed target PA14 pathogen to similar levels as positive control freshly cultured GN-4474 through the first 27 days of storage. However, the stored controlled frozen GN-4474 samples started to lose their conjugation based killing efficiency after ~30 days of storage. Frozen samples of GN-4474 were checked for in vitro killing efficiency intermittently to 65 days of storage. It was confirmed that the in vitro killing efficiency of these samples decreased significantly after ~30 days, and remained less effective until the experiment was stopped at day 65.

Snap Freezing

Following overnight storage at 4° C., the GN-4474 culture in spent medium was removed and agitated by hand to make sure the bacteria were fully suspended. The GN-4474 bacteria were then washed and concentrated to ~$1 \times 10^{10}$ cfu/ml in complete excipient buffer (50 mM $KPO_4$ buffer, 10% trehalose, 2% glycerol and 0.5% HEC). The formulated GN-4474 was aliquoted (10.0 ml) into 15 ml polypropylene conical tubes. A dry ice/ethanol bath was prepared, and the aliquots were submerged in this bath until the sample was completely frozen (90 sec.) After 'snap freezing' the aliquots were transferred to a −80° C. freezer for storage.

Figure 29:
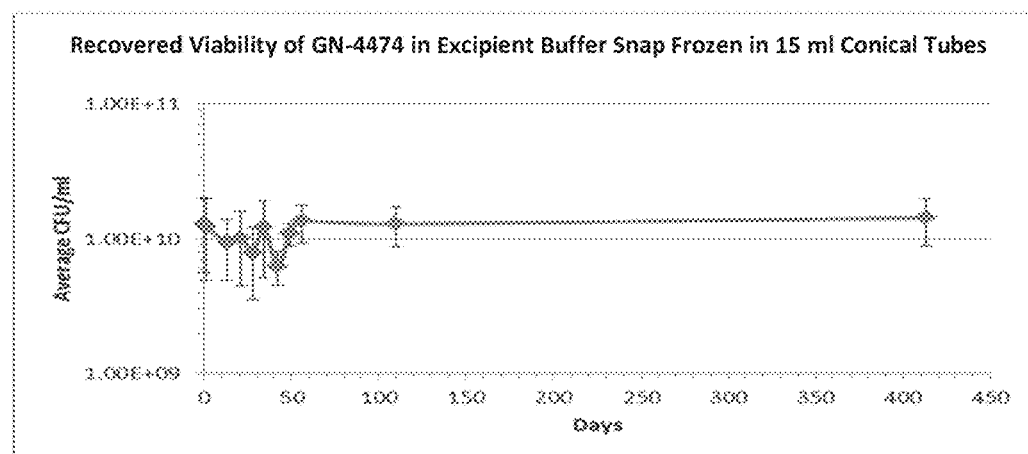
FIGS. 29A and 29B show the effects of snap freezing in 15 ml polypropylene tubes on long-term viability and killing efficiency of GN-4474.
Figure 29:
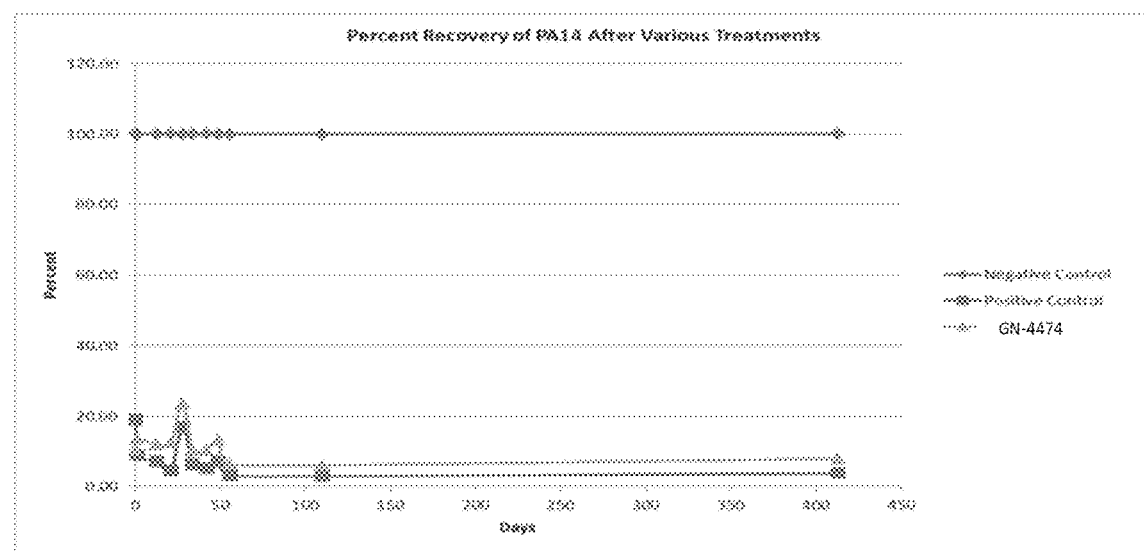
Figure 30:
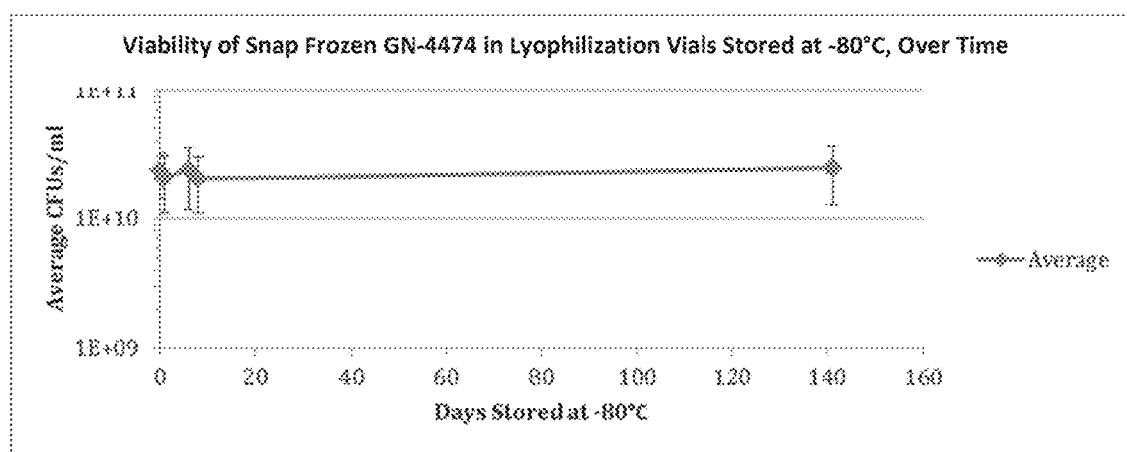
FIGS. 30A-30C show the effects of snap freezing in glass vials on long-term viability and killing efficiency of GN-4474.
Figure 30:
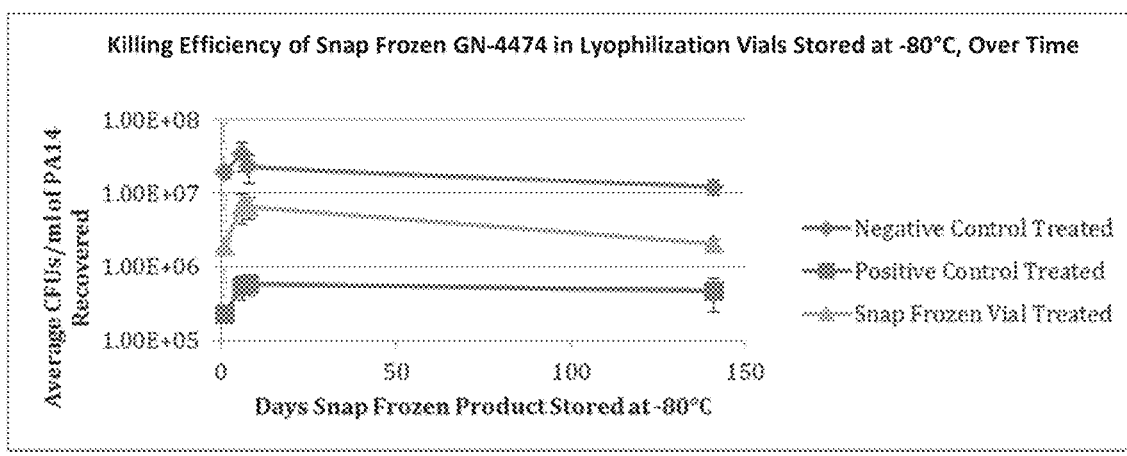
Figure 30:
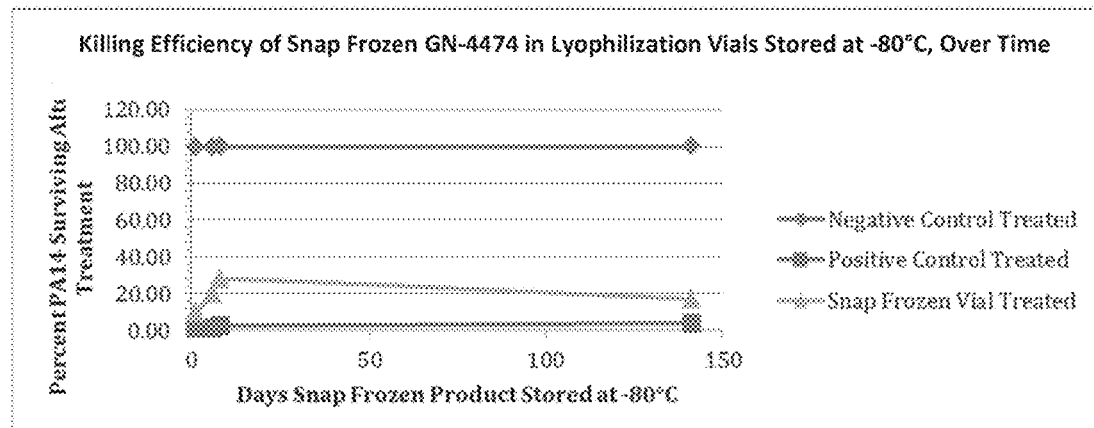

Viability and killing efficiency of frozen samples are analyzed as described above. Resulting viability and conjugation efficiency results from this Snap Freezing experiment are shown in FIGS. 29A and 29B. The viability of these snap-frozen samples of GN-4474 remained consistent (~$1 \times 10^{10}$ cfu/ml) throughout the course of this of the experiment (410 days post freezing and storage at −80° C.). FIG. 29A shows the viability of all samples examined throughout the 410 day time course remained between $6.3 \times 10^9$ cfu/ml and $1.4 \times 10^{10}$ cfu/ml (all within standard deviation of each other). Based solely on this viability data the snap-freezing protocol that was tried worked quite well to stabilize and maintain viability of frozen GN-4474 cells in excipient buffer for over 1 year.

The in vitro killing efficiency data shown in FIG. 29B clearly shows that freshly cultured positive (GN-4474) killed target *P. aeruginosa* PA14 pathogen as expected with surviving *P. aeruginosa* PA14 never exceeding 20%. The snap-frozen samples of GN-4474 killed target *P. aeruginosa* PA14 pathogen to similar levels as positive control freshly cultured GN-4474 through the entire 410 days of storage. In all but one of the time points (day 28) the surviving target pathogen levels were all below 15% surviving.

These data indicates that this 'snap freezing' protocol maintains both the viability and killing efficiency of GN-4474 in excipient buffer for at least 1 year at a −80° C. storage temperature. As noted, substantially less glycerol (2%) is used than is typically used for snap freezing bacteria (15-20%)

This protocol was repeated using 50 ml conical tubes (containing the same 10 ml volume) and glass lyophilization vials (Wheaton 20 ml glass serum vials and capped with gray WESTAR® RS 1M/PK Stoppers from WEST Pharmaceutical), with storage at −80° C. for up to 103 or 141 days respectively (data not shown). Similar results were observed, in that cells frozen and stored in the larger conical tubes maintained viability and killing efficiency similar to freshly cultured GN-4474 (with *P. aeruginosa* survival of <5%), and with storage in glass showing a modest decrease in both activities (with *P. aeruginosa* survival between 9.95% to 27.86%).

Example 10

Freeze Drying

In some embodiments, the product is lyophilized, e.g., for stability, and resuspended at the patient's bedside for application to a wound, to dressings, etc. Lyophilization (sometimes referred to as freeze-drying) is typically a two-step process by which a material is 1) frozen, with water then removed under vacuum by the process of sublimation and then 2) warmed to a temperature above freezing, still under vacuum, where residual water is removed by the process of desorption.

The initial freezing phase during the lyophilization cycle has the following temperatures, rates of temperature change, and holds: 5° C. at a rate of 5° C./minute, hold for 30 minutes; −5° C. at a rate of 5° C./minute, hold for 40 minutes; and −45° C. at a rate of 5° C./minute, hold for 240 minutes.

In certain preferred embodiments, primary and secondary drying steps of the lyophilization cycle have the following temperatures, rates of temperature change, hold times and vacuum (mT): −30.0° C. at a rate of 0.1° C./minute, hold for 4000 minutes at a vacuum of 60.0 mT; −28.0° C. at a rate of 0.1° C./minute, hold for 2250 minutes at a vacuum of 60.0 mT; −10.0° C. at a rate of 0.1° C./minute, hold for 600 minutes at a vacuum of 60.0 mT; 5.0° C. at a rate of 0.1° C./minute, hold for 720 minutes at a vacuum of 60.0 mT; 10.0° C. at a rate of 0.1° C./minute, hold for 480 minutes at a vacuum of 60.0 mT; 20.0° C. at a rate of 0.1° C./minute, hold for 480 minutes at a vacuum of 60.0 mT.

Additional freeze-dried preparations and methods of making and using them are described, e.g., in U.S. Pat. No. 8,715,639, which is incorporated herein in its entirety, for all purposes.

Example 11

Large Scale Cultivation of GN-4474

In addition to the above, experiments were conducted to assess the stability of the GN-4474 grown in a Sartorius CultiBag RM bioreactor, washed with 50 mm $KPO_4$ buffer pH=7.0 using diafiltration, followed by concentration of GN-4474 to $1 \times 10^9$ cfu/ml. The GN-4474 was grown at a temperature of 37° C., at a platform angle of 8°, an initial rocking rate of 25 rpm and air flow of 1.0 l pm. pH was maintained with the addition of 1.0N NaOH. Dissolved oxygen was controlled using two separate cascades controlled by the Sartorius Cultibag RM tower. As the dissolved oxygen drops to 50%, two separate cascades are initiated to maintain dissolved oxygen at 50.0%. The first cascade increases the mixing of pure oxygen being added. When this cascade step is not sufficient to maintain dissolve oxygen at 50% then the second cascade which is increased rocking rate is initiated.

The culture was allowed to grow until the $OD_{600\ nm}$ of the culture reached 1.55, which took ~18 hours. The entire Cultibag containing the GN-4474 culture was then removed from the rocking platform and placed at 4° C. for ~16 hours (overnight). The following morning the GN-4474 culture was concentrated from 7.5 liters down to ~1.0 liter using a 0.45 μM microfiltration cartridge from GE Healthcare (CFP4-E-8A) and a Watson Marlow 620S peristaltic pump. Once the culture was concentrated to ~1.0 liter, diafiltration was initiated. The culture was diafiltered with 20 liters of 50 mM potassium phosphate buffer, pH 7.0, which was pre-chilled to 4° C. The diafiltered culture was then concentrated to ~750 ml using the same microfiltration cartridge and pump setup. The resulting diafiltered GN-4474 was then placed (in the same sterile bioprocessing bag that the diafiltration buffer was in) at 4° C.

The viability of diafiltered GN-4474 samples remained quite consistent throughout the course of this of the experiment (14 days post diafiltering and storage at 4° C.). The viability of GN-4474 throughout this time course stayed between $1.33 \times 10^9$ and $2.86 \times 10^9$ cfus/ml (data not shown. GN-4474 was concentrated and diafiltered to a concentration of ~$1 \times 10^9$ cfu/ml.) With spent medium and metabolic waste and breakdown products removed by filtering and diafiltering, GN-4474 is made very stable at this concentration. These viability data show that GN-4474 at this concentration retained good viability throughout the time course.

The in vitro killing efficiency showed that freshly cultured positive control (GN-4474) killed target P. aeruginosa PAM pathogen very efficiently and as expected with surviving P. aeruginosa PA14 never exceeding 5%. The stored diafiltered GN-4474 samples killed target P. aeruginosa PA14 pathogen to similar levels as positive control through the 14 days of this time course (data not shown). P. aeruginosa PA14 that was treated with test diafiltered GN-4474 never had more than 20% surviving following treatment.

Collectively these data indicate that GN-4474 can be prepared in a relatively large batch amounts in the Sartorius CultiBag RM system (at least up to 50 L), then processed according to the manufacturing methods described below. These data show that diafiltered GN-4474 is stable at a concentration of $1 \times 10^9$ cfu/ml for up to two weeks, and can be stored or transferred to another facility for final processing, e.g., by further concentrating using centrifugation and resuspension in complete excipient buffer followed by snap freezing with or without lyophilization.

Example 12

Stability of Manufactured, Lyophilized GN-4474

Freeze-dried vials were kept in frozen storage (−80° C.) for 10 months. Viability was determined shortly after lyophilization, and subsequently at 2 months and 10 months post manufacture. The following describes viability testing.

Methods
Resuspension of Cakes
1. Crimped safety rings around vials were removed, and entire outside of vials were wiped with 70% ethanol.
2. 8.5 ml of room temp sterile water was drawn up in a 10 ml syringe fitted with a 20 gauge 1½ inch long needle. The needle was inserted through the rubber stopper and water expelled into vial.
3. Immediately after adding the water the vials were inverted and shaken by hand for 30 seconds.
4. The vials were left for 5 minutes at room temperature. Followed by inverting the vials and vortexing at full speed for 1 minute.
5. The vials were left for an additional 5 minutes at room temperature. Followed by inverting the vials and vortexing at full speed for 1 minute.

The vials were then visually inspected to determine if the cakes were fully resuspended.

Viability and In Vitro Killing Assays

Viability and in vitro killing were tested post-lyophilization. Three separate lyophilized vials, at time 0, 2 months, and 10 months post-manufacture, were resuspended and tested. Following resuspension, serial dilutions of the product were prepared in sterile 0.9% saline and the samples were plated on LB+Dap agar plates.

The optical density of each of the resuspended vials was determined in order to standardize each for the in vitro killing assay. For this assay the inputs are standardized to an $OD_{600\ nm}=5.0$. Prior to preparing the vials, the target pathogen (P. aeruginosa PA14) was grown overnight in appropriate culture medium and the cell densities adjusted based on $OD_{600\ nm}$. Normally, a positive control (GN-4474) and negative control (CON37-55A which is identical to GN-4474 without the conjugation genes or killer plasmid) are similarly cultured overnight and cell density adjusted. The positive and negative controls, and test samples, are mixed with the target pathogen, and the cell suspension spotted onto a filter disk placed on the surface of an agar plate to initiate filter conjugation. The assay is incubated at 37° C. for 2 hours.

Following incubation, the cells are harvested from the filter, serially diluted and plated to measure colony forming units (cfus). One cfu represents one bacterium, and the reduction in target pathogen numbers compared to controls indicates killing efficiency of the product strain being tested. The agar plate lacks diaminopimelic acid (DAP), an essential supplement for the growth of GN-4474; thus only the surviving target pathogen will be counted. Serial dilutions are spread on plates using the WASP II (Microbiology International, Frederick, Md.), and cfu's are counted using a computer assisted colony counter, ProtoCOL (Microbiology International, Frederick, Md.).

RESULTS AND CONCLUSIONS

| Viability (GMP Manufactured GN-4474 Lot #0999-135-0002 Lyophilized Product) | | |
| --- | --- | --- |
| Time | Average | Standard Deviation |
| Initial (as Determined by CoH) | 8.10E+09 CFUs/ml | Not Determined |
| 2 Months Storage at −80° C. | 9.36E+09 CFUs/ml | 2.28E+09 CFUs/ml |
| 10 Months Storage at −80° C. | 1.09E+10 CFUs/ml | 6.44E+09 CFUs/ml |

| | In vitro Killing Efficiency (GMP Manufactured GN-4474 Lot #0999-135-0002 Lyophilized Product) | | |
|---|---|---|---|
| Time | % PA14 Surviving After Treatment with + Control | % PA14 Surviving After Treatment with − Control | % PA14 Surviving After Treatment with GMP Vial |
| 2 Months Storage | 2.90% | 100% | 22.56% |
| 10 Months Storage | 1.88% | 100% | 19.99% |

These data show that there is no significant change in viability or in vitro killing efficiency following storage for 10 months.

All publications and patents mentioned in the above specification are herein incorporated by reference for all purposes. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A composition comprising recombinant plasmid pCON44-74.

2. A donor bacterial cell, comprising:
   i) recombinant transmissible plasmid pCON44-74;
   ii) one or more transfer genes conferring upon the donor bacterial cell the ability to conjugatively transfer the transmissible plasmid to a recipient cell,
   iii) a mutation in a gene that renders the donor bacterial cell auxotrophic for a compound.

3. The donor bacterial cell of claim 2, wherein the donor bacterial cell is selected from the group consisting of *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira,* and *Chlamydiae.*

4. The donor bacterial cell of claim 2, wherein the donor bacterial cell is *E. coli* CON31-85A.

5. The donor bacterial cell of claim 2, wherein said donor bacterial cell is auxotrophic for one or more compounds selected from the group consisting an aromatic amino acid, lysine, and 2,6-diaminopimelic acid.

6. The donor bacterial cell of claim 4, wherein said donor bacterial cell is a minicell, a maxicell, or a non-dividing cell.

7. A composition comprising a donor bacterial cell of claim 2.

8. The composition of claim 7, wherein said composition comprises a growth medium devoid of aromatic amino acids.

9. The composition of claim 7, wherein said composition comprises a growth medium supplemented with 2, 6-diaminopimelic acid and lysine.

10. The composition of claim 7, wherein the pH of said composition is pH 7.

11. The composition of claim 7, wherein said composition comprises dissolved oxygen at about 50%.

12. The composition of claim 7, wherein said composition is a growth medium lacking one or more of tyrosine, tryptophan and phenylalanine, p-aminobenzoate and p-hydroxybenzoate.

13. The composition of claim 7, wherein said composition comprises a phosphate buffer.

14. The composition of claim 13, wherein said phosphate buffer comprises sodium phosphate and/or potassium phosphate.

15. The composition of claim 7, comprising an excipient mixture comprising a protective agent and a buffer.

16. The composition of claim 15, further comprising a gelling agent.

17. The composition of claim 15, wherein said protective agent is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, TWEEN 20 polyoxyethylenesorbitan monolaurate detergent, TWEEN 80 polyoxyethylenesorbitan monooleate detergent, and an amino acid hydrochloride.

18. The composition of claim 15, wherein said protective agent is selected from trehalose, sucrose, and glucose.

19. The composition of claim 16, wherein said gelling agent comprises one or more gelling agents selected from the group consisting of hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer.

20. The composition of claim 7, comprising 10% (w:v) trehalose, 2.0% (w:v) glycerol, 0.5% (w:v) hydroxyethylcellulose in 50 mM potassium phosphate buffer.

21. The composition of claim 7, wherein said composition is in freeze-dried form.

22. The composition of claim 15, in freeze-dried form.

23. The composition of claim 20, in freeze-dried form.

24. The composition of claim 7, wherein said composition is a fluid or gel containing between about $5 \times 10^8$ to $5 \times 10^{10}$ donor bacterial cells per ml.

25. A method of treating a tissue surface comprising applying a composition of claim 24 to a surface on said tissue.

26. The method of claim 25, further comprising covering the tissue surface after applying said composition.

27. The method of claim 25, wherein said tissue has a lesion.

28. The method of claim 27, wherein said lesion is selected from burns, cuts, abrasions, abscesses, carbuncles, ulcers, furuncles, and blisters.

29. The method of claim 25, wherein said tissue comprises epithelial tissue.

30. The method of claim 25, wherein said applying comprises soaking, washing, or rinsing a tissue in said composition.

31. The method of claim 25, wherein said composition is applied by a process comprising:
a) applying said composition to a medical device; and
b) contacting said medical device to said tissue.

32. The method of claim 31, wherein said medical device is a bandage, dressing, or gauze.

33. The method of claim 25, wherein said treating comprises applying said composition to said tissue surface a plurality of times at regular intervals.

34. The method of claim 33, wherein said intervals are between 1 hour and 24 hours in length.

35. The method of claim 33, wherein said plurality of times comprises at least three times.

36. The method of claim 34, wherein said intervals are 4 hours in length.

37. A method of treating a bacterial infection of a tissue lesion, comprising
a) applying a composition of claim 7 to an infected lesion in an amount of at least $5 \times 10^9$ cfu per 20 mm$^2$ of tissue area.

38. The method of claim 37, where in step a) is repeated two or more times at regular intervals.

39. The method of claim 38, wherein said intervals are between 1 hour and 24 hours in length.

40. The method of claim 39, wherein said intervals are 4 hours in length.

41. A method of preparing and storing bacterial donor cells, comprising:
a) providing a bacterial donor cell, said bacterial donor cell comprising:
i) a recombinant transmissible plasmid comprising:
1) a gene encoding at least one bactericidal protein operably linked to a promoter such that said plasmid is configured to express said gene encoding a bactericidal protein in a recipient cell;
2) a selectable marker;
ii) a gene encoding at least one immunity protein operably linked to a promoter such that said at least one immunity protein is expressed in said bacterial donor cell, wherein said at least one immunity protein inhibits said at least one bactericidal protein;
iii) a mutation in a gene that renders the donor bacterial cell auxotrophic for a compound;
iv) one or more transfer genes conferring on said donor bacterial cell the ability to conjugatively transfer said recombinant transmissible plasmid to a recipient cell,
b) preparing a culture from said donor bacterial cell in a growth medium supplemented with said compound under conditions that select for said selectable marker;
c) separating donor bacterial cells from said growth medium to produce collected donor bacterial cells;
d) resuspending said collected donor bacterial cells at a concentration of less than $1 \times 10^9$ cfu per ml in a storage medium, wherein said storage medium is selected from the group consisting of:
a solution comprising trehalose and/or sucrose,
a solution comprising a phosphate buffer selected from sodium phosphate or potassium phosphate, and
supplemented or unsupplemented M9 medium;
and
e) storing the collected donor bacterial cells in said storage medium under refrigeration for up to 14 days.

42. The method of claim 41, wherein refrigeration is at approximately 4° C.

43. The method of claim 41, wherein said storage medium further comprises glycerol.

44. The method of claim 41, wherein said storage medium consists of 50 mM KPO$_4$ buffer, 10% trehalose, 2% glycerol and 0.5% hydroxyethyl cellulose.

45. The method of claim 41, wherein said recombinant transmissible plasmid is pCON44-74.

46. The method of claim 41, wherein said bacterial donor cell is an *E. coli* cell.

47. The method of claim 41, wherein said *E. coli* cell is *E. coli* CON31-85A, and wherein said growth medium is supplemented with 2,6-diaminopimelic acid and lysine.

48. A method of preparing a frozen composition of bacterial donor cells for therapeutic use without further culturing, comprising:
   a) providing a bacterial donor cell, said bacterial donor cell comprising:
      i) a recombinant transmissible plasmid comprising:
         1) a gene encoding at least one bactericidal protein operably linked to a promoter such that said plasmid is configured to express said gene encoding a bactericidal protein in a recipient cell;
         2) a selectable marker;
      ii) a gene encoding at least one immunity protein operably linked to a promoter such that said at least one immunity protein is expressed in said bacterial donor cell, wherein said at least one immunity protein inhibits said at least one bactericidal protein;
      iii) a mutation in a gene that renders the donor bacterial cell auxotrophic for a compound;
   b) preparing a culture from said donor bacterial cell in a growth medium supplemented with said compound under conditions that select for said selectable marker;
   c) separating said donor bacterial cells from said culture medium to produce collected donor bacterial cells; and
   d) resuspending said collected donor bacterial cells at a concentration of at least $1\times10^{10}$ cfu per ml in an excipient medium, wherein said excipient medium comprises trehalose and/or sucrose and glycerol; and
   e) snap-freezing the collected donor bacterial cells in said storage medium to a temperature of <45° C.

49. The method of claim 48, wherein said excipient medium comprises 1 to 2% glycerol.

50. The method of claim 48, wherein said excipient medium consists of 50 mM $KPO_4$ buffer, 10% trehalose, 2% glycerol and 0.5% hydroxyethyl cellulose.

* * * * *

SEQUENCE LISTING

```
<160> NUMBER OF SEQ ID NOS: 35

<210> SEQ ID NO 1
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 1
cctcgagcgt tgattggcgt agattacctg                                    30

<210> SEQ ID NO 2
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 2
cggatcccaa ccgtataagc gcaaagatct                                    30

<210> SEQ ID NO 3
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 3
cggatccttt tcccagtcgt ccggcaaaac                                    30

<210> SEQ ID NO 4
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 4
gaagctttgt tgccagcgcc agaaa                                         25

<210> SEQ ID NO 5
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 5
```

-continued cggatccaat tatggtgcaa aacctttcgc                                30

<210> SEQ ID NO 6
<211> LENGTH: 29
<212> TYPE: DNA
<213> ORGANISM: Artificial sequence
<220> FEATURE:
<223> OTHER INFORMATION: Synthetic DNA primer

<400> SEQUENCE: 6
gggatccgcg ctaactcaca ttaattgcg                                 29

<210> SEQ ID NO 7
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 7
gcacaatctt ctcgcgcaac                                           20

<210> SEQ ID NO 8
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 8
gatcgttggc aaccagcatc                                           20

<210> SEQ ID NO 9
<211> LENGTH: 22
<212> TYPE: DNA
<213> ORGANISM: Artificial sequence
<220> FEATURE:
<223> OTHER INFORMATION: Synthetic DNA primer

<400> SEQUENCE: 9
gtcagcaatg tacgcagcta ac                                        22

<210> SEQ ID NO 10
<211> LENGTH: 23
<212> TYPE: DNA
<213> ORGANISM: Artificial sequence
<220> FEATURE:
<223> OTHER INFORMATION: Synthetic DNA primer

<400> SEQUENCE: 10
gtatcgcgct ttcccggtaa tac                                       23

<210> SEQ ID NO 11
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 11
gaagctttgc catcagcgtc aatcaggaag                                30

<210> SEQ ID NO 12
<211> LENGTH: 31
<212> TYPE: DNA

<213> ORGANISM: Artificial sequence
<220> FEATURE:
<223> OTHER INFORMATION: Synthetic DNA primer

<400> SEQUENCE: 12
gggatccgac aatacttccc gtgaacatgg g          31

<210> SEQ ID NO 13
<211> LENGTH: 31
<212> TYPE: DNA
<213> ORGANISM: Artificial sequence
<220> FEATURE:
<223> OTHER INFORMATION: Synthetic DNA primer

<400> SEQUENCE: 13
gggatccaag catgccggtt tggtgtaaag t          31

<210> SEQ ID NO 14
<211> LENGTH: 32
<212> TYPE: DNA
<213> ORGANISM: Artificial sequence
<220> FEATURE:
<223> OTHER INFORMATION: Synthetic DNA primer

<400> SEQUENCE: 14
cactagtgac gcacacgttt gcgtatcata tc         32

<210> SEQ ID NO 15
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 15
acaacgtcgt ggtgattgct ggttt                 25

<210> SEQ ID NO 16
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 16
cgaattaccg ctaaaatcgc                       20

<210> SEQ ID NO 17
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 17
gcaacgatgc agaacgactc                       20

<210> SEQ ID NO 18
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 18
cttcagcgta tcaaacacca tcttc                 25

<210> SEQ ID NO 19
<211> LENGTH: 33
<212> TYPE: DNA
<213> ORGANISM: Artificial sequence
<220> FEATURE:
<223> OTHER INFORMATION: Synthetic DNA primer

<400> SEQUENCE: 19
gggaattcat cgatggtatc gccatcgacg aaa                          33

<210> SEQ ID NO 20
<211> LENGTH: 34
<212> TYPE: DNA
<213> ORGANISM: Artificial sequence
<220> FEATURE:
<223> OTHER INFORMATION: Synthetic DNA primer

<400> SEQUENCE: 20
ggggatccat atcattgcta cccagacaaa gagc                         34

<210> SEQ ID NO 21
<211> LENGTH: 33
<212> TYPE: DNA
<213> ORGANISM: Artificial sequence
<220> FEATURE:
<223> OTHER INFORMATION: Synthetic DNA primer

<400> SEQUENCE: 21
gggcatgcat gattatattt cctgcacgcg tgg                          33

<210> SEQ ID NO 22
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 22
cgtgcggcaa cgatcgcata agaagctttc                              30

<210> SEQ ID NO 23
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 23
cctgtgctca gtatcaccgc cagtg                                   25

<210> SEQ ID NO 24
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 24
gcgtggaccg cttgctgcaa ctctc                                   25

<210> SEQ ID NO 25
<211> LENGTH: 25
<212> TYPE: DNA
<213> ORGANISM: Artificial sequence
<220> FEATURE:

<223> OTHER INFORMATION: Synthetic DNA primer

<400> SEQUENCE: 25
caggttgcag aggaagccga gaagg                                    25

<210> SEQ ID NO 26
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 26
ctgaaatggc atcgcgtgcg gcaac                                    25

<210> SEQ ID NO 27
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 27
ttgtagttag tgtcattcag attgcgctgt                               30

<210> SEQ ID NO 28
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 28
tgctactgct tcgcaatgct ggac                                     24

<210> SEQ ID NO 29
<211> LENGTH: 28
<212> TYPE: DNA
<213> ORGANISM: Artificial sequence
<220> FEATURE:
<223> OTHER INFORMATION: Synthetic DNA primer

<400> SEQUENCE: 29
caagaaagcc atccagttta ctttgcag                                 28

<210> SEQ ID NO 30
<211> LENGTH: 26
<212> TYPE: DNA
<213> ORGANISM: Artificial sequence
<220> FEATURE:
<223> OTHER INFORMATION: Synthetic DNA primer

<400> SEQUENCE: 30
gtggatccga tgcgatcggt agcgtg                                   26

<210> SEQ ID NO 31
<211> LENGTH: 28
<212> TYPE: DNA
<213> ORGANISM: Artificial sequence
<220> FEATURE:
<223> OTHER INFORMATION: Synthetic DNA primer

<400> SEQUENCE: 31
ggtctagacc gggtaatacc ggatagtc                                 28

```
<210> SEQ ID NO 32
<211> LENGTH: 29
<212> TYPE: DNA
<213> ORGANISM: Artificial sequence
<220> FEATURE:
<223> OTHER INFORMATION: Synthetic DNA primer

<400> SEQUENCE: 32
gcgttgacga tacacaaggg tcgcatctg                                        29

<210> SEQ ID NO 33
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 33
ggaagcttgt aggcttcgtc gtcgc                                            25

<210> SEQ ID NO 34
<211> LENGTH: 21
<212> TYPE: DNA
<213> ORGANISM: Artificial sequence
<220> FEATURE:
<223> OTHER INFORMATION: Synthetic DNA primer

<400> SEQUENCE: 34
gcaccagtcg atgtcacatt c                                                21

<210> SEQ ID NO 35
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 35
cgtgctgatt atgccgtgtc                                                  20
```